(12) United States Patent
Peterson et al.

(10) Patent No.: US 9,538,734 B2
(45) Date of Patent: Jan. 10, 2017

(54) GERM CELL ABLATION COMPOUNDS AND USES THEREOF

(71) Applicant: THE GENERAL HOSPITAL CORPORATION, Boston, MA (US)

(72) Inventors: Randall T. Peterson, Belmont, MA (US); Peter J. Schlueter, Saint Paul, MN (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 85 days.

(21) Appl. No.: 14/206,135

(22) Filed: Mar. 12, 2014

(65) Prior Publication Data
US 2014/0261212 A1 Sep. 18, 2014

Related U.S. Application Data

(60) Provisional application No. 61/777,274, filed on Mar. 12, 2013.

(51) Int. Cl.
*A01K 67/027* (2006.01)

(52) U.S. Cl.
CPC ....... *A01K 67/0275* (2013.01); *A01K 2207/05* (2013.01); *A01K 2207/20* (2013.01); *A01K 2227/40* (2013.01); *A01K 2267/02* (2013.01)

(58) Field of Classification Search
USPC .......................................................... 800/20
See application file for complete search history.

(56) References Cited

U.S. PATENT DOCUMENTS 7,194,978 B2 3/2007 Zohar et al.
7,521,057 B2 4/2009 Sower et al.

FOREIGN PATENT DOCUMENTS

WO 2012106026 A2 8/2012

OTHER PUBLICATIONS

Weidlinger (Current Biology, 2003, 13:1429-1434).*
Volpe et al. "Competition among juvenile Atlantic salmon (*Salmo salar*) and steelhead (*Oncohynchus mykiss*): relevance to invasion potential in British Columbia." Canadian J. of Fisheries and Aquatic Science, 2001, 197-207, vol. 58.
Carr et al. "The occurance and spawning of cultured Atlantic salmon (*Salmo salar*) in a Canadian river." ICES, J. of Marine Science, 1997, 1064-1073, vol. 54.
Arai et al. "Genetic improvement of aquaculture finfish species by chromosome manipulation techniques in Japan." Aquaculture, 197, 2001, 205-228.
Donaldson & Benfey. Proceedings of the Third International Symposium on Reproductive Physiology of Fish, 1987, 108-119.
Johnstone. Recent Advances in Aquaculture, 1993, 4, 99-105.
Hu et al. "Antisense for gonadotropin-releasing hormone reduces gonadotropin synthesis and gonadal development in transgenic common carp (*Cyprinus carpio*)." Aquaculture, 2007, 271, 498-506.
Jin et al. "The small molecule primordazine ablates primordial germ cells through a novel regulatory element in the nanos1 3' UTR." 10th International Conference Zebra Fish Development and Genetics, Jun. 20-24; Abstract 21, 2012.
Uzbekova et al. "Transgenic rainbow trout expressed sGnRH-antisense RNA under the control of SGnRH promoter of Atlantic salmon." J. Mol. Endocrinol., Dec. 25, 2000 (3), 337-50.
Fueshko et al. "GABA inhibits migration of luteinizing hormone-releasing hormone neurons in embryonic olfactory explants." J. Neurosci., 1998, 18(7), pp. 2560-2569.
Huang et al. "Novel antivirals inhibit early steps in HPV infection." Antiviral Research, 93:280-287, 2012.

* cited by examiner

*Primary Examiner* — Valarie Bertoglio
(74) *Attorney, Agent, or Firm* — Nixon Peabody LLP; David S. Resnick

(57) ABSTRACT

Provided herein are methods of sterilizing fish by contacting an embryonic or juvenile fish with a compound of formula (I). In some embodiments, the compound is primordazine or a derivative thereof.

11 Claims, 40 Drawing Sheets

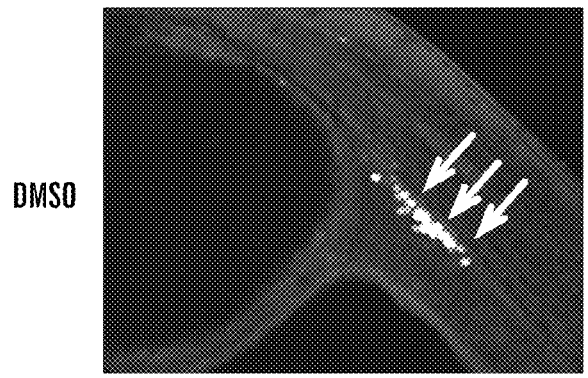
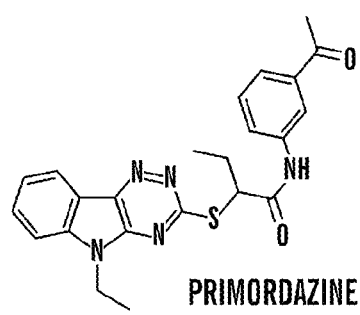
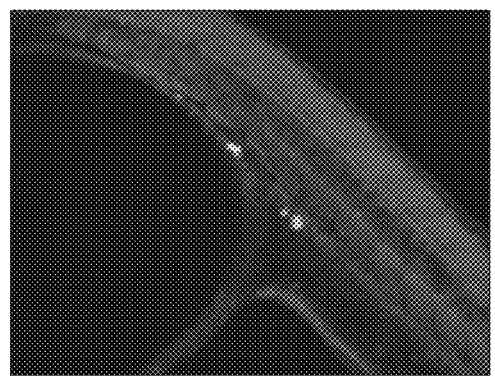
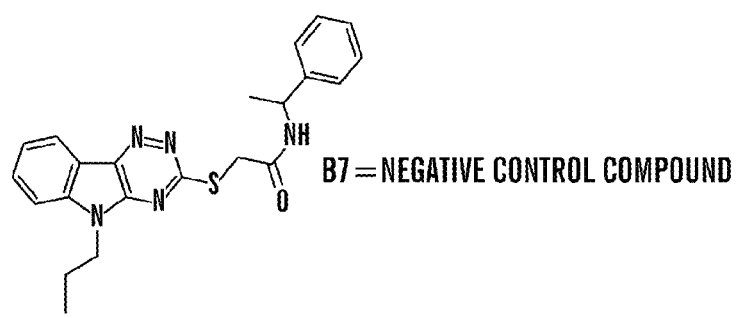
FIG. 1A khsrp (TALEN 770/771) @300 ng/ul

1/26 = 3.84%

ACGTTACAGGTCCCCCAATGAGCAATAACGGCGGAGCGGAGAGTTATCCCTTCCCGACGCC WT
ACGTTACAGGTCCCCCAATGAGCAATAACGG---AGCGGAGAGTTATCCCTTCCCGACGCC Δ3

TIAL1 (TALEN 772/773) @300 ng/ul

29/38 = 76.3%

AGGGATGTTACGGAGGCCCTCATCCTGCAAGTGTTCTCTCAGATCGGCCCCTGCAAGAGCTGTAAAATGATCCTTGATGTGA WT
AGGGATGTTACGGAGGCCCTCATCCT------------------------------TGATGTGA Δ48
AGGGATGTTACGGAGGCCCTCATCCT--------------------------GCAAGAGCTGTAAAATGATCCTTGATGTGA Δ26
AGGGATGTTACGGAGGCCCTCATCCTGCA--------------TCGGCCCCTGCAAGAGCTGTAAAATGATCCTTGATGTGA Δ14
AGGGATGTTACGGAGGCCCTCATCCT-------------CAGATCGGCCCCTGCAAGAGCTGTAAAATGATCCTTGATGTGA Δ13

FIG. 5

1) NO PGC SPECIFICATION DEFECTS AT 3hpf
2) NO MISMIGRATION DURING TRANSITION TO MIGRATORY PHASE
3) PGCs ARE REDUCED BY 18hpf

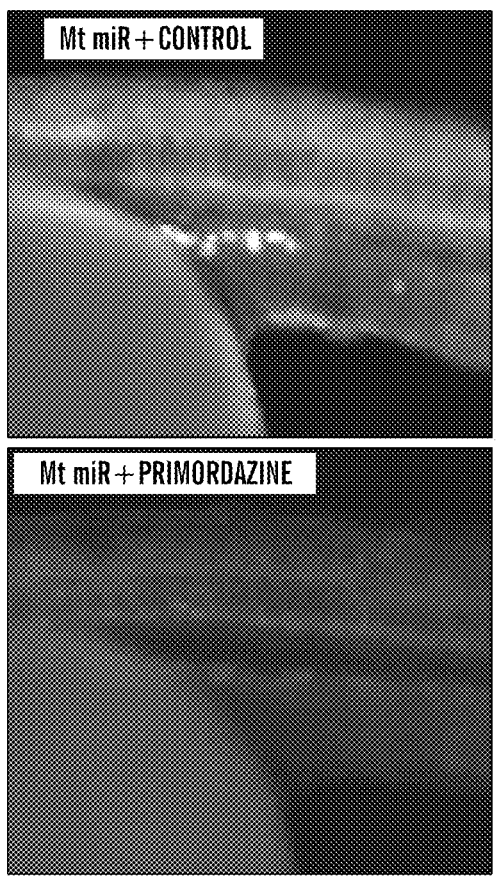
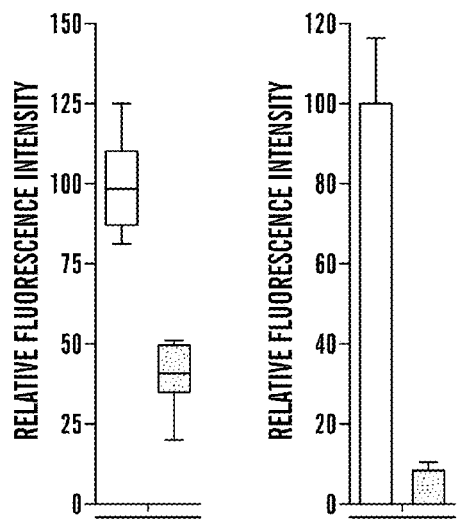
FIG. 14

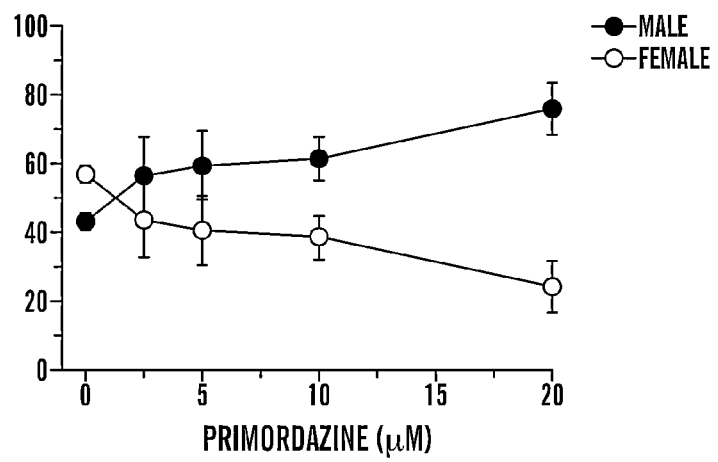
FIG. 27
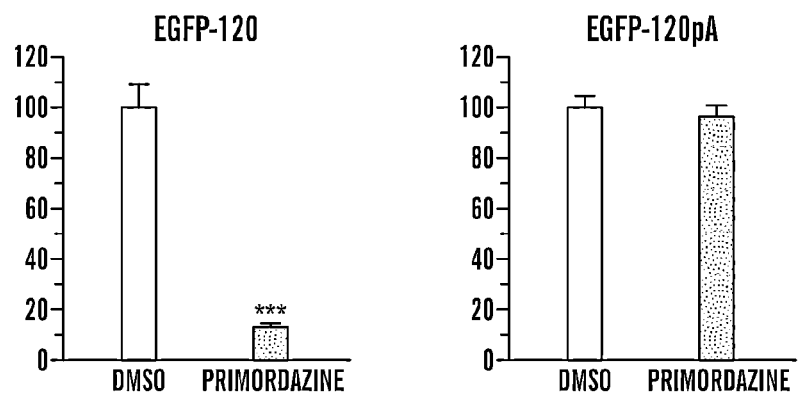
FIG. 28

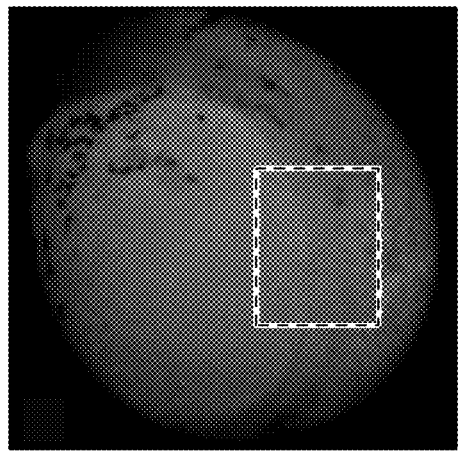
FIG. 41C
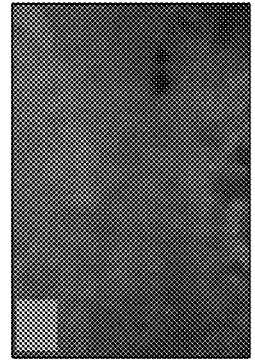
FIG. 41C'
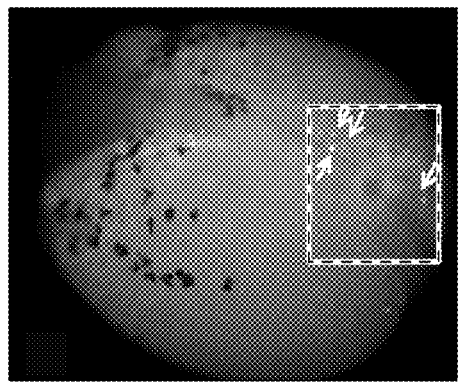
FIG. 41B
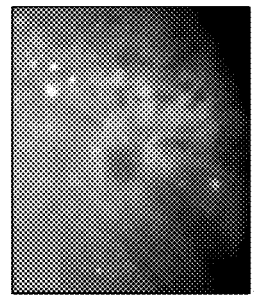
FIG. 41B'
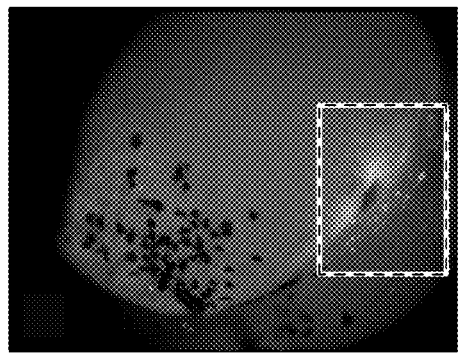
FIG. 41A
FIG. 41A'

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaaaaaaaa aaaaaaaaaa                                              20

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaaaaaaaa aaaaaaaaaa aaaaaaaaaa aaaaa                             35

<210> SEQ ID NO 3
<211> LENGTH: 90
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 3
aaaaaaaaaa aaaaaaaaaa aaaaaaaaaa aaaaaaaaaa aaaaaaaaaa aaaaaaaaaa       60
aaaaaaaaaa aaaaaaaaaa aaaaaaaaaa                                         90

<210> SEQ ID NO 4
<211> LENGTH: 61
<212> TYPE: DNA
<213> ORGANISM: Danio rerio

<400> SEQUENCE: 4
acgttacagg tcccccaatg agcaataacg gcggagcgga gagttatccc ttcccgacgc       60
c                                                                        61

<210> SEQ ID NO 5
<211> LENGTH: 58
<212> TYPE: DNA
<213> ORGANISM: Danio rerio

<400> SEQUENCE: 5
acgttacagg tcccccaatg agcaataacg gagcggagag ttatcccttc ccgacgcc         58

<210> SEQ ID NO 6
<211> LENGTH: 82
<212> TYPE: DNA
<213> ORGANISM: Danio rerio

<400> SEQUENCE: 6
agggatgtta cggaggccct catcctgcaa gtgttctctc agatcggccc ctgcaagagc       60
tgtaaaatga tccttgatgt ga                                                 82

<210> SEQ ID NO 7
<211> LENGTH: 34
<212> TYPE: DNA
<213> ORGANISM: Danio rerio

<400> SEQUENCE: 7
agggatgtta cggaggccct catccttgat gtga                                    34

<210> SEQ ID NO 8
<211> LENGTH: 56
<212> TYPE: DNA
<213> ORGANISM: Danio rerio

<400> SEQUENCE: 8
agggatgtta cggaggccct catcctgcaa gagctgtaaa atgatccttg atgtga            56

<210> SEQ ID NO 9
<211> LENGTH: 68
<212> TYPE: DNA
<213> ORGANISM: Danio rerio

<400> SEQUENCE: 9
agggatgtta cggaggccct catcctgcat cggcccctgc aagagctgta aaatgatcct       60
tgatgtga                                                                 68

<210> SEQ ID NO 10
```

```
<211> LENGTH: 69
<212> TYPE: DNA
<213> ORGANISM: Danio rerio

<400> SEQUENCE: 10
agggatgtta cggaggccct catcctcaga tcggccctg caagagctgt aaaatgatcc        60
ttgatgtga                                                               69
```

GERM CELL ABLATION COMPOUNDS AND USES THEREOF

CROSS-REFERENCE TO RELATED APPLICATION

This application claims benefit under 35 U.S.C. §119(e) of U.S. Provisional Application No. 61/777,274 filed Mar. 12, 2013, the contents of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 24, 2014, is named 030258-077011-US_SL.txt and is 2,386 bytes in size.

BACKGROUND OF THE INVENTION

According to data from the United Nations Food and Agriculture Organization (FAO), world seafood consumption has doubled every 20 to 25 years since 1950 [FAO. 2007 Fishery and Aquaculture Statistics. Rome: Food and Agriculture Organization of the United Nations, 2007]. Today fish from most traditional fisheries are being harvested at maximum yields, while fish populations in almost all commercial marine fisheries around the world are undergoing a dramatic decrease due to over-fishing. In the United States seafood consumption has increased 60% since 1960 and approximately 85% of this demand each year is met by imported fish and shellfish resulting in approximately $7 billion annual trade deficits in edible fishery products [NOAA. Fish Watch U.S. Seafood Fact. In; 2010. See world wide web address: nmfs.noaa.gov/fishwatch/trade_and_aquaculture.htm].

Aquaculture, also known as "fish farming," is becoming increasingly important to offset this deficiency in aquatic foods production, and dramatic increases in aquaculture production have been made over the last few decades. From 2002 to 2007 annual aquaculture production increased from 36.8 million tons to 50.3 million tons with a total value of $87 billion [FAO. 2007 Fishery and Aquaculture Statistics. Rome: Food and Agriculture Organization of the United Nations, 2007]. As this shift in dependence from wild populations to artificially propagated aquatic species continues, optimization of aquaculture methods will be necessary to maximize food production.

According to the Food and Agriculture Organization (FAO) of the United Nations, nearly 70% of the fish species in the world's commercial marine fisheries are now fully exploited, overexploited or depleted. Based on anticipated population growth, it is estimated that the world's demand for seafood will double by the year 2025. Therefore, a growing gap is developing between demand and supply of fisheries products, which results in a growing seafood deficit. Even the most favorable estimates project that in the year 2025, the global demand for seafood will be twice as much as the commercial fisheries will harvest.

The same trend exists in the United States marketplace. Per capita seafood consumption is on the rise, but United States seafood harvests are not increasing to meet the demand. Moreover, only 10% of the seafood consumed in the United States comes from domestic aquaculture and the United States ranks only tenth in the world in the value of its aquaculture production. As a result, the United States is overwhelmingly dependent on imported seafood, such as gilthead and seabream, with more than half of its supplies coming from overseas.

Worldwide, it is estimated that in order to close the increasing gap between the demand and supply of commercially produced fish, aquaculture will need to augment production five-fold during the next two and half decades. While there is a need to increase aquaculture production globally and in the United States, it is clear that fish farming must develop as a sustainable industry without having an adverse impact on the environment.

In commercial fish species where sexual maturation occurs before the fish has reached market size, energy is spent on gonadal growth instead of muscle growth. Sterility increases the conversion of food energy to muscle (thereby resulting in larger fish fillets) and minimizes food energy diverted for development of the gonads. Another advantage of fish sterilization is that it minimizes the potential negative impact of genetically modified fish on the environment, because without sterilization escape of genetically-modified cultured fish may threaten the ecological balance or lead to genetic contamination of wild populations. This threat will become even greater as transgenic fish are raised in commercial operations in the United States and abroad.

Aquaculture experts around the world agree that a mechanically simple, but effective, process that bypasses the traditional modes of inducing sterility would increase production efficiency, profitability and biosecurity in commercial aquaculture. Sterilizing transgenic or genetically-selected fish will minimize the possibility these fish propagating in the wild, an especially important consideration in light of alarming reports of interbreeding between escaped animals and wild populations of the same species, which seem to be increasing in areas of intensive farming (Volpe et al., 2001; Carr et al., 1997).

Several methods currently exist to induce sterility in fish. One method is manipulation of the chromosome number by triploidization or interspecies hybridization and another is the disruption of the gonadotropin-releasing hormone (GnRH) pathway using antisense RNA or treatment with gamma amino butyric acid (GABA).

Chromosome set manipulation for the production of triploid sterile populations is used but it is a cumbersome procedure that must be individually developed for each species. Furthermore, generation of triploids does not always result in sterility. In induced-triploid rainbow trout (Arai, 2001) and Atlantic salmon (Donaldson and Benfey, 1987), males were seldom completely sterile. Because they maintain most of their endocrine competence, these salmonids also exhibit secondary sex characteristics, and as a consequence are susceptible to disease and exhibit no improvement in growth over diploids. Likewise, female triploid Atlantic salmon are commonly found to have a few normal oocytes within the ovarian matrix (Johnstone, 1993). Like CSM, inter-hybridization (or hybrid production) is a labor-intensive process that does not always result in sterility, as is clearly the case with the hybrid striped bass.

Gonadotropin-releasing hormone (GnRH) is a pituitary hormone that is required to maintain a normal reproductive cycle in vertebrates. Specifically, GnRH stimulates the synthesis and secretion of the gonadotropins: follicle-stimulating hormone (FSH) and luteinizing hormone (LH). Generally, the gonads are the primary target organs for LH and FSH. LH and FSH are integral to the reproductive system and inhibition of GnRH signaling and, therefore, disruption of the synthesis and secretion of LH and FSH is a potent method to induce infertility.

Disruption of the GnRH pathway has been accomplished in several species of fish by the introduction of a transgene that encodes antisense RNA that blocks endogenous GnRH expression [Uzbekova S, et al., "Transgenic rainbow trout expressed sGnRH-antisense RNA under the control of sGnRH promoter of Atlantic salmon." *J. Mol. Endocrinol.* 2000; 25: 337-350; Hu W, et al. "Antisense for gonadotropin-releasing hormone reduces gonadotropin synthesis and gonadal development in transgenic common carp (*Cyprinus carpio*)." *Aquaculture* 2007; 271: 498-506.]. Some studies have shown however that low levels of GnRH expression persist in the transgenic fish resulting in a failure to completely induce sterility (Uzbekova S, et al., "Transgenic rainbow trout expressed sGnRH-antisense RNA under the control of sGnRH promoter of Atlantic salmon." *J. Mol. Endocrinol.* 2000, 25: 337-350)

Another disadvantage of this strategy is that it is difficult to maintain a fertile population of fish for brood stock. Since the gene encoding the antisense RNA is integrated into the genome and continuously expressed, all of the fish will carry it, making it necessary to administer exogenous GnRH to individual fish by injection to maintain a fertile brood stock population.

Additionally, GnRH injection of brood stock is not practical in a large-scale commercial aquaculture operation.

Treatment with γ-aminobutyric acid (GABA) has also been proposed to disrupt the GnRH signaling pathway in fish [U.S. Pat. No. 7,194,978.]. Since GABA regulates GnRH neuron development in the embryo, treatment with exogenous GABA is able to disrupt the formation and normal migration pattern of the GnRH neurons [Fueshko S M, et al., "GABA inhibits migration of luteinizing hormone-releasing hormone neurons in embryonic olfactory explants." *J Neurosci* 1998; 18: 2560-2569.]. Although this approach has been used successfully in the laboratory, it is not practical on a commercial scale due to the expense and labor required to treat large populations of fish. Also, the treatment affects other physiological and neurological functions in addition to gonad development in the fish.

As a result of the above constraints, the production of sterile fish, although considered highly beneficial to commercial aquaculture, has not yet been developed for mass use in the industry. Thus, it would be advantageous to develop a method and system to induce permanent sterility in fish grown in commercial operations that overcomes the problems of the previous unsuccessful methods used for sterilization.

SUMMARY OF THE INVENTION

The present invention relates to a simple and generic technology for inducing sterility in farmed fish by disrupting gonadal development, thereby creating fish having more muscle (desirable tissue) and less gonad (undesirable tissue).

An aspect of the present invention relates to a method of inducing sterility in fish, wherein the sterilization method comprises contacting a fish with primordazine or a derivative thereof.

A further aspect of the invention relates to a method of producing a reproductively controllable fish, including contacting fish with primordazine or a derivative thereof.

Another aspect of the present invention relates to a sterile fish obtained by a method of the present invention.

Another aspect of the present invention relates to a kit for distributing compounds that disrupts a primordazine response element in fish and instructions to effectively sterilize fish.

Other aspects, features and embodiments of the invention will be more fully apparent from the ensuing disclosure and appended claims.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

BRIEF DESCRIPTION OF THE DRAWINGS

FIGS. 1A-1B illustrate that primordazine ablates PGCs. (FIG. 1A) The vasa:GFP transgenic shows PGCs at the gonadal ridge (arrows) in DMSO-treated embryos. PGC numbers are reduced by treatment with primordazine. (FIG. 1B) Loss of PGCs is confirmed by in situ hybridization with three PGC-specific markers, vasa, nanos1, and deadend.

(FIG. 2A) GFP RNA with the nanos1 3' UTR and mutated miR-430 site (GFP-Nos1) is injected, and GFP is translated throughout the embryo. Translation is blocked by primordazine treatment. Primordazine sensitivity is conferred by the entire nanos1 3' UTR (Nos1) or the 40-base primordazine response element (PRE), but not by the globin 3' UTR (globin). (FIG. 2B) The primordazine response element can be narrowed to a 40-base sequence from the nanos1 3' UTR by assays as shown in FIG. 2A.

(FIG. 4A) Structure Activity Relationship (SAR) studies enabled optimization of primordazine and identification of a site allowing addition of a covalent linker. For example, additions to the indole nitrogen are well tolerated. (FIG. 4B) Synthesis and purification of the modified primordazine derivative that retains full activity. (FIG. 4C) The primordazine derivative coupled to solid support. (FIG. 4D). A STRING network showing the interactions between DHX9, HNRNPA2B1, HNRNPH1, KHSRP (FUBP2), and TIAL1.

FIG. 5 illustrates evidence of somatic mutation of khsrp and tial1 by TALENs. Pairs of TALENs directed at khsrp and tial1 were injected into single cell stage zebrafish embryos. 48 hours later, genomic DNA was extracted from pools of injected embryos, and the TALEN target sites were amplified by PCR. PCR products were cloned and sequenced, revealing a variety of insertions and deletions at the target sites (SEQ ID NOS 4-10, respectively in order of appearance). TALEN binding sites are marked in yellow, deleted nucleotides are marked by hyphens, and inserted sequence is marked in blue.

(FIG. 6A) Injection of antisense KHSRP MO causes a loss of PGCs, as visualized in the vasa:GFP transgenic line. (FIG. 6B) Co-injection of KHSRP MO with the GFP-nanos1 reporter construct causes a loss of GFP expression that mimics treatment with primordazine. Relative fluorescence represents the amount of GFP fluorescence, normalized to GFP RNA. In FIG. 6B, the series from left to right is DMSO, primordazine, and fubp2 MO.

FIG. 14 illustrates that primordazine acts via a miR-430-independent mechanism. The relative fluorescence intensity is higher for the untreated sample than the primordazine-treated sample.

FIG. 27 illustrates that zebrafish embryos treated with primordazine during early development tend to be males when they become adults. The percentage of each sex is represented after treatment with different doses of primordazine.

FIG. 28 illustrates that primordazine only blocks translation of mRNAs that have short polyA tails. EGFP mRNA was fused to 120 bases from the nanos1 3'UTR. Primordazine effectively blocked translation of EGFP in the absence of polyadenylation, but when the mRNA was polyadenylated in vitro prior to injection in to zebrafish, primordazine failed to block translation.

Between 8 and 11 embryos were analyzed in each treatment group. Standard deviations are shown by vertical bars.

Figure 40:
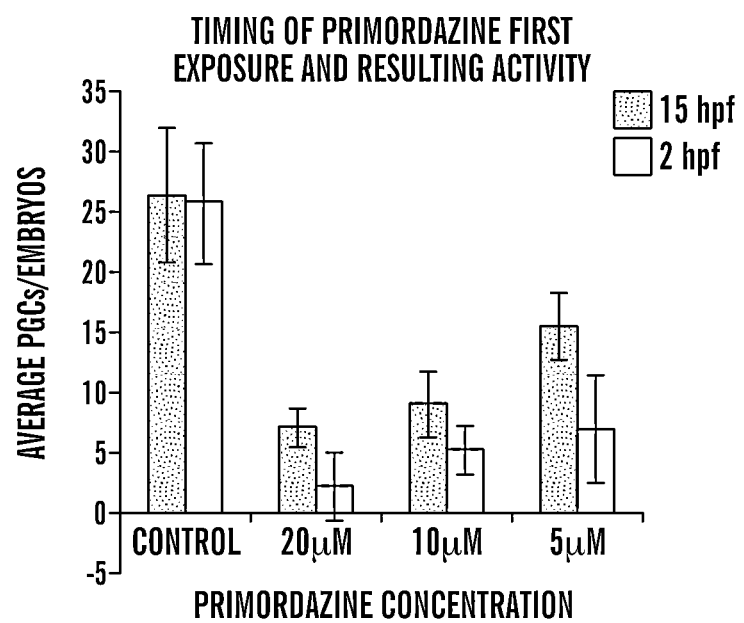

FIG. 40 shows experimental results after Tilapia embryos at the 1 cell stage (2 hpf) and early gastrulation stage were exposure to 20 uM 10 uM 5 uM. At 3 day post fertilization PGCs found at the midline trunk region above the intestine were counted. A minimum of 10 embryos were analyzed in each treatment and control groups. Standard deviations are shown by vertical bars.

Figure 41D:
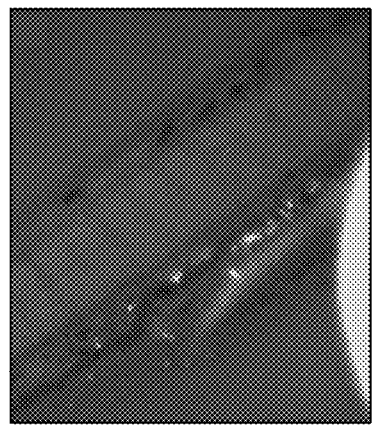
Figure 41E:
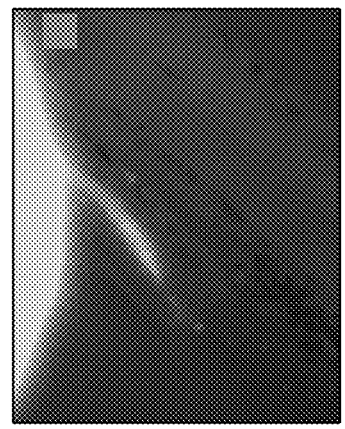
Figure 41F:

FIGS. 41A-F show that PGC numbers are reduced by treatment with primordazine in a dose dependent manner. 1 cell stage tilapia embryo progeny of a transgenic female carrying the Zpc5:eGFP;tnos 3'UTR construct and a wild type male were exposed to primordazine. (FIGS. 41A-41C) Fluorescent images of sibling 3 day old tilapia embryos, control (FIG. 41A) and exposed to 10 uM (Fig. B) and 20 uM (Fig. C) of primordazine. A'-C') Magnification of the white doted area showing the midline trunk region of each embryo. Untreated control embryos show large round shape GFP cells distributed in two rows (A'). Exposure to primordazine results in a marked reduction in number (B') or complete disappearance (C') of GFP labeled cells (arrows). (FIGS. 41D-41E) Fluorescent images of 5 day old embryos control (FIG. 41D), or treated with primordazine at hatching water concentration of 10 uM (FIG. 41E) and 20 uM (FIG. 41F).

DETAILED DESCRIPTION OF THE INVENTION

The present invention is an innovative, simple and generic technology for inducing sterility in farmed fish. This technology aims to block the maintenance of primordial germ cells (PGCs) to induce sterility. The phenotypic result of this technology is a market-sized fish that has more muscle (desirable tissue) and less gonad (undesirable tissue). The invention also provides fish generated according to methods of the invention.

The present invention provides a method of producing sterilized fish that is useful, efficient and cost-effective for sterile fish production. The methods are generally applicable to both small scale and large scale fish sterilization. The method relates to disruption of germ cell development in the fish to be sterilized.

Primordial germ cells (PGCs) are a population of cells in the fish embryo that are precursors to the gametes of the adult fish. The PGCs are produced during the very early stages of embryo development before individual tissues and organs begin to form. At later stages of normal embryo development, as the individual organs are forming, the PGCs migrate through the embryo from their original location to the area of the gonadal precursors. At the end of their migration the PGCs enter the developing gonads and colonize the tissue.

When the embryo eventually undergoes sexual differentiation, the gonad completes development to form a testis or ovary in the male or female, respectively, and the PGCs that previously colonized the gonad differentiate to produce either sperm or eggs, respectively. This same basic scenario of gonad formation and germ cell migration and differentiation is found in all vertebrates including fish and mammals [Doitsidou M, et al., "Guidance of primordial germ cell migration by the chemokine SDF-1." *Cell* 2002; 647-659; Molyneaux K A, et al., "The chemokine SDF1/CXCL12 and its receptor CXCR4 regulate mouse germ cell migration and survival." *Development* 2003; 130: 4279-4286.].

Described herein is a process for inducing sterility in commercially important marine species by contacting fish with primordazine or a derivative thereof. In some embodiments, the fish is trout. In some embodiments, the fish is tilapia. In some embodiments, the fish is salmon.

The inventors have shown a clear loss of germ cells in the tilapia embryos after primordazine treatment (see Example 11). Tilapia is one of the most important food fish in the world, second only to carp, and tilapia culture represent one of the fastest growing sectors in the global aquaculture industry. However, production is hampered by escalating production costs and regional restrictions in their culture (due to concerns with escapement and environmental impacts on wild/native species). In addition, current tilapia production largely relies on costly hormonal sex-reversal practices, using MT (Methyltestosterone) to produce all-male populations. Culture of monosex tilapia yields improved growth characteristics, food conversion ratio, and reduces variation in harvest size, sexual territorial behaviour and the risk of environmental impact from escapes. A process of treating tilapia embryos with primordazine to ablate PGCs and produce a population of sterile and possibly male fish would have great value for this industry.

In one embodiment, the invention provides a method to efficiently ablate PGCs in large numbers of fish embryos, resulting in large-scale production of reproductively sterile adult fish.

The method of present invention comprises contacting fish with primordazine or a derivative thereof. Without being bound by theory, primordazine's mechanism of action was traced to a short, 40-nucleotide sequence in the 3' untranslated region (UTR) of the nanos1 gene. This sequence, referred to as the primordazine response element (PRE) by the inventors, is sufficient to confer primordazine sensitivity to nanos1 or even to exogenous genes (e.g. GFP) that are engineered to contain the PRE within their 3' UTR. Primordazine alters the localization and translation of nanos1 RNA in germ cells, and because nanos1 is essential for germ cell maintenance (Koprunner, M., Thisse, C., Thisse, B. & Raz, E. A zebrafish nanos-related gene is essential for the development of primordial germ cells. *Genes Dev* 15, 2877-2885 (2001)), primordazine ablates PGCs. Without wishing to be bound by theory, because the molecular machinery responsible for germ cell mRNA translation within PGCs is evolutionarily conserved in heterologous fish species, primordazine or a derivative thereof can be applied to sterilize a broad range of host target fish species.

As demonstrated by the examples set forth herein, the present inventors have shown that primordazine blocks expression by altering the localization of nanos1 mRNA.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As defined herein, "sterilizing" fish is understood to mean making a fish unable to sexually reproduce. Sterile fish are defined as fish that are unable to reproduce when reaching sexual maturity.

As defined herein, "fish" means any commercially farmed fish species, either freshwater or saltwater species, including, without limitation, gilthead seabream (*Sparus aurata*), haddock, reedfish (*Calamoichthys calabaricus*), sturgeon (*Acipenser transmontanus*), snook (*Centropomus undecimalis*), black sea bass (*Centropristis striata*), masu salmon, Atlantic salmon, rainbow trout, monkfish, sole, perch, grouper, catfish, blue gill, yellow perch, white perch, sunfish, tilapia, flounder, mahi mahi, striped bass, shad, pike, whitefish, swordfish, red snapper, baramundi, turbot, red drum, as well as ornamental species such as zebrafish.

As defined herein, "functional equivalent" means that the compound retains some or all of the biological activity of the corresponding compound.

The term "functional analog," as used herein means compounds derived from a particular parent compound by straightforward substitutions that do not result in a substantial (i.e. more than 100 times) loss in the biological activity of the parent compound, where such substitutions are modifications well-known to those skilled in the art.

Certain compounds of the present invention and definitions of specific functional groups are also described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group," has used herein, it is meant that a particular functional moiety, e.g., C, O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference. Furthermore, a variety of carbon protecting groups are described in Myers, A.; Kung, D. W.; Zhong, B.; Movassaghi, M.; Kwon, S. *J. Am. Chem. Soc.* 1999, 121, 8401-8402, the entire contents of which are hereby incorporated by reference.

As used herein, the terms "alkyl," "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl, cyclopropylmethyl, adamantly, norbornane, and norbornene. This is also true of groups that include the prefix "alkyl-," such as alkylcarboxylic acid, alkyl alcohol, alkylcarboxylate, alkylaryl, and the like. Examples of suitable alkylcarboxylic acid groups are methylcarboxylic acid, ethylcarboxylic acid, and the like. Examples of suitable alkylacohols are methylalcohol, ethylalcohol, isopropylalcohol, 2-methylpropan-1-ol, and the like. Examples of suitable alkylcarboxylates are methylcarboxylate, ethylcarboxylate, and the like. Examples of suitable alkyl aryl groups are benzyl, phenylpropyl, and the like.

These may be straight chain or branched, saturated or unsaturated aliphatic hydrocarbon, which may be optionally inserted with N, O, or S. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like.

As used herein, the term "alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

As used herein, the term "alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

The term "aryl" as used herein includes carbocyclic aromatic rings or ring systems. As used herein, the term "aryl" refers to an aromatic 5-8 membered monocyclic, 8-12 membered bicyclic, or 11-14 membered tricyclic ring system. Examples of aryl groups include phenyl, naphthyl, biphenyl, fluorenyl and indenyl.

The term "heteroaryl" includes aromatic rings or ring systems that contain at least one ring hetero atom (e.g., O, S, N). As used herein, the term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, thiazolyl, benzimidazolyl, pyrimidinyl, thiophenyl or thienyl, quinolinyl, indolyl, oxazolyl, isoquinolinyl, isoindolyl, thiazolyl, pyrrolyl, tetrazolyl, pyrazolyl, oxazolyl, thiazolyl, benzofuranyl, benzothiophenyl, carbazolyl, benzoxazolyl, benzimidazolyl, quinoxalinyl, benzothiazolyl, naphthyridinyl, isoxazolyl, isothiazolyl, purinyl, quinazolinyl, and the like. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5-membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms. Particularly preferred heteroaryl groups are 5-10-membered rings with 1-3 heteroatoms selected from O, S, and N.

The aryl, and heteroaryl groups can be unsubstituted or substituted by one or more substituents independently selected from the group consisting of alkyl, alkoxy, methylenedioxy, ethylenedioxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, arylcarbonyloxy, arylcarbonylhio, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, arylcarbonylaminoalkyl, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If other groups are described as being "substituted" or "optionally substituted," then those groups can also be substituted by one or more of the above enumerated substituents.

The term "arylalkyl," as used herein, refers to a group comprising an aryl group attached to the parent molecular moiety through an alkyl group.

As used herein, the term "cyclyl" refers to a nonaromatic 5-8 membered monocyclic, 8-12 membered bicyclic, or 11-14 membered tricyclic ring system, which can be saturated or partially unsaturated. Representative saturated cyclyl groups include, but are not limited to, cyclopropyl, cyclobutyl, cyclopentyl, cyclopentenyl, cyclohexyl, cyclohexenyl, cycloheptyl, cyclooctyl, and the like; while unsaturated cyclyl groups include cyclopentenyl and cyclohexenyl, and the like.

The terms "heterocycle", "heterocyclyl" and "heterocyclic group" are recognized in the art and refer to nonaromatic 3- to about 14-membered ring structures, such as 3- to about 7-membered rings, whose ring structures include one to four heteroatoms, 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. The heterocycle may include portions which are saturated or unsaturated. In some embodiments, the heterocycle may include two or more rings (e.g., cycloalkyls, cycloalkenyls, cycloalkynyls, aryls and/or heterocyclyls) in which two or more carbons are common to two adjoining rings, e.g., the rings are "fused rings." In some embodiments, the heterocycle may be a "bridged" ring, where rings are joined through non-adjacent atoms, e.g., three or more atoms are common to both rings. Each of the rings of the heterocycle may be optionally substituted. Examples of heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, dioxane, morpholine, tetrahydrofurane, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with substituents including, for example, halogen, aryl, heteroaryl, alkyl, heteroalkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, CF$_3$, CN, or the like.

As used herein, the term "halogen" refers to iodine, bromine, chlorine, and fluorine.

As used herein, the terms "optionally substituted alkyl," "optionally substituted cyclyl," "optionally substituted heterocyclyl," "optionally substituted aryl," and "optionally substituted heteroaryl" means that, when substituted, at least one hydrogen atom in said alkyl, cyclyl, heterocylcyl, aryl, or heteroaryl is replaced with a substituent. In the case of an oxo substituent (=O) two hydrogen atoms are replaced. In this regard, substituents include oxo, halogen, alkyl, cyclyl, heterocyclyl, aryl, heteroaryl, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$, wherein n is 0, 1 or 2, R$^x$ and R$^y$ are the same or different and independently hydrogen, alkyl, cyclyl, heterocyclyl, aryl or heterocycle, and each of said alkyl, cyclyl, heterocyclyl, aryl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$.

The term "carbonyl," as used herein, refers to "C(=O)".

The terms "acyl," "carboxyl group," or "carbonyl group" are recognized in the art and can include such moieties as can be represented by the general formula:

wherein W is OR$^w$, N(R$^w$)$_2$, SR$^w$, or R$^w$, R$^w$ being hydrogen, alkyl, heteroalkyl, alkenyl, heteroalkenyl, alkynyl, heteroalkynyl, aryl, heteroaryl, heterocycle, substituted derivatives thereof, or a salt thereof. For example, when W is O-alkyl, the formula represents an "ester," and when W is OH, the formula represents a "carboxylic acid." When W is alkyl, the formula represents a "ketone" group, and when W is hydrogen, the formula represents an "aldehyde" group. Those of ordinary skill in the art will understand the use of such terms.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic, fused, and bridged substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

As used herein, the term "small molecule" refers to a non-peptidic, non-oligomeric organic compound, either synthesized in the laboratory or found in nature. A small molecule is typically characterized in that it contains several carbon-carbon bonds, and has a molecular weight of less than 2000 g/mol, preferably less than 1500 g/mol, although this characterization is not intended to be limiting for the purposes of the present invention. Examples of "small molecules" that occur in nature include, but are not limited to, taxol, dynemicity and rapamycin, Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" *J. Am. Chem. Soc.* 1998, 120, 8565; incorporated herein by reference).

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level (e.g., in the absence of a compound of the invention).

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level (e.g., in the absence of a compound of the invention).

The term "statistically significant" or "significantly" refers to statistical significance and generally means at least two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "substantially" as used herein means a proportion of at least about 60%, or preferably at least about 70% or at least about 80%, or at least about 90%, at least about 95%, at least about 97% or at least about 99% or more, or any integer between 70% and 100%.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

In some embodiments, fish is contacted with a compound of formula (I)

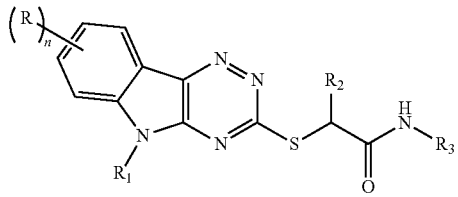

wherein
each $R_1$, $R_2$, and $R_3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

each R is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or —C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo; and n is an integer 0 to 4 inclusive;
with the proviso that:
when n is 0, $R_1$ is ethyl and $R_2$ is ethyl, then $R_3$ is not 5-methylisoxazol-3-yl;
when n is 0, $R_1$ is ethyl and $R_2$ is ethyl, then $R_3$ is not 1-phenylethyl;
when n is 0, $R_1$ is ethyl and $R_2$ is ethyl, then $R_3$ is not 4-(N-hydroxynitrosyl)phenyl;
when n is 0, $R_1$ is ethyl and $R_2$ is H, then $R_3$ is not 4-(N,N-dimethylcarbamoyl)phenyl;
when n is 0, $R_1$ is ethyl and $R_2$ is H then $R_3$ is not 4-carbamoylphenyl at the same time at the same time; or
when n is 0, $R_1$ is propyl and $R_2$ is H, then $R_3$ is not 1-phenylethyl.

In some embodiments, $R_1$ is substituted or unsubstituted, branched or unbranched aliphatic; cyclic or acyclic, substituted or unsubstituted, branched or unbranched heteroaliphatic; substituted or unsubstituted, branched or unbranched acyl.

In some embodiments, $R_1$ is substituted or unsubstituted, branched or unbranched $C_{1-8}$ alkyl. In some embodiments, $R_1$ is substituted or unsubstituted, branched or unbranched $C_{1-4}$ alkyl. In some embodiments, $R_1$ is methyl, ethyl, n-propyl, i-propyl, n-butyl, i-butyl, or t-butyl.

In some embodiments, $R_1$ is $R_1$—X, wherein X is a linker to a solid support.

In some embodiments, $R_2$ is substituted or unsubstituted, branched or unbranched aliphatic; cyclic or acyclic, substituted or unsubstituted, branched or unbranched heteroaliphatic; substituted or unsubstituted, branched or unbranched acyl.

In some embodiments, $R_2$ is substituted or unsubstituted, branched or unbranched $C_{1-8}$ alkyl. In some embodiments, $R_2$ is substituted or unsubstituted, branched or unbranched $C_{1-4}$ alkyl. In some embodiments, $R_2$ is methyl, ethyl, n-propyl, i-propyl, n-butyl, i-butyl, or t-butyl.

In some embodiments, $R_3$ is cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl.

In some embodiments, $R_3$ is substituted or unsubstituted aryl. In some embodiments, $R_3$ is substituted phenyl. In some embodiments, $R_3$ is substituted phenyl, wherein the substitution is not p-C(O)N(CH$_3$)$_2$ or p-C(O)NH$_2$.

In some embodiments, $R_3$ is substituted or unsubstituted alkylaryl. In some embodiments, $R_3$ is not CH(CH$_3$)Ph.

In some embodiments, $R_3$ is substituted or unsubstituted alkylheteroaryl.

In some embodiments, formula (I) is

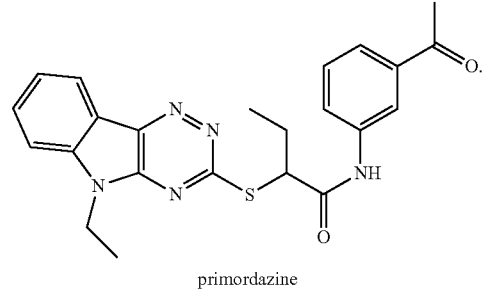 [SMILES: CCC(Sc1nnc2c3ccccc3n(CC)c2n1)C(=O)Nc1cccc(C(C)=O)c1]

primordazine

In some embodiments, formula (I) is

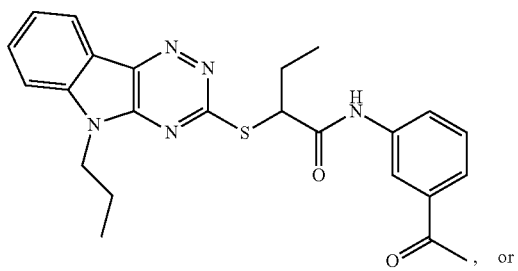

, or

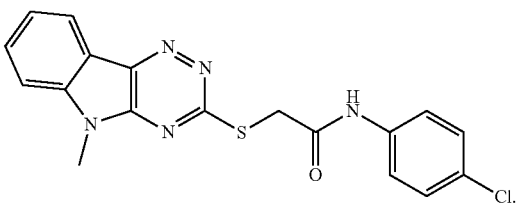

In some embodiments, formula (I) is

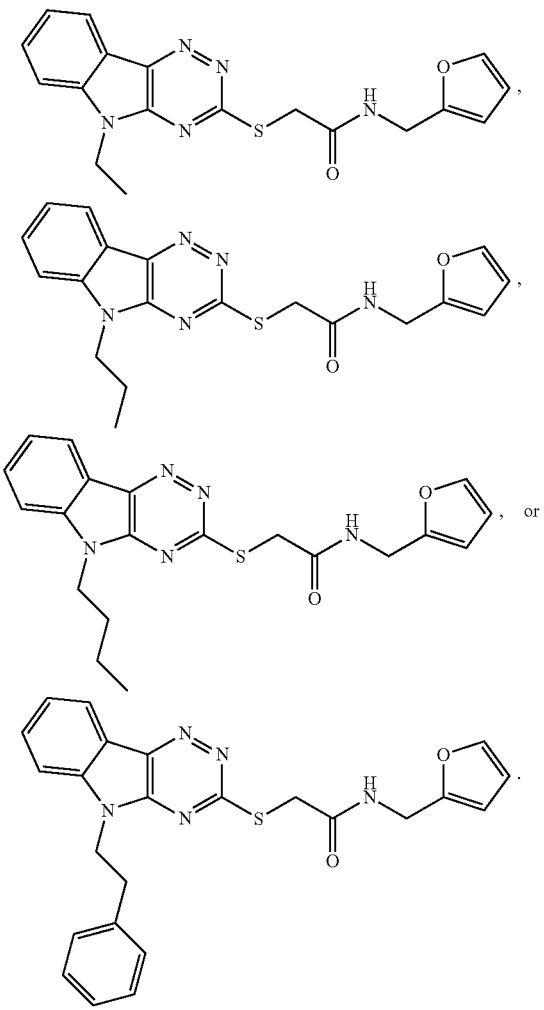

In some embodiments, a compound of formula (I) is attached to a solid support. In some embodiments, the solid support is linked to $R_1$.

In some embodiments, the present invention provides a method of inducing sterility in fish, wherein the sterilization method comprises contacting a fish with a compound of formula (I). In some embodiments, the sterility is complete. In some embodiments, the fertility is decreased. In some embodiments, the sterility is permanent. In some embodiments, the sterility is temporary.

In some embodiments, the present invention provides a method of producing a reproductively controllable fish, comprising contacting fish with a compound of formula (I).

In some embodiments, formula (I) is primordazine or a derivative thereof

In some embodiments, a fish is contacted with a compound of formula (I) at spaced intervals. In some embodiments, the intervals are hourly. In some embodiments, the intervals are daily. In some embodiments, the intervals are weekly. In some embodiments, the intervals are bi-weekly. In some embodiments, the intervals are monthly. In some embodiments, the intervals are bi-monthly.

In some embodiments, a fish is contacted with a compound of formula (I) postfertilization. In some embodiments, the contact is between one minute and one hour postfertilization. In some embodiments, the contact is between one hour and four hour postfertilization. In some embodiments, the contact is between five hours and ten hours postfertilization. In some embodiments, the contact is between ten hours and 24 hours postfertilization. In some embodiments, the contact is between one day and one week postfertilization. In some embodiments, the contact is more than one week postfertilization. In some embodiments, the contact is between 1 and 2 months. In some embodiments, the contact is between 2 and 3 months. In some embodiments, the contact is between 3 and 4 months. In some embodiments, the contact is between 4 and 5 months. In some embodiments, the contact is between 5 and 6 months. In some embodiments, the contact is more than 6 months.

In some embodiments, the present invention provides a fish obtained by a method of the invention. In some embodiments, the fish is completely sterile. In some embodiments, the fish fertility is decreased. In some embodiments, the fish is permanently sterile. In some embodiments, the fish is temporarily sterile.

In some embodiments, the present invention further comprises treating a fish with at least one other sterilization method. In some embodiments, the other sterilization method is chromosome set manipulation. In some embodiments, the other sterilization method is chromosome set manipulation inter-hybridization. In some embodiments, the other sterilization method is hybrid production. In some embodiments, the other sterilization method is the disruption of the gonadotropin-releasing hormone (GnRH) pathway.

Another aspect of the invention relates to a method of forcing a fish to become male, the method comprising contacting the fish with a compound of formula (I). In some embodiments, formula (I) is primordazine or a derivative thereof. The inventors have shown that zebrafish embryos treated with primordazine during early development tend to be males when they become adults (FIG. 27).

Routes of Administration and Dosage Forms

The compositions according to the present invention may be administered by any suitable route including injection, implantation, immersing the embryonic or juvenile fish in a bath of an effective substance or through a feed product. For example, and not by way of limitation, the active ingredient may be directly injected intramuscularly into the fish. In one embodiment, the active compound may be combined with a polymer based carrier matrix into a sustained release delivery system.

The term "sustained release" is understood to mean a gradual release of the active compound in a controlled manner. A suitable carrier having such sustained release properties may be chosen on the basis of its gradual release properties in a solution designed to resemble a fish's plasma, such as a ringer solution, other physiological saline solutions, fish serum, etc.

The polymer based carrier matrix may comprise natural or synthetic polymers or copolymers. Examples of natural polymers are polysaccharides and various proteins. Synthetic polymers or copolymers may either be biodegradable, in which case the sustained release is due to biodegradation, or non degradable, in which case the sustained release is due to gradual diffusion of the active compound therefrom. Examples of biodegradable polymers and copolymers are polylactic polyglycolic acid, polyanhydrides, polyorthoesters and polycaprolactone. Examples of non biodegradable polymers are silicone rubber in a mixture with a relatively large amount of a biocompatible protein, a copolymer of ethylene and vinyl acetate, the relative amount of vinyl acetate being about 20 50%, and various synthetic polysaccharides. In general, any biocompatible polymeric controlled release carrier such as those hitherto used in the art for delivering the compounds of the invention, can in principle be used in accordance with the present invention.

The compositions of the present invention, if delivered in a solid form, can be prepared in any suitable form such as pellets, discs, rods or microspheres. These may be administered to the fish larvae either by implantation of a composition unit (in the form of a pellet, disc or rod) or by injection, either intramuscular, subcutaneous or intraperitoneal (in the form of a suspension of mini-rods or microspheres).

The compositions of the present invention, can be prepared to be incorporated in fish food, such as floating and sinking pellets, granular and flake food.

The size of an implantable composition in accordance with the present invention will be determined both by the size of the fish in which implantation thereof is intended, i.e. it should not be too big, and by practical limitations, i.e. the implantable composition should not be too small so as to render it difficult for manipulation. Thus, for example, a disc having a diameter of about 1-10 mm and a thickness of about 0.012 mm has been found to be suitable for implantation in many fish such as the sea bream, sea bass and trout.

The composition may be administered to the fish either by subcutaneous or intraperitoneal implantation (for injectable micro-rods or spheres). For subcutaneous implantation a small incision are made through the fish's skin at a suitable place and after separating the skin from the underlying muscles, e.g., by the use of forceps, the implantation and incision is made through the skin and muscle of the peritoneal cavity and the implant is inserted through the incision and placed in the peritoneum. The incision in each case is made as small as practicably possible and there is usually no need for post implantational stitching.

Injectable compositions in accordance with the invention in the form of mini-rods or microspheres should be sufficiently small to pass through a syringe. Injectable compositions will be suspended in an injectable solution, such as saline or various buffers, prior to injection and thereafter the suspension is injected into a suitable muscle of the fish or into the peritoneal cavity.

Implantable compositions can comprise about 5-25 uM of the active compounds per unit. In some embodiments, the compositions comprises about 1-100 uM of the active compounds per unit. In some embodiments, the compositions comprises about 1-50 uM of the active compounds per unit. In some embodiments, the compositions comprises about 1-50 uM of the active compounds per unit. In some embodiments, the compositions comprises about 2-40 uM of the active compounds per unit. In some embodiments, the compositions comprises about 3-35 uM of the active compounds per unit. In some embodiments, the compositions comprises about 4-30 uM of the active compounds per unit. In some embodiments, the compositions comprises about 5-25 uM of the active compounds per unit. In some embodiments, the compositions comprises about 5-10 uM of the active compounds per unit. In some embodiments, the compositions comprises about 10-15 uM of the active compounds per unit. In some embodiments, the compositions comprises about 15-20 uM of the active compounds per unit. In some embodiments, the compositions comprises about 20-25 uM of the active compounds per unit. In some embodiments, the compositions comprises about 50-75 uM of the active compounds per unit. In some embodiments, the compositions comprises about 75-100 uM of the active compounds per unit. The amount of the active compound may, in some cases, be reduced if a very active analog is utilized.

For embryonic fish or larvae, the compound of the invention can simply be added to fish feed or water system, either freshwater or saltwater, in various concentrations, as described herein. Additionally, the fish may be subjected to the compound by "dipping" the fish therein. The compound may be fused to a modulator, e.g., organic polycations that adhere to the skin and gills of the fish, thereby transferring the compound of the invention to the fish.

The exposure of the fish to a compound of the invention can include intermittent (e.g., interrupted) as well as continuous (e.g., non-interrupted) exposure. The dose of the compound of the invention that is effective for sterilization can be routinely determined by a veterinarian, although it may vary depending on the species of fish treated, and the age of the fish. In some embodiments, the treatment is administered continuously. In some embodiments, the treatment is administered once. In some embodiments, the treatment is administered daily, for a period of 1-7 days. In some embodiments, the treatment is administered daily, for a period of 7-14 days. In some embodiments, the treatment is administered daily, for a period of 14-21 days. In some embodiments, the treatment is administered daily, for a period of 21-31 days. In some embodiments, the treatment is administered daily, for a period of more than 31 days. In some embodiments, the treatment is administered weekly, for a period of 30-60 days. In some embodiments, the treatment is administered weekly, for a period of 60-90 days. In some embodiments, the treatment is administered weekly, for a period of 90 days or more. In some embodiments, the treatment is administered weekly, for a period of 1-2 weeks days. In some embodiments, the treatment is administered weekly, for a period of 2-4 weeks. In some embodiments, the treatment is administered weekly, for a period of more than 4 weeks.

A treated fish feed may be prepared by incorporating a suitable amount of a compound of the invention into a commercially available fish feed products to achieve the desired dosing levels. The amount of incorporated into the fish feed will depend on the rate at which the fish are fed. For fish fed at the rate of 0.2% to 4% of biomass/day, the treated feed contains from 0.5 to 500 mg of the compound per kg of treated feed. In some embodiments, the treated feed contains from 1 to 450 mg of the compound per kg of treated feed. In some embodiments, the treated feed contains from 10 to 400 mg of the compound per kg of treated feed. In some embodiments, the treated feed contains from 15 to 350 mg of the compound per kg of treated feed. In some embodiments, the treated feed contains from 20 to 300 mg of the compound per kg of treated feed. In some embodiments, the treated feed contains from 25 to 250 mg of the compound per kg of treated feed. In some embodiments, the treated feed contains from 30 to 200 mg of the compound per kg of treated feed. In some embodiments, the treated feed contains from 35 to 150 mg of the compound per kg of treated feed. In some embodiments, the treated feed contains from 40 to 100 mg of the compound per kg of treated feed. In some embodiments, the treated feed contains from 45 to 75 mg of the compound per kg of treated feed. In some embodiments, the treated feed contains from 0.5 to 100 mg of the compound per kg of treated feed.

Kits

Another aspect of the invention relates to a kit for conveniently and effectively carrying out the methods in accordance with the present invention. In general, the kit comprises one or more containers filled with one or more of the ingredients of the compositions of the invention. Optionally associated with such container(s) can be written instructions for administering it according to the appropriate dosing levels and schedule. Additional examples of items contained in the kit include, but are not limited to, various containers (e.g., bottles, cartons, blister packs, and ampules) either accompanied by a package insert describing the cyclical dosing instructions, or wherein the dosing instructions are printed on, or affixed to the container. The compound or its salt may be in the form of a pre-mix, comprising one or more diluents and 0.01 to 25% by weight of the compounds.

Some embodiments of the invention are listed in the following paragraphs:
1. A method of sterilizing fish comprising: contacting an embryonic or juvenile fish with a compound of formula (I).
2. The method of paragraph 1, wherein formula (I) is primordazine.
3. The method of paragraph 1, wherein the compound is administered at spaced intervals.
4. The method of paragraph 1, wherein the compound is administered daily.
5. The method of paragraph 1, wherein the compound is administered weekly.
6. The method of paragraph 1, wherein the compound is administered monthly.
7. The method of paragraph 1, wherein the sterilization is temporary.
8. The method of paragraph 1, wherein the sterilization is permanent.
9. The method of paragraph 1, wherein contacting is by administration to the water wherein the fish are swimming.
10. The method of paragraph 1, wherein contacting is by injection, implantation, or orally through feed.
11. The method of paragraph 1, wherein the fish is contacted with the compound at about 1-5 hours, 10 hours, 3 days, 1 week, 2 weeks, 3 weeks, 1 month, 2 month 3 month, or 90 days post fertilization.
12. The method of paragraph 1, further comprising treating the fish with at least one other sterilization method.
13. A fish obtained by the method of any of paragraphs 1-10.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art. The following examples contain important additional information, exemplification and guidance which can be adapted to the practice of this invention in its various embodiments and the equivalents thereof.

These and other aspects of the present invention will be further appreciated upon consideration of the following Examples, which are intended to illustrate certain particular embodiments of the invention but are not intended to limit its scope, as defined by the claims.

EXAMPLES

Example 1

Figure 1B:
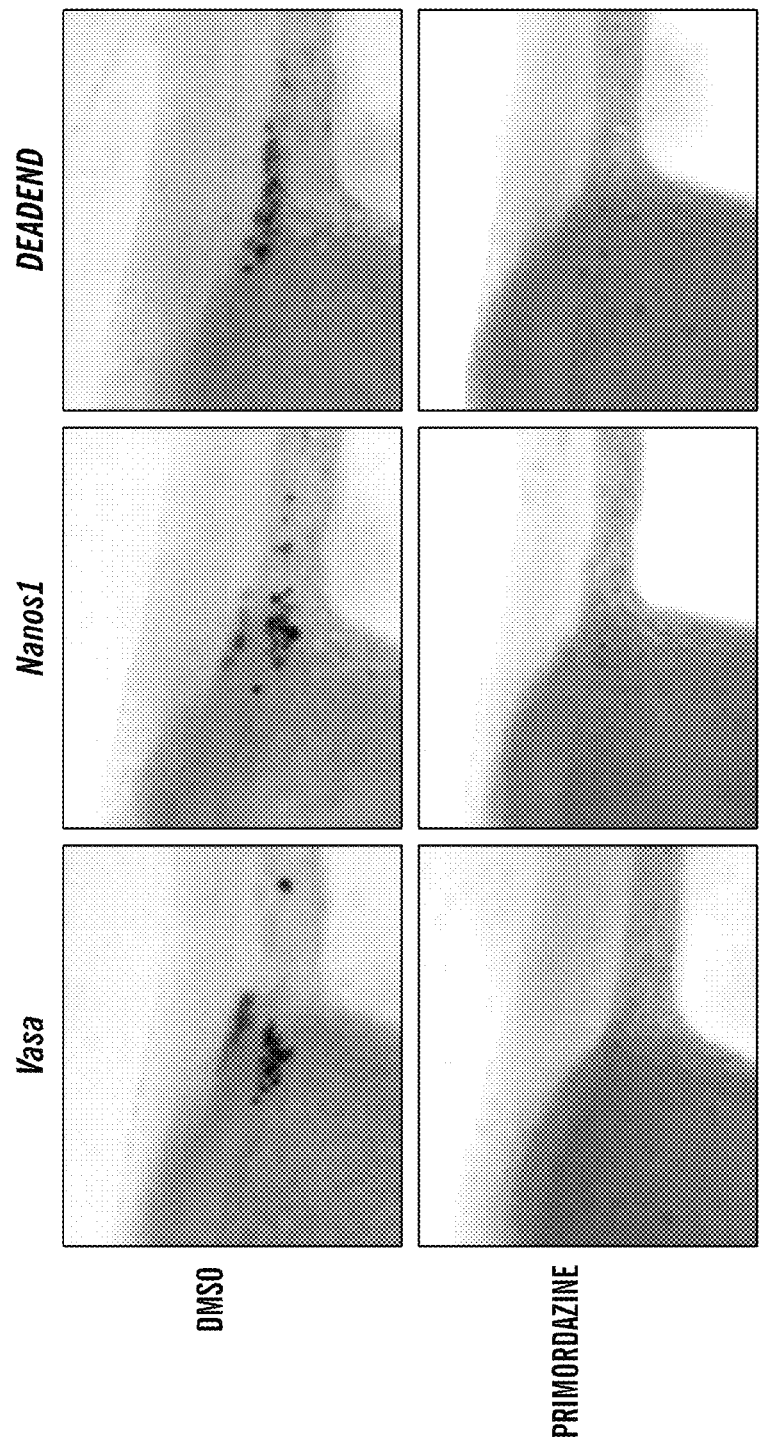

Effects of Primordazine on Protein Localization and Interaction with the PRE Primordazine Ablates PGCs In an effort to discover pathways essential for PGC maintenance, a small molecule screen for compounds that promote disappearance of PGCs was performed. The screen was performed with transgenic zebrafish embryos that express GFP exclusively in PGCs. Of 7,000 small molecules screened, three caused disappearance of PGCs without causing other observable changes in embryonic development. The three PGC-ablating compounds were close structural analogs of each other, and the representative compound from this class was named primordazine (FIG. 1A). Treatment of embryos with primordazine ablates PGCs in a dose-dependent manner, but only when treatment begins prior to 4 hours postfertilization. PGC loss was confirmed by multiple PGC lineage markers (FIG. 1B).

Primordazine Functions Through a 40-Base Response Element in 3' UTRs

Figure 2A:
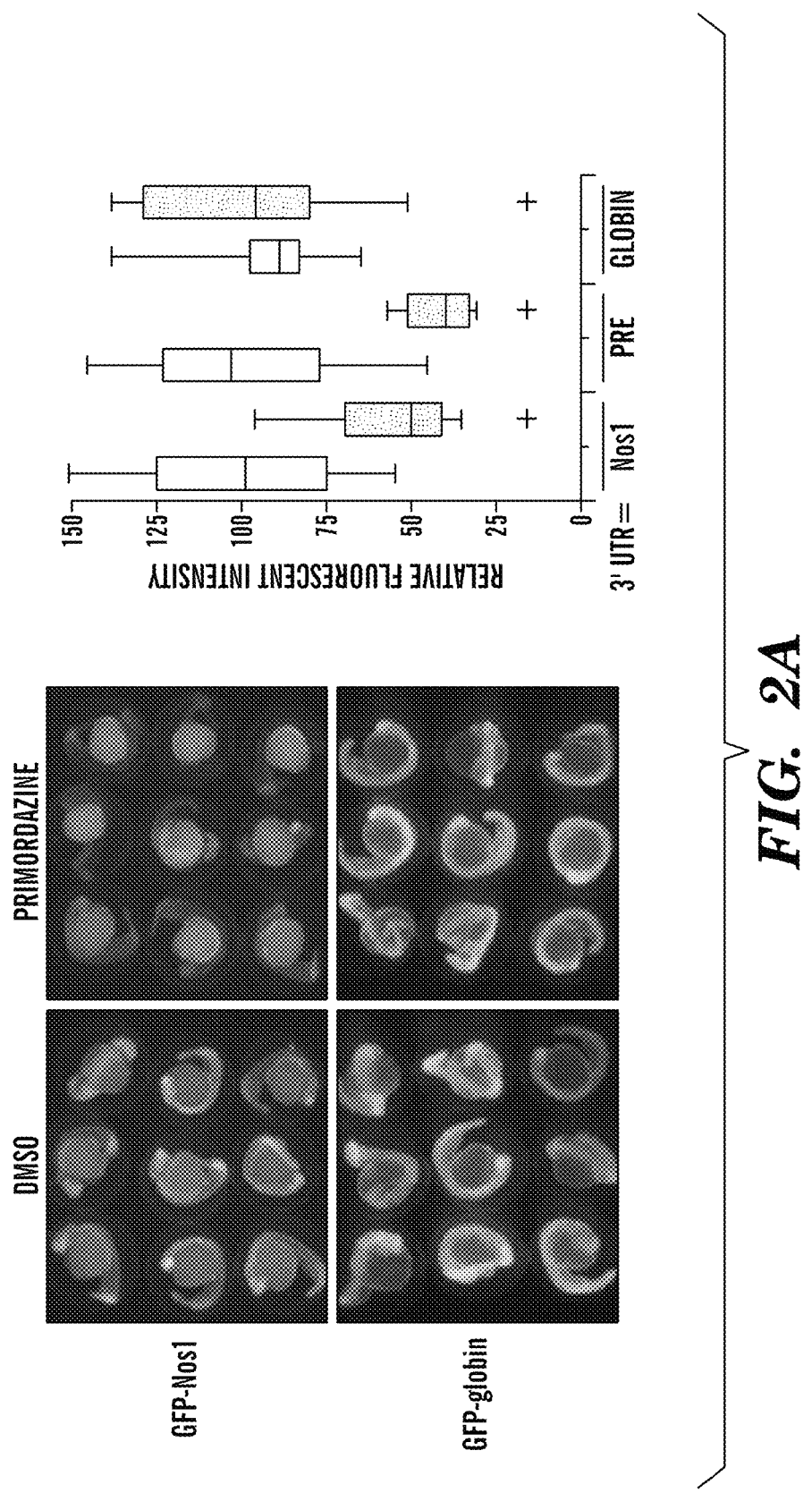
FIGS. 2A-2B illustrate that primordazine functions through a 40-base primordazine response element in 3' UTRs. The nanos1 3' UTR is sufficient to make GFP translation conditional.

During the process of confirming PGC loss in primordazine-treated embryos, it was discovered that GFP translation was highly sensitive to primordazine treatment when fused to the 3' UTR of the nanos1 gene, but not when fused to other 3' UTRs. The 3' UTR of the nanos1 gene was examined for elements capable of conferring primordazine sensitivity. A single sequence of 40 bases was found to be sufficient to render even exogenous genes (like GFP) sensitive to primordazine treatment. This sequence is called the Primordazine Response Element (PRE). As shown in FIG. 2A, translation of GFP RNA injected into zebrafish is blocked by primordazine when the PRE is placed in its 3' UTR. When other sequences from the nanos1 3' UTR are used, primordazine has no effect on GFP expression.

Primordazine Alters the Localization of Nanos1 mRNA

Figure 3:
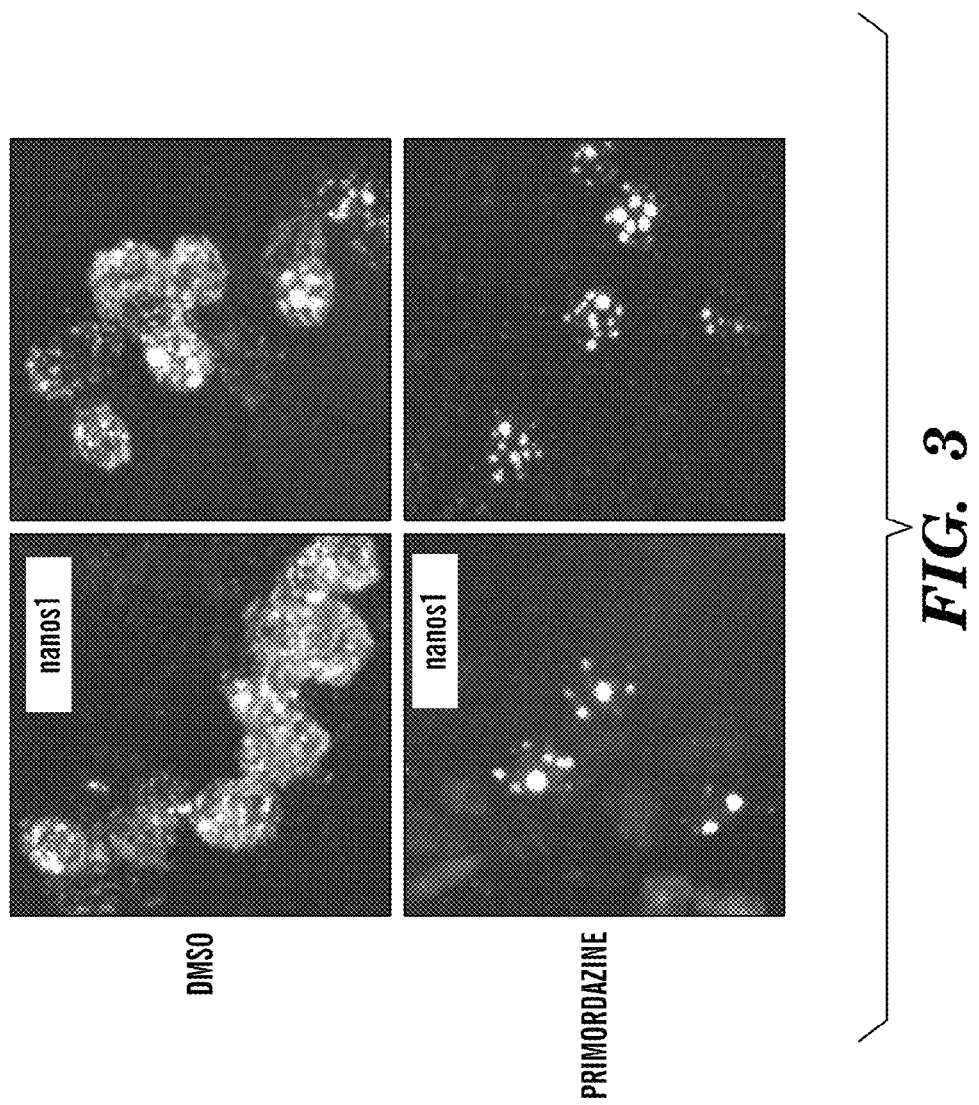
FIG. 3 illustrates that primordazine alters the localization of nanos1 mRNA. Whole-mount, fluorescent in situ hybridization of endogenous nanos1 mRNA enabled visualization of nanos1 localization in primordial germ cells. Primordazine treatment causes a consistent relocalization of nanos1 mRNA from a diffuse, cytoplasmic pattern to discrete puncta. Imaging by confocal microscopy.

Quantitative PCR showed no decrease in nanos1 mRNA levels (not shown). Therefore, mRNA destabilization is not the mechanism by which primordazine blocks nanos1 expression. Next, fluorescent in situ hybridization and confocal microscopy were used to examine the localization of nanos1 mRNA within germ cells. It was found that nanos1 mRNA was distributed throughout the cytoplasm in untreated zebrafish germ cells but became localized to discrete puncta following treatment with primordazine (FIG. 3). This observation suggests that primordazine blocks expression by altering the localization of nanos1 mRNA, not by destabilizing it.

KHSRP and TIAL1 Bind the Primordazine Response Element (PRE)

To ascertain the mechanisms by which the primordazine response element (PRE) controls mRNA localization and expression, a quantitative method was sought to discover the proteins that interact with the PRE. A biotinylated RNA oligomer with the PRE sequence was synthesized and used as an affinity reagent to purify PRE-binding proteins. Proteomic techniques were used to identify and quantify the binding proteins (Ong, S. E. et al. Stable isotope labeling by amino acids in cell culture, SILAC, as a simple and accurate approach to expression proteomics. *Mol Cell Proteomics* 1, 376-386 (2002); Ross, P. L. et al. Multiplexed protein quantitation in *Saccharomyces cerevisiae* using amine-reactive isobaric tagging reagents. *Mol Cell Proteomics* 3, 1154-1169 (2004)). To verify results, experiments were performed both with cultured mammalian cells and with zebrafish embryos. Two distinct proteomic techniques, SILAC and iTRAQ were used to give further confidence to the findings, and two distinct types of controls were used (competition with non-biotinylated PRE and with irrelevant sequence). Nine proteins were consistently found to bind to the PRE and not to irrelevant sequences. Most of these proteins were identified from both mammalian and zebrafish cells, by multiple analytical methods. Of the proteins identified, KHSRP and TIAL1 were focused on for three reasons: 1) They possess known RNA binding domains, consistent with direct binding to the PRE. 2) Knockdown of KHSRP or TIAL1 ablates PGCs. 3) Both KHSRP and TIAL1 interact with the RNA helicase DHX9, which were discovered to bind to primordazine (see below).

DHX9 Binds to Primordazine and Interacts with KHSRP and TIAL1

Figure 4B:
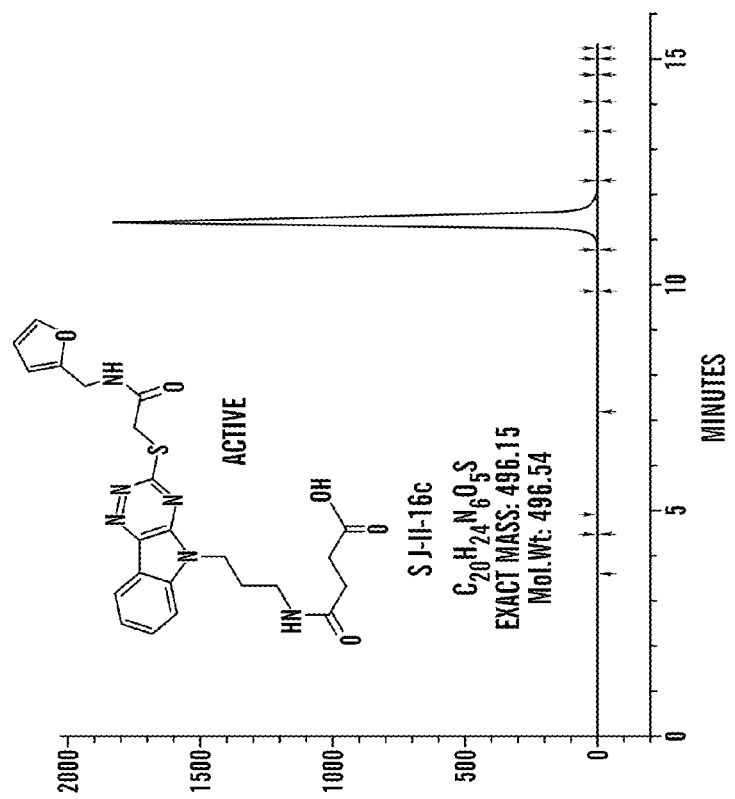
FIGS. 4A-4D illustrate the synthesis of an affinity matrix, and discovery of a primordazine-binding helicase.
Figure 4A:
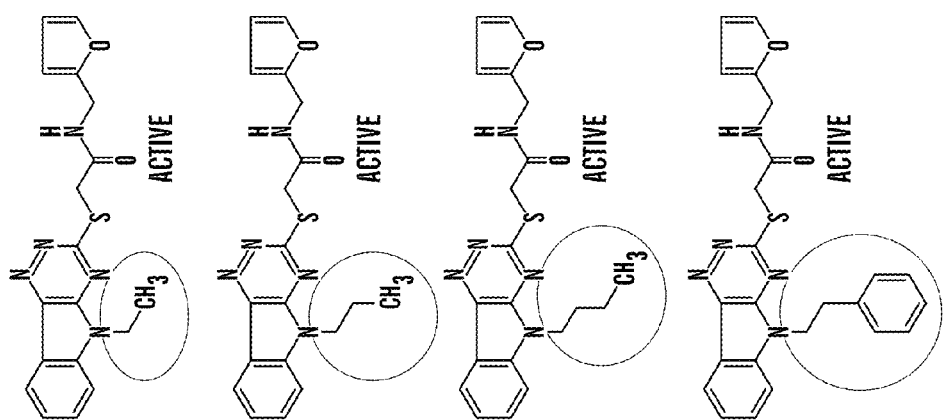
Figure 4D:
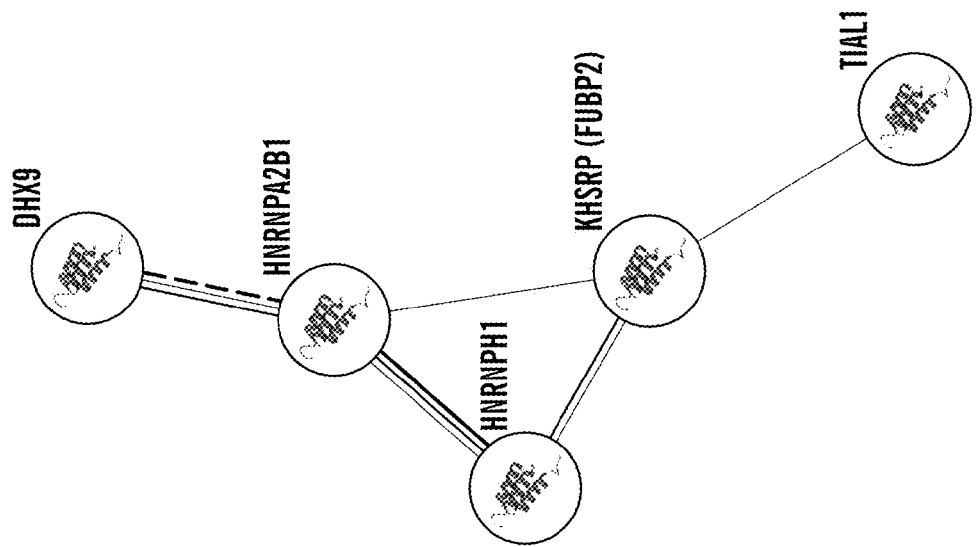
Figure 4C:
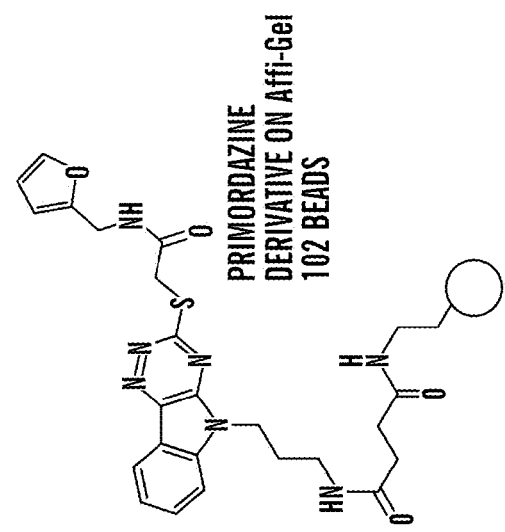

A primordazine derivative was synthesized in which an 8-atom linker was appended from the indole nitrogen, terminating in a carboxylic acid (FIG. 4B). This derivative with linker retained full PGC-ablating activity in zebrafish embryos, indicating that attachment of the linker does not interfere with the interaction between primordazine and its binding partners. The derivatized primordazine was then coupled to Affi-Gel 102 agarose beads, generating an affinity matrix (FIG. 4C). The affinity matrix was incubated with whole zebrafish lysates with and without competition from free primordazine, and iTRAQ was used to identify any primordazine-binding proteins. An RNA helicase, DHX9, was identified as binding specifically to the affinity matrix, along with two RNA-binding adapter proteins HNRNPH1 and HNRNPA2B1.

Using the STRING protein-protein association database (Szklarczyk, D. et al. The STRING database in 2011: functional interaction networks of proteins, globally integrated and scored. Nucleic Acids Res 39, D561-568 (2011)), network analysis was performed to compare the list of PRE-binding proteins with the primordazine-binding proteins. It was found that DHX9 and the adapter proteins HNRNPH1 and HNRNPA2B1 are known to interact with KHSRP and TIAL1 (FIG. 4D). Without wishing to be bound by a theory, it is believed that this finding explains the link between primordazine and the primordazine response element—primordazine binds DHX9, which binds to KHSRP and TIAL1, which bind to the PRE. Therefore, of the nine PRE-binding proteins, KHSRP and TIAL1 were prioritized for further investigation in this study because they are essential for PGC maintenance and because they interact with DHX9, HNRNPH1, and HNRNPA2B1. Further, DHX9 was prioritized as the primordazine binding protein for this study because the involvement of an RNA helicase in regulating nanos1 localization and translation appears to be a logical and testable hypothesis. While examples herein focus on KHSRP, TIAL1, and DHX9, other proteins can also be used.

Example 2

Determination of the Localization of KHSRP, TIAL1, and DHX9 in Germ Cells+/− Primordazine Treatment The cDNAs for khsrp, tial1 and dhx9 have been cloned into an expression vector that allows each protein to be expressed as a GFP fusion in germ cells. Germ cell specific expression is achieved by inclusion of the mir430 site in the 3' UTR of each mRNA. RNA encoding individual protein-GFP fusions is injected into 1-cell stage zebrafish. The localization of the protein-GFP fusion within the germ cells is determined by confocal microscopy at 6, 11, and 24 hpf. The effect of primordazine on localization is also determined by treating embryos with primordazine from 2-5 hpf and determining localization at 6, 11, and 24 hpf.

In addition to characterizing the localization of the three proteins within the germ cells of live zebrafish, localization of the proteins relative to nanos1 RNA localization is characterized. For these studies, animals are fixed at 6, 11, and 24 hpf and subjected to fluorescent in situ hybridization of the nanos1 gene. Nanos1 localization is visualized with a red marker (see FIG. 3 as an example), and the protein of interest is then be stained using anti-GFP immunofluorescence. In this way, nanos1 RNA localization can be visualized concurrently with localization of KHSRP, TIAL1, and DHX9 protein.

KHSRP and TIAL1 exhibit altered localization upon treatment with primordazine. Because these proteins bind the 3' UTR of nanos1, and because nanos1 localization changes from diffuse to punctate upon treatment with primordazine (see FIG. 3), the localization of KHSRP and TIAL1 also changes from diffuse to punctate. Visualisation of co-localization of nanos1 mRNA and the proteins of interest is interpreted as confirming an interaction between KHSRP or TIAL1 and the PRE in vivo. The protein and RNA can be co-localized before primordazine treatment, after primordazine treatment, or both. Co-localization after treatment might suggest that primordazine drives nanos1 RNA into RNA-protein granules containing KHSRP or TIAL1. Co-localization before primordazine treatment suggests that the proteins protect nanos1 RNA from granule incorporation. Co-localization before and after primordazine treatment suggests that the proteins are constitutively associated with nanos1 RNA, and that some additional protein modification or association regulates the relocalization of both protein and RNA.

Example 3

Quantify Binding of KHSRP and TIAL1 to the Primordazine Response Element in Vitro Both KHSRP and TIAL1 were identified by mass spectrometry after binding to a biotinylated PRE oligonucleotide. It is important to verify binding by an orthogonal technique and to quantify the effect of primordazine treatment on binding. The protein-GFP fusions described above are expressed in zebrafish embryos. Embryos are treated with primordazine or DMSO. Embryos are lysed, and biotinylated PRE oligonucleotides are added to the lysate. Magnetic streptavidin beads can be used to precipitate the PRE oligo and associated proteins, which are separated by SDS-PAGE and detected by anti-GFP western blot.

Binding of KHSRP and TIAL1 to the PRE is confirmed by western blot. Changes in binding upon treatment with primordazine are detected. This supports the fact that KHSRP or TIAL1 is functionally involved in the primordazine mechanism of action. When neither KHSRP nor TIAL1 exhibits altered binding to the PRE with primordazine treatment, it supports that primordazine does not alter binding of the proteins to the PRE but rather alters the localization and activity of the proteins in regulating nanos1 translation.

Example 4

Characterize the Effect of Primordazine on DHX9 Helicase Activity

The RNA helicase DHX9 was found by proteomic analysis to bind to the primordazine affinity matrix. This finding illustrates that primordazine functions by inhibiting the RNA helicase activity of DHX9. In such a model, DHX9 promotes the translation of nanos1 RNA by unwinding it. By inhibiting DHX9's helicase activity, primordazine prevents translation of nanos1 RNA and causes it to become incorporated in translationally repressed RNA-protein granules.

The effect of primordazine on DHX9 helicase activity is tested in an in vitro assay as previously described (Chakraborty, P. & Grosse, F. Human DHX9 helicase preferentially unwinds RNA-containing displacement loops (R-loops) and G-quadruplexes. *DNA Repair (Amst)* 10, 654-665 (2011)). Expression and purification of recombinant DHX9 in High Five cells are done using the baculovirus system. Double-stranded RNA substrate is generated by annealing synthetic RNA oligonucleotides and radiolabeled with T4 polynucleotide kinase and $^{33}$P-ATP. Helicase assays are performed by combining recombinant DHX9 and substrate+/−primordazine at half-log dilutions in 20 mM Tris-HCl, pH 7.5, 3.5 mM MgCl2, 3.5 mM ATP, 0.1 mg/ml BSA, 5 mM DTT and 10% (v/v) glycerol and incubating for 20 min at 37° C. Unwinding is terminated by rapid cooling on ice and by the addition of SDS loading buffer along with a 10-fold molar excess of unlabeled oligonucleotide to prevent reannealing of the unwound RNAs. The reaction products are separated by electrophoresis through nondenaturing polyacrylamide gels at 4 C., and quantified with a PhosphorImager.

Without wishing to be bound by a theory, it is believed that when primordazine exhibits dose dependent inhibition of DHX9 helicase activity and the IC50 is close to the effective concentration in zebrafish embryos (high nanomolar to low micromolar the primordazine inhibits nanos1 translation by inhibiting DHX9 helicase activity. Alternatively, when no effect of primordazine on DHX9 helicase activity is observed, it is believed that the helicase activity per se is not central to primordazine's mechanism of action.

Example 5

Determination of the Functions of KHSRP, TIAL1, and DHX9

Because of their strong and specific association with the primordazine response element (PRE), KHSRP and TIAL1 are good candidates for mediators of primordazine's effects on germ cells. Indeed, knockdown of either gene with morpholino oligonucleotides has a profound effect on PGC maintenance (see FIG. 6 for data for KHSRP). DHX9 is also an intriguing potential mediator of primordazine's effects because it binds to primordazine and also interacts with KHSRP and TIAL1. Therefore, all three genes were disrupted to assess the effects on nanos1 localization, translation, and on the maintenance of PGCs. Having developed an efficient pipeline for generating zinc finger nuclease (ZFN)- and TALEN-induced targeted mutations in zebrafish (oley, J. E. et al. Rapid mutation of endogenous zebrafish genes using zinc finger nucleases made by Oligomerized Pool ENgineering (OPEN). *PLoS ONE* 4, e4348 (2009); Foley, J. E. et al. Targeted mutagenesis in zebrafish using customized zinc-finger nucleases. *Nat Protoc* 4, 1855-1867 (2009); Sander, J. D. et al. Selection-free zinc-finger-nuclease engineering by context-dependent assembly (CoDA). *Nat Methods* 8, 67-69 (2011); Sander, J. D. et al. Targeted gene disruption in somatic zebrafish cells using engineered TALENs. *Nat Biotechnol* 29, 697-698 (2011)), an opportunity exists to generate true genetic knockouts for these genes. Genetic mutations is supplemented as needed by knockdowns via morpholino oligonucleotides. Knockout (or knockdown) fish are assessed for effects on nanos1 localization, translation, and PGC maintenance.

Successful Generation of Targeted Mutations in Zebrafish Using Zinc Finger Nucleases and TALENs Until recently, targeted mutation of genes in zebrafish was not possible. Recent demonstrations that zinc finger nucleases (ZFNs) and transcription activator-like effector nucleases (TALENs) can efficiently induce targeted mutations in zebrafish have opened up new experimental possibilities for the organism (Sander, J. D. et al. Targeted gene disruption in somatic zebrafish cells using engineered TALENs. *Nat Biotechnol* 29, 697-698 (2011); Meng, X., Noyes, M. B., Zhu, L. J., Lawson, N. D. & Wolfe, S. A. Targeted gene inactivation in zebrafish using engineered zinc-finger nucleases. *Nat Biotechnol* 26, 695-701 (2008); Doyon, Y. et al. Heritable targeted gene disruption in zebrafish using designed zinc-finger nucleases. *Nat Biotechnol* 26, 702-708 (2008).) New technologies for targeted manipulation of the zebrafish genome have been developed (Foley, J. E. et al. Rapid mutation of endogenous zebrafish genes using zinc finger nucleases made by Oligomerized Pool ENgineering (OPEN). *PLoS ONE* 4, e4348 (2009); Foley, J. E. et al. Targeted mutagenesis in zebrafish using customized zinc-finger nucleases. *Nat Protoc* 4, 1855-1867 (2009); Sander, J. D. et al. Selection-free zinc-finger-nuclease engineering by context-dependent assembly (CoDA). *Nat Methods* 8, 67-69 (2011)). Using these technologies, targeted mutations in more than 30 zebrafish genes were created during the past 3+ years.

Mutation of khsrp, tial1, and dhx9.

Pairs of TALENs targeting khsrp and tial1 were designed and assembled. These TALEN pairs were injected into one-cell stage zebrafish embryos, and their efficiency was determined by assessing the somatic mutation rate in the embryos after 48 hours of development. For khsrp, the somatic mutation rate was approximately 4% (1/26 sequences analyzed), and for tial1, the somatic mutation rate was approximately 76% (29/38 sequences analyzed, see FIG. 5). Therefore, both TALEN pairs were active and capable of generating mutations at an acceptable rate. Based on these results, one can successfully identify mutant founders for khsrp and tial1. Accordingly, injected animals can be raised to sexual maturity and are screened for founder identification. A similar process was followed for dhx9 as described below.

khsrp Knockdown Phenocopies Treatment with Primordazine.

Figure 6A:
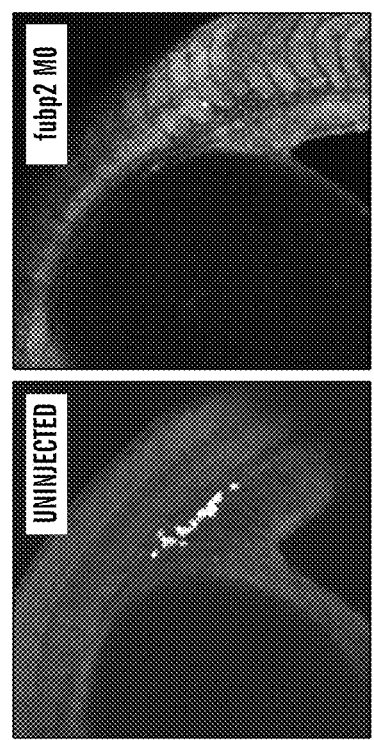
FIGS. 6A-6B illustrate KHSRP knockdown phenocopies treatment with primordazine.
Figure 6B:
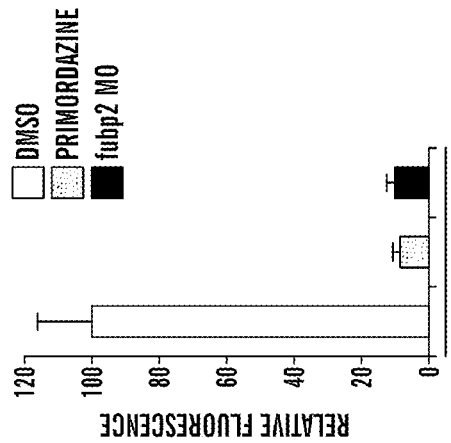

While generating mutations in khsrp, tial1, and dhx9 genes, which required several months of work, khsrp and tial1 were tested by a more rapid, parallel approach. Morpholino oligonucleotides (MOs) were used to knock down expression of khsrp in zebrafish. It was found that khsrp-MO-injected zebrafish exhibited a reduction in PGCs (FIG. 6A). In a quantitative assay, khsrp MO or a control MO with mRNA encoding GFP were co-injected followed by the nanos1 3' UTR. It was found that knockdown of khsrp stabilized GFP RNA while simultaneously reducing translation of GFP protein. This effect was indistinguishable from the effect of primordazine treatment (FIG. 6B). This shows that KHSRP plays a role in PGC maintenance while regulating mRNA translation through the nanos1 3' UTR. It was also found that knockdown of TIAL1 caused a loss of PGCs (data not shown).

Example 6

Complete Targeted Mutation of khsrp, tial1, and dhx9

An efficient pipeline for creating targeted mutations was established. In brief, the process includes:

1) TALEN design. TALEN pairs are designed using ZiFiT 4.0 software (http://zifit.partners.org/ZiFiTBeta/Introduction.aspx). The first exon in each gene is targeted, maximizing the possibility that mutations generated are null.

2) TALEN construction. TALENs are constructed using the FLASH method as previously described[22].

3) mRNA synthesis. This is performed using standard mMESSAGE RNA synthesis kits.

4) mRNA injection. Performed at the one-cell stage with an Eppendorf microinjector.

5) determination of somatic mutation rate. Injected embryos are pooled, genomic DNA is collected, and the target site is amplified by PCR and TOPO cloned. 96 individual clones are sequenced.

6) founder identification. Injected animals are grown to maturity and out-crossed. Offspring are genotyped for the presence of mutations at the target site.

The success rate with TALENs has been 100% so far. Targeted mutations in all 13 genes that were targeted with TALENs were generated, although in some cases a second pair of TALENs was designed to a particular gene to achieve successful mutation. Founders for all three genes targeted were identified. For genes that fail to be mutated on the first attempt, it is necessary to design a second pair of TALENs at a different site, but mutations are usually to be generated on the first or second attempt.

Example 7

Test Mutants for Defects in RNA Localization, Translation, and PGC Maintenance

Figure 2B:
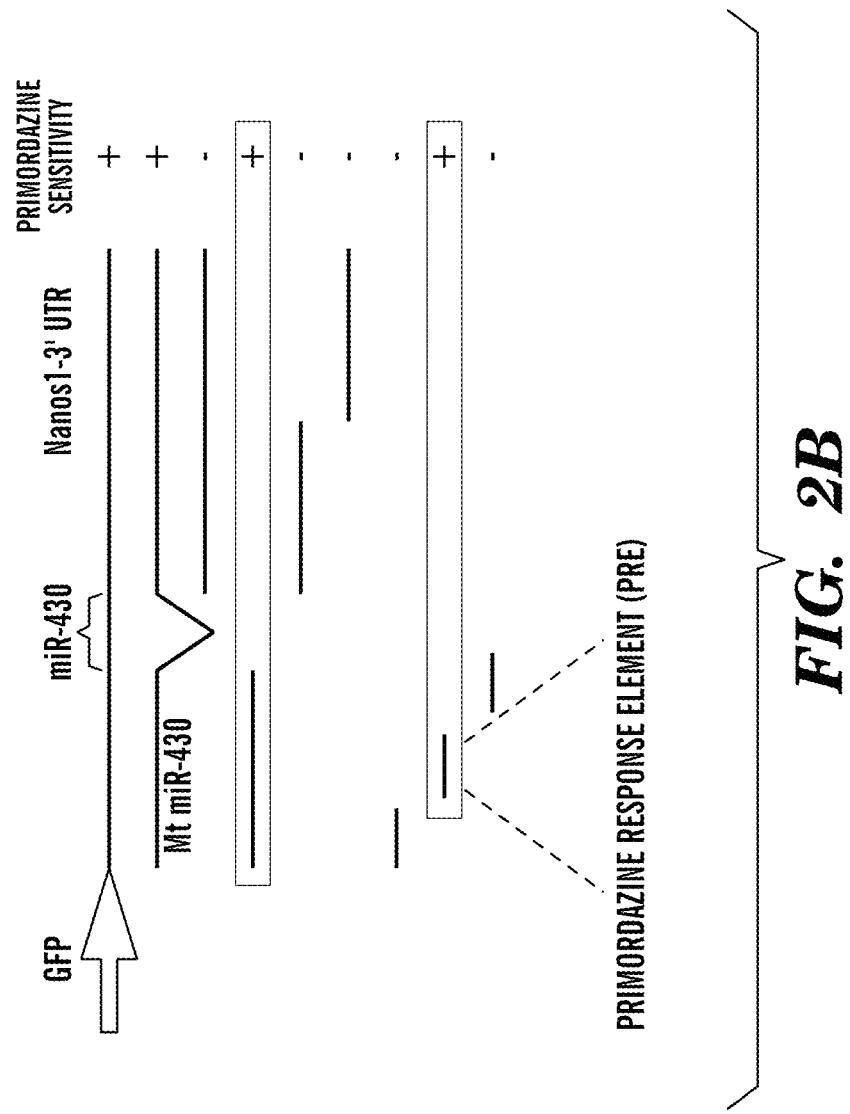

Once the function of a protein has been disrupted, the effect of disruption on nanos1 RNA localization, translation of a GFP reporter, and maintenance of PGCs was determined. Both homozygous mutants and the offspring of homozygous mothers are tested, since maternal effects are also possible.

nanos1 mRNA localization is tested by fluorescent in situ hybridization using the method shown in FIG. 3 and previously published (Machluf, Y. & Levkowitz, G. Visualization of mRNA expression in the zebrafish embryo. *Methods Mol Biol* 714, 83-102 (2011)). Both untreated and primordazine-treated mutant animals are stained for endogenous nanos1 expression pattern in primordial germ cells at 6, 11, and 24 hours postfertilization (hpf). Expression patterns are determined by confocal microscopy using Zeiss LSM700. In untreated mutants, a change relative to the diffuse, wild-type expression pattern was of particular interest (FIG. 3). In primordazine-treated mutants, a change relative to the punctate pattern seen in wild-type, primordazine-treated animals was of particular interest (FIG. 3).

mRNA translation is tested using the same GFP reporter depicted in FIG. 2. This reporter consists of GFP mRNA fused to the nanos1 3' UTR with a mutant miR-430 site. When injected into one-cell stage zebrafish, GFP is expressed in both germ and somatic cells (Giraldez, A. J. et al. Zebrafish MiR-430 promotes deadenylation and clearance of maternal mRNAs. *Science* 312, 75-79 (2006); Mishima, Y. et al. Differential regulation of germline mRNAs in soma and germ cells by zebrafish miR-430. *Curr Biol* 16, 2135-2142 (2006)). Primordazine stabilizes the mRNA but prevents its translation. As such, the quantity of mRNA is increased as detected by qPCR, but the quantity of GFP protein diminishes, as determined by quantitative fluorescence microscopy (see FIG. 2 for an example). Mutant animals were injected with the GFP reporter mRNA and quantify the amount of mRNA and protein present at 11 and 24 hours. Attention was paid to the effects of the mutations on baseline translation of GFP and also for effects of the mutations on responsiveness to primordazine.

PGC maintenance is determined by performing in situ hybridizations with PGC markers vasa, nanos1, and deadend in wild-type and mutant animals at 24 hours postfertilization. Experiments are performed as shown in FIGS. 1A-1B and published previously (Machluf, Y. & Levkowitz, G. Visualization of mRNA expression in the zebrafish embryo. *Methods Mol Biol* 714, 83-102 (2011). A decrease in PGC numbers in mutant animals was of particular interest. It was also determined if the mutation prevents primordazine from ablating PGCs.

Disruption of KHSRP, TIAL1, and DHX9 alters nanos1 mRNA localization, translation, or PGC maintenance. Changes in baseline localization, translation, or PGC number, illustrate that the proteins are involved in normal PGC development and maintenance. Changes in the ability of primordazine to ablate PGCs without affecting baseline levels, illustrate that the protein is involved in primordazine's mechanism of action but may not contribute to normal PGC biology. Changes in both baseline and primordazine-induced states, illustrate involvement of the protein in both normal and primordazine-induced functions.

Example 8

Discovery of Additional RNAs Regulated by Primordazine

Preliminary evidence suggests that the mechanisms that regulate nanos1 localization and translation are not restricted to nanos1. It is known, for example, that the mechanisms are active in most cells, not just germ cells. When the miR-430 site is mutated in the nanos1 3' UTR, its accompanying message is translated throughout all somatic cells, and primordazine can block translation in these somatic cells. Hence, the regulatory machinery is present in cells beyond germ cells and is regulating other RNAs, in addition to nanos1. Other RNAs regulated by primordazine were sought.

Germ cells are an obvious place to look for RNAs that are regulated at a post-transcriptional level because much of the early germ cell biology occurs before the onset of zygotic transcription. Neurons are another interesting cell type in which to look for post-transcriptional regulation of RNAs. Many neurons possess multiple axons and dendrites, and there is evidence that a single neuron can selectively control protein translation at different synapses by regulating the localization and translation of RNAs at specific axons (Holt, C. E. & Bullock, S. L. Subcellular mRNA localization in animal cells and why it matters. *Science* 326, 1212-1216 (2009); Swanger, S. A. & Bassell, G. J. Making and breaking synapses through local mRNA regulation. *Curr Opin Genet*

Dev (2011); Loya, C. M., Van Vactor, D. & Fulga, T. A. Understanding neuronal connectivity through the post-transcriptional toolkit. *Genes Dev* 24, 625-635 (2010).). This capability appears to be central to the function of neurons, and it is interesting to note that many of the genetic mutations that have been associated with neurodegenerative and other nervous system disorders lie in RNA binding proteins (Orr, H. T. RNA gains a new function: a mediator of neurodegeneration. *Trends Neurosci* 27, 233-234 (2004); Ticozzi, N., Ratti, A. & Silani, V. Protein aggregation and defective RNA metabolism as mechanisms for motor neuron damage. *CNS Neurol Disord Drug Targets* 9, 285-296 (2010); Lagier-Tourenne, C., Polymenidou, M. & Cleveland, D. W. TDP-43 and FUS/TLS: emerging roles in RNA processing and neurodegeneration. *Hum Mol Genet* 19, R46-64 (2010)). Therefore, in addition to identifying RNAs that are regulated by primordazine in germ cells, it was investigated to determine if RNAs are similarly regulated in neurons.

Two complementary experimental approaches are used to identifying RNAs that are regulated by primordazine. The first uses RNA sequencing (RNA-seq) to examine the set of RNAs that is being actively translated (present in polysomes) with and without primordazine treatment. This experiment has the potential to find all RNAs that are regulated at the translational level by primordazine-sensitive pathways. The second approach uses in vivo biotinylation to purify KHSRP and TIAL1 along with their associated RNAs. Again, RNA-seq can identify individual RNAs and quantify the effects of primordazine treatment.

Purify Polysomes and Quantify Changes in Actively Translated mRNA by RNA Sequencing.

Association of an mRNA with ribosomal polysomes is generally viewed as an indicator that the mRNA is being actively translated. Therefore, there is a subset of mRNAs whose interaction with polysomes is altered by primordazine treatment. To identify this subset of mRNAs, polysomes were purify from untreated and primordazine-treated zebrafish and compare the associated mRNAs by RNA-seq. This experiment is done as follows:

1) mass matings. Large-scale matings of wild-type zebrafish generate >10,000 synchronized zebrafish embryos.

2) primordazine treatment. Half of the embryos are treated with primordazine from 2-6 hpf; the other half are treated with DMSO.

3) deyolking. At 6 hours postfertilization, embryos are crushed by gentle pressure with mortar and pestle in Ringer's buffer on ice. Cells are rinsed and pelleted several times to remove yolk and chorions.

4) cell lysis. Cells are lysed in Triton-X buffer containing cycloheximide, protease and phosphatase inhibitors as described (Masek, T., Valasek, L. & Pospisek, M. Polysome analysis and RNA purification from sucrose gradients. *Methods Mol Biol* 703, 293-309 (2011); Melamed, D. & Arava, Y. Genome-wide analysis of mRNA polysomal profiles with spotted DNA microarrays. *Methods Enzymol* 431, 177-201 (2007)). Lysates are clarified by centrifugation.

5) polysome purification and RNA extraction. Polysomes are purified by ultracentrifugation on a sucrose gradient as described (Masek, T., Valasek, L. & Pospisek, M. Polysome analysis and RNA purification from sucrose gradients. *Methods Mol Biol* 703, 293-309 (2011). Melamed, D. & Arava, Y. Genome-wide analysis of mRNA polysomal profiles with spotted DNA microarrays. *Methods Enzymol* 431, 177-201 (2007)). RNA is extracted from polysome preps using the Trizol method.

6) library construction, sequencing, and analysis. The dUTP method is used for strand-specific RNA sequencing (Parkhomchuk, D. et al. Transcriptome analysis by strand-specific sequencing of complementary DNA. *Nucleic Acids Res* 37, e123 (2009)). This method is preferred by the Broad Institute Genome Sequencing Platform, where the RNA-seq is performed, because comparison of the seven leading RNA-seq methods showed that the dUTP method performs best as measured by strand specificity, library complexity, and continuity and evenness of coverage (Levin, J. Z. et al. Comprehensive comparative analysis of strand-specific RNA sequencing methods. *Nat Methods* 7, 709-715 (2010)). The method is also performed as previously described (Parkhomchuk, D. et al. Transcriptome analysis by strand-specific sequencing of complementary DNA. *Nucleic Acids Res* 37, e123 (2009); Levin, J. Z. et al. Comprehensive comparative analysis of strand-specific RNA sequencing methods. *Nat Methods* 7, 709-715 (2010)). Briefly, RNA is fragmented by heating in sodium citrate solution. 200 ng of RNA is primed with random hexamers and first strand synthesis is performed with SuperScript III, SUPERase-In, and actinomycin D. First strand is cleaned up by extraction/precipitation, followed by second strand synthesis with dTTP replaced by dUTP. Paired-end libraries are prepared for Illumina sequencing according to manufacturer instructions. Sequencing is performed on an Illumina Genome Analyzer II, with standard sequencing primers and 76 base reads. Data analysis is performed using Trinity, a suite of RNA-seq analysis tools developed by the Broad Institute Genome Sequencing Platform (Grabherr, M. G. et al. Full-length transcriptome assembly from RNA-Seq data without a reference genome. *Nat Biotechnol* (2011)).

The majority of mRNAs is not affected by primordazine treatment and is therefore equally represented in polysome fractions from untreated and primordazine-treated embryos. Primordazine-treated animals have few overt developmental defects outside the germline, suggesting that primordazine does not cause general translation blockade. Therefore, housekeeping genes and other genes not regulated by primordazine are found equally in polysomes from untreated and primordazine-treated animals. In contrast, nanos1 mRNA is changed in its localization and translation by primordazine treatment and therefore is present at higher levels in untreated polysomes than in primordazine-treated polysomes. Most importantly, a subset of mRNAs was identify that, like nanos1, are altered in their translation by primordazine treatment. These mRNAs are over- or under-represented in primordazine-treated polysomes.

Purify KHSRP and TIAL1 and Identify the Associated RNAs.

It is known from proteomic experiments that KHSRP and TIAL1 bind to the nanos1 primordazine response element and not to the control sequences that have been tested. It is desirable to know what other RNAs, beyond nanos1, are bound specifically by these proteins. To identify associated RNAs, an in vivo biotinylation technique was used to selectively biotinylate KHSRP and TIAL1 in germ cells and neurons. Streptavidin beads are then used to purify each protein and its associated RNAs from the tissue of interest. RNAs are be identified by RNA-seq.

The technique employs a bacterial biotin-protein ligase called BirA to biotinylate the target protein in vivo (Cull, M. G. & Schatz, P. J. Biotinylation of proteins in vivo and in vitro using small peptide tags. *Methods Enzymol* 326, 430-440 (2000); de Boer, E. et al. Efficient biotinylation and single-step purification of tagged transcription factors in mammalian cells and transgenic mice. *Proc Natl Acad Sci*

Figure 7:
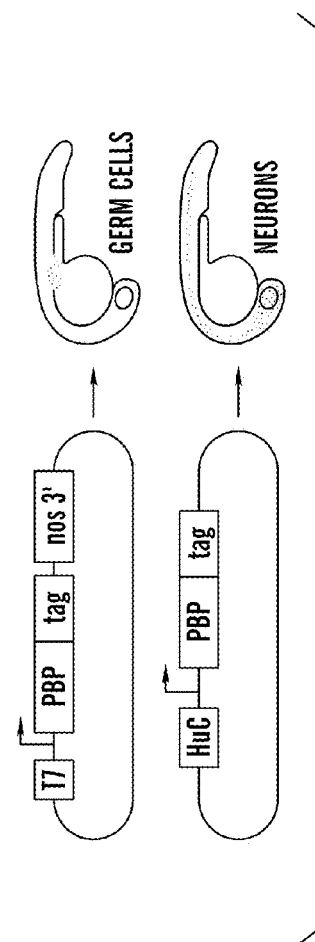
FIG. 7 illustrates the constructs for tissue-specific expression of biotin-tagged proteins. For germ cell expression, RNA is transcribed in vitro using T7 and co-injected with BirA RNA. The nanos1 3' UTR (nos 3') directs expression to germ cells. For neuronal expression, the plasmid is injected along with BirA plasmid. The HuC promoter directs pan-neuronal expression. Ubiquitous expression is achieved by injection of mRNA.
Figure 8:
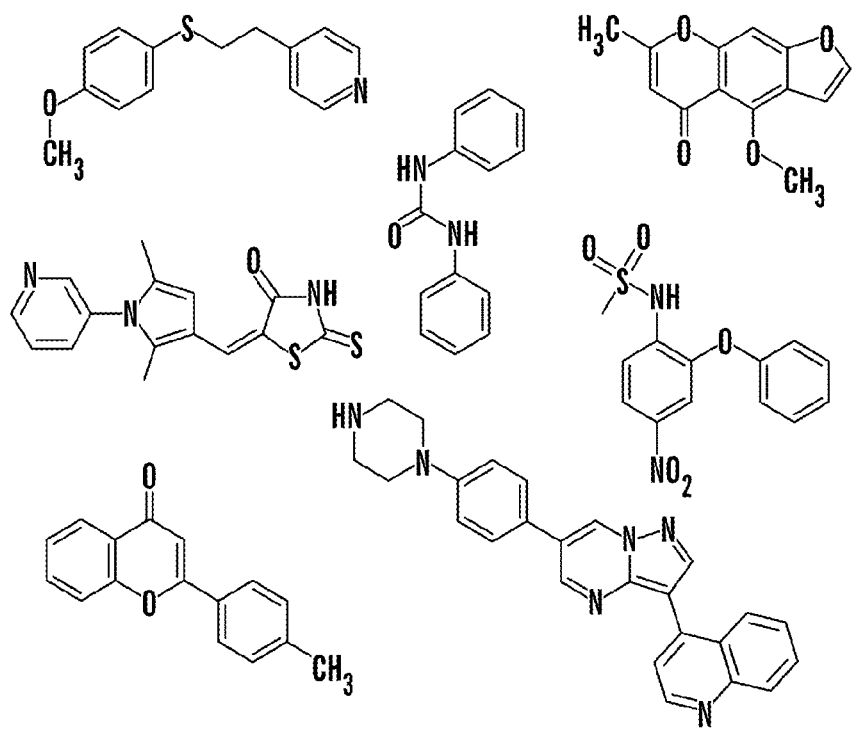
FIG. 8 illustrates examples of compounds used in a chemical screen for PGC small modifiers in zebrafish.
Figure 9:
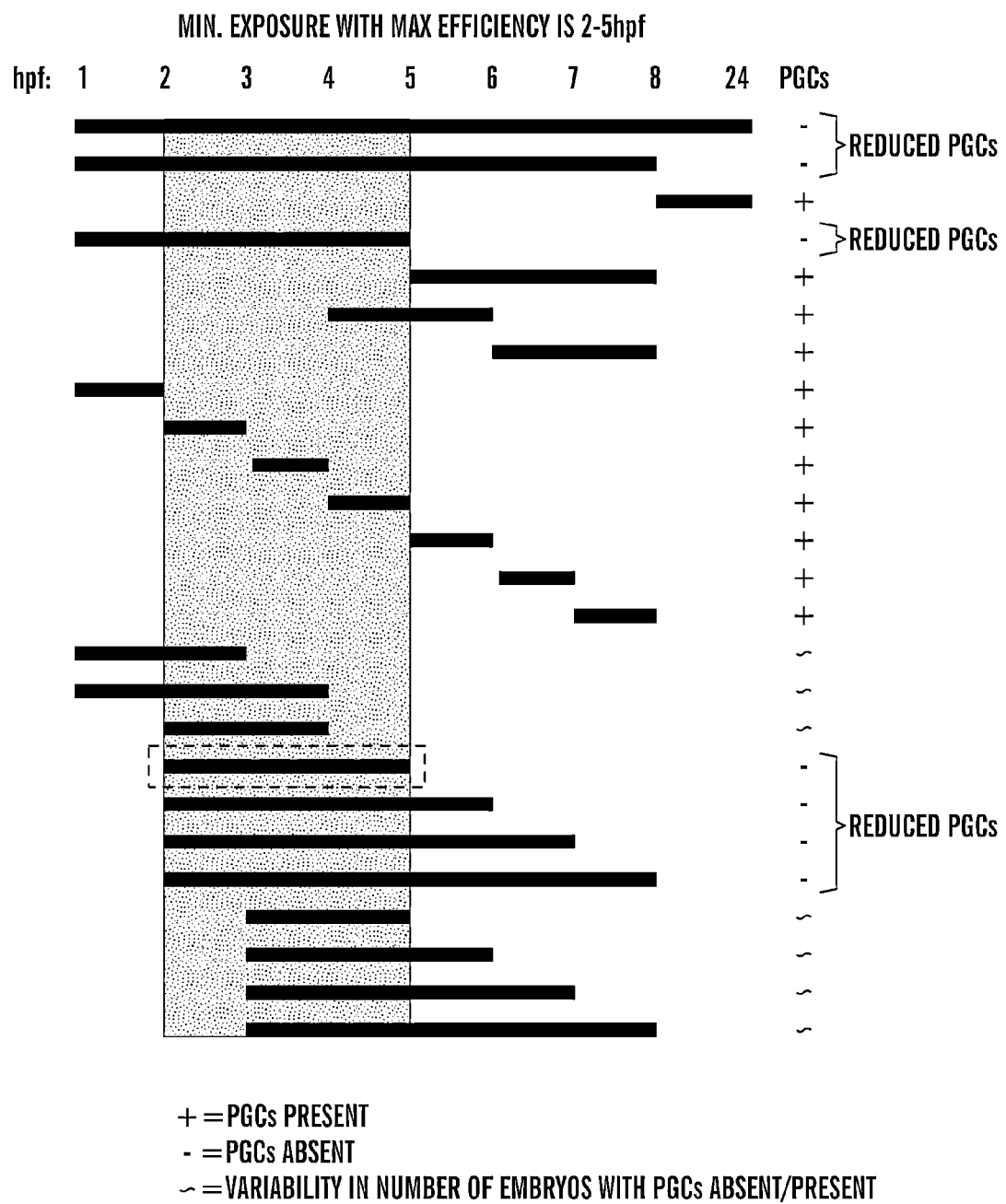
FIG. 9 illustrates that primordazine is effective only around the mid-blastula transition.
Figure 10:
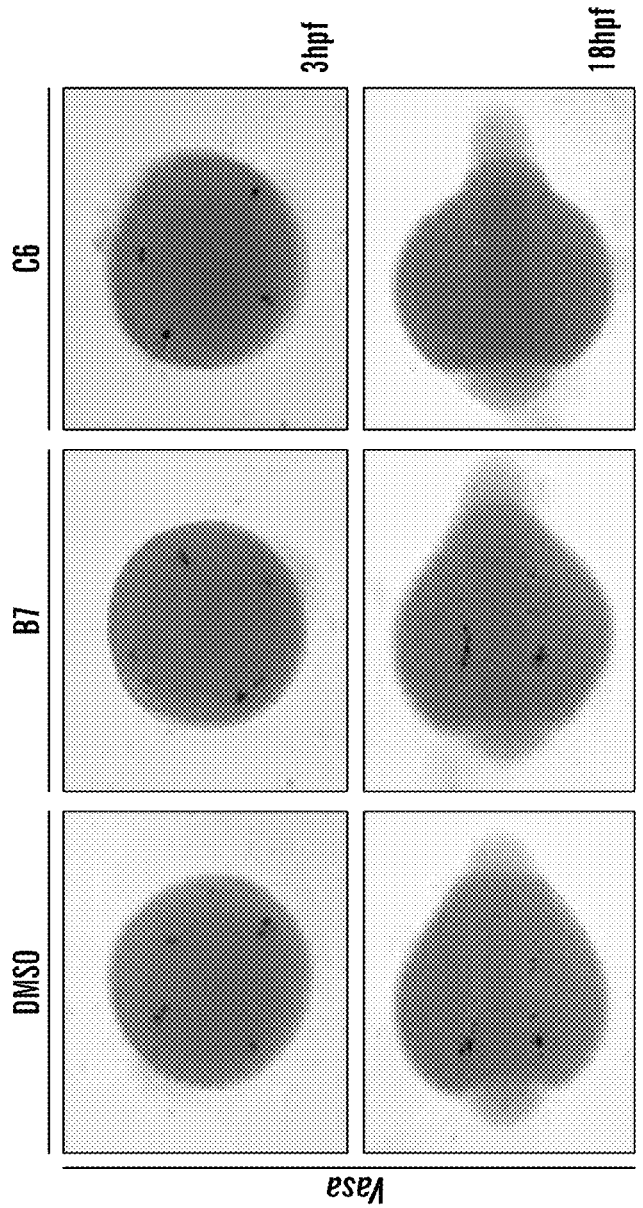
FIG. 10 illustrates that primordazine affects PGC permanence, not specification or migration.
Figure 11:
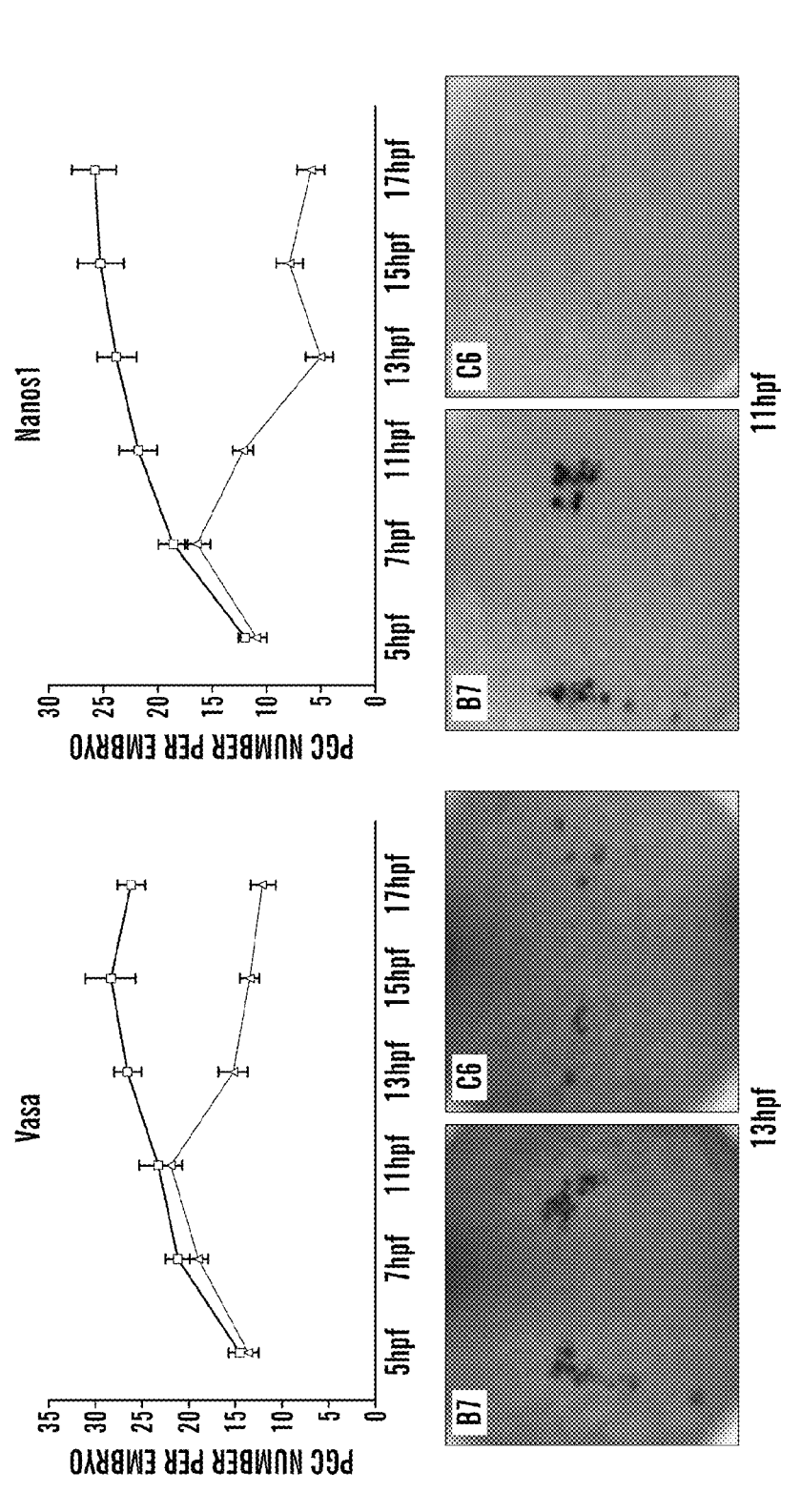
FIG. 11 illustrates that nanos loss precedes vasa loss. Based on vasa and nanos1 transcript expression, C6 reduces PGC number after 7 hpf.
Figure 12:
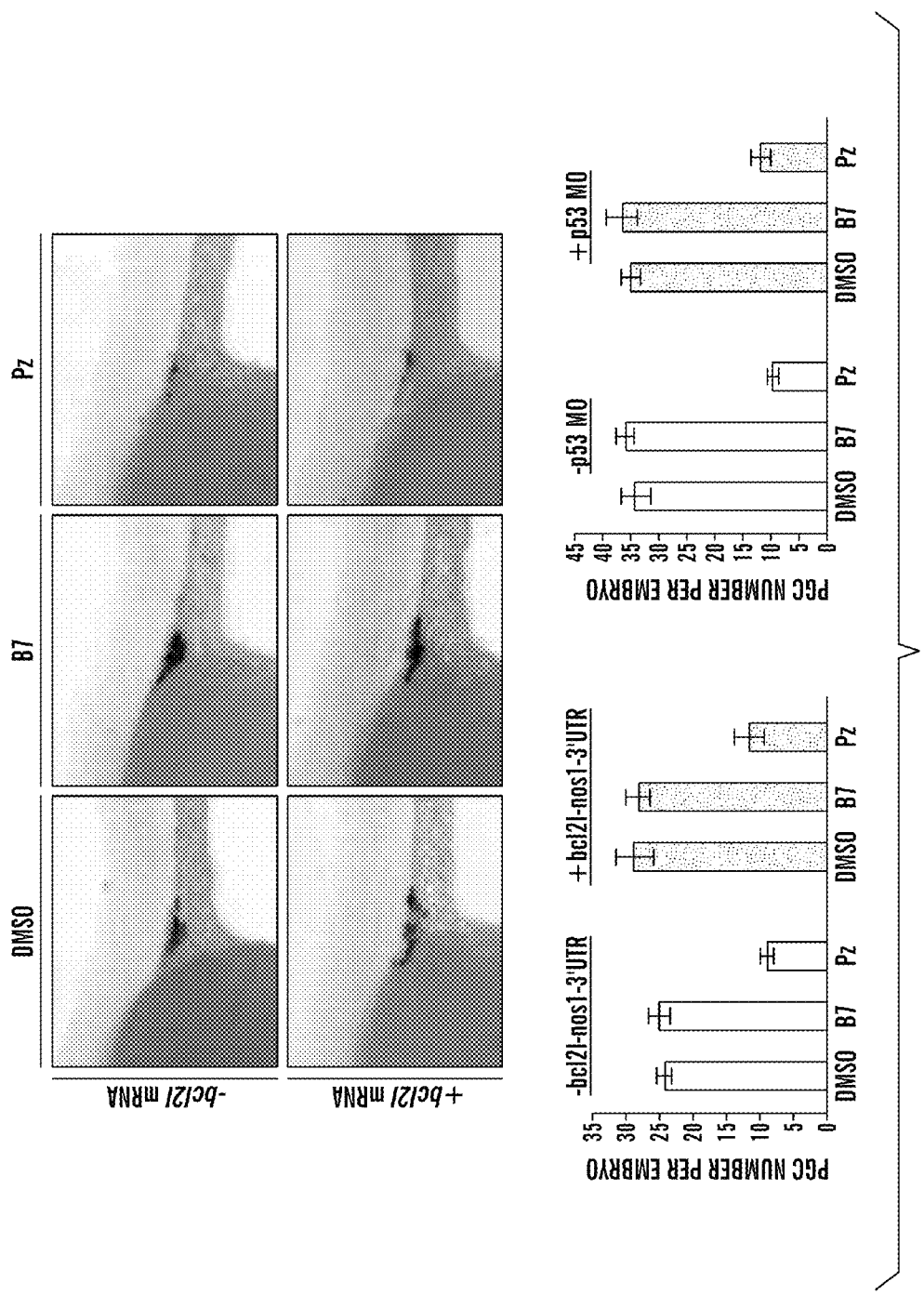
FIG. 12 illustrates that primordazine does not cause apoptosis.
Figure 13:
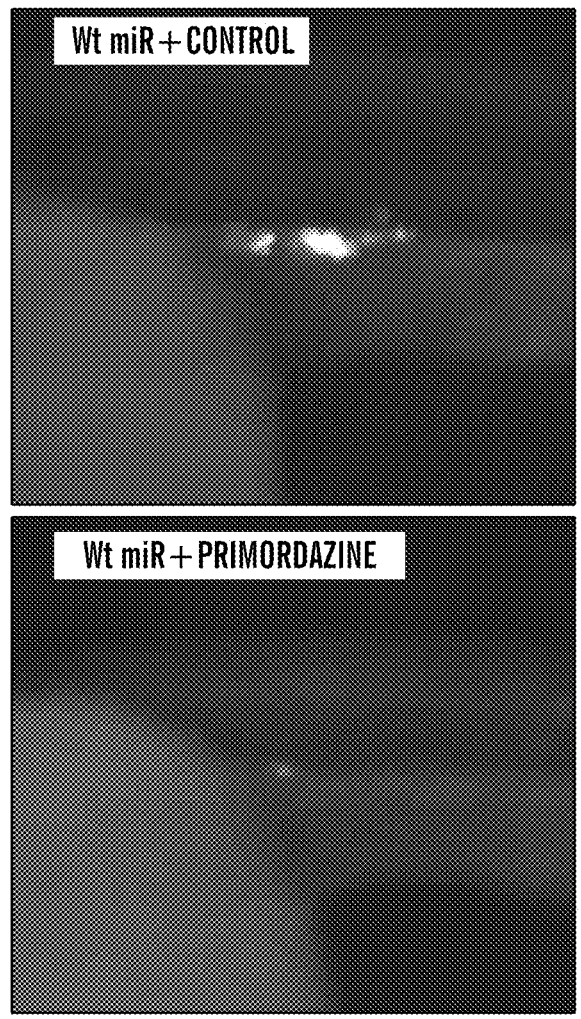
FIG. 13 illustrates that primordazine functions through the nanos1 3' UTR.

USA 100, 7480-7485 (2003)). BirA recognizes and specifically biotinylates a 15 amino acid biotinylation tag. Each protein are subcloned into an expression vector that enables tissue-specific expression of the protein fused to a 15 amino acid biotinylation tag (see FIG. 7). Co-expression with BirA results in in vivo biotinylation of the protein (Cull, M. G. & Schatz, P. J. Biotinylation of proteins in vivo and in vitro using small peptide tags. *Methods Enzymol* 326, 430-440 (2000); de Boer, E. et al. Efficient biotinylation and single-step purification of tagged transcription factors in mammalian cells and transgenic mice. *Proc Natl Acad Sci USA* 100, 7480-7485 (2003)). Once biotinylated, the protein are purified with high efficiency and specificity using streptavidin beads.

The two proteins (KHSRP and TIAL1) are purified from three different cell populations (PGCs, neurons, and all cells), for a total of 6 different experiments. For each experiment, untreated and primordazine-treated embryos are compared. Neuronal expressions are driven from the HuC promoter (Park, H. C. et al. Analysis of upstream elements in the HuC promoter leads to the establishment of transgenic zebrafish with fluorescent neurons. *Dev Biol* 227, 279-293 (2000)), and germ cell-restricted expression are achieved using the nanos1 3' UTR (Mishima, Y. et al. Differential regulation of germline mRNAs in soma and germ cells by zebrafish miR-430. *Curr Biol* 16, 2135-2142 (2006)), and ubiquitous expression are achieved by injecting mRNA.

There are several advantages to this approach. First, the use of biotin-streptavidin for protein purification is efficient, specific, and reproducible, eliminating the artifacts that are common for most antibodies. Second, by expressing the biotinylated proteins in a tissue-specific manner, the associated RNAs that are unique to that cell type can be identified.

The experiment proceeds as follows:

1) tissue-specific expression of tagged proteins. DNA (for neuronal expression) or RNA (for germ cell expression or ubiquitous expression) encoding each tagged protein is injected into 1000 wild-type embryos along with DNA or RNA encoding BirA.

2) primordazine treatment. For germ cell experiments, half of the embryos are treated with primordazine from 2-6 hpf; the other half are treated with DMSO. For neuronal and ubiquitous expression experiments, embryos are treated from 24-28 hpf.

3) deyolking. At 6 hours postfertilization (for germ cell experiments) or 28 hpf (for neuron and ubiquitous experiments), embryos are crushed by gentle pressure with mortar and pestle in Ringer's buffer on ice. Trypsin is added as needed for 28 hpf animals. Cells are rinsed and pelleted several times to remove yolk and chorions, then filtered through a 40 micron mesh.

4) cell lysis. Cells are lysed in Triton-X buffer containing protease and phosphatase inhibitors. Lysates are clarified by centrifugation.

5) protein purification and RNA extraction. Target proteins are purified using magnetic streptavidin beads. RNA is extracted from the protein-RNA complexes using the Trizol method.

6) library construction, sequencing, and analysis. Library construction, sequencing, and analysis proceed as described above except that barcoding is used to enable multiplexing of samples to reduce the number of lanes required for sequencing.

The experiments outlined above provide a vast and rich source of data that can be mined in several ways. The data enable us to gain the following kinds of insights:

Sequence selectivity. By comparing all of the RNA sequences bound to a particular protein, the sequence preference of that protein can be ascertained.

Primordazine selectivity. By comparing treated and untreated embryos, it can be determined if primordazine's effects are selective for nanos1 or affect other pathways.

Tissue selectivity. By comparing RNAs from germ cells, neurons, and all cells, it can be determined if primordazine-sensitive mechanisms are active in cells outside of the germline.

Selectivity overlap. By comparing RNAs associated with KHSRP and TIAL1, it can be determined the extent to which the two proteins have overlapping and distinct functions.

Example 9

Nanos 3' UTR can Target PFCs Specific Expression in Heterologous Species

Figures 23, 24:
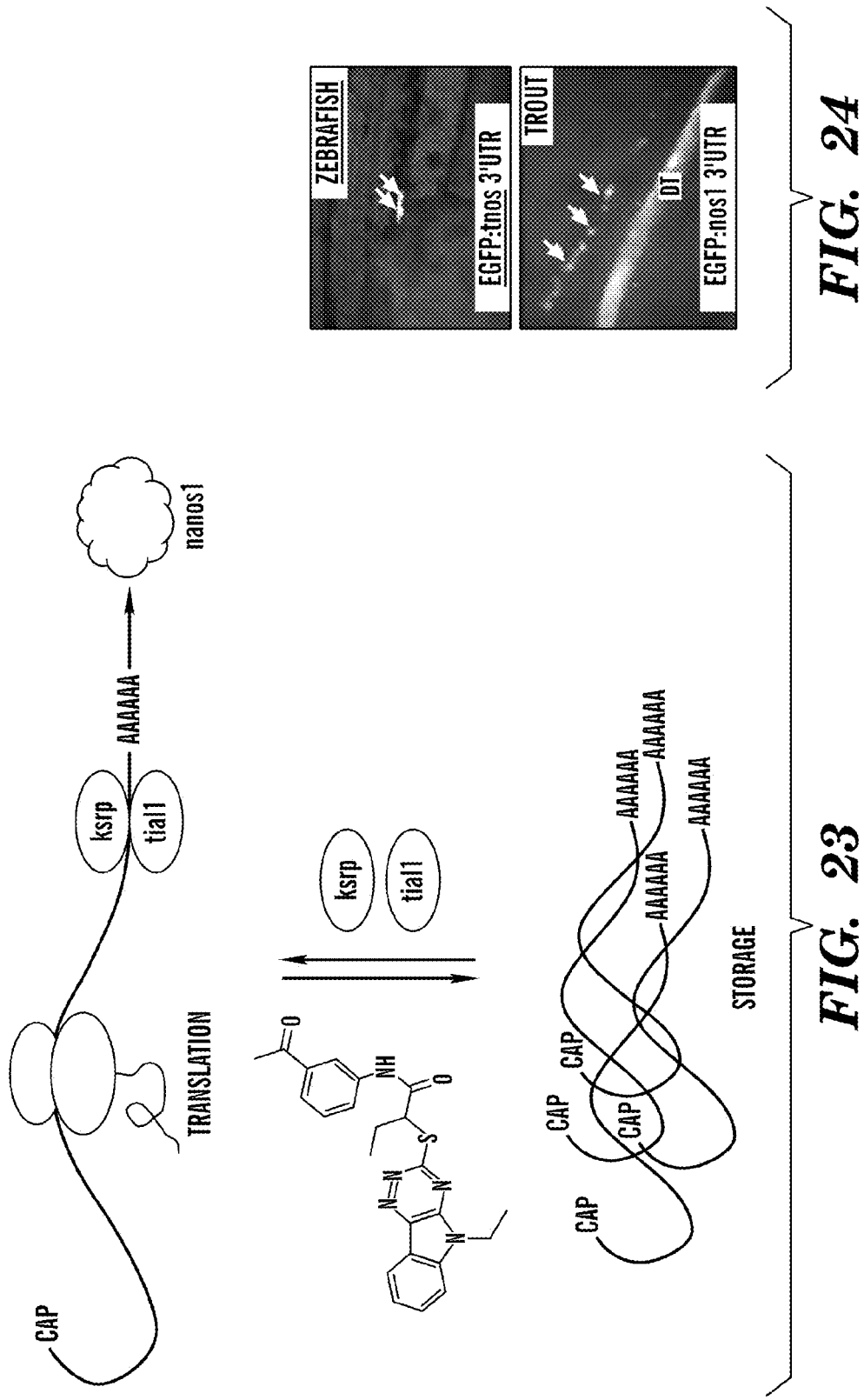
FIG. 23 illustrates a model of nanos1 regulation.
FIG. 24 is a set of fluorescent images of zebrafish embryos (48 hpf) injected with 60 pg of synthetic capped RNA eGFP:tnanos 3'UTR (tnanos: from tilapia nanos gene) and trout embryos (30 dpf) injected with 200 pg of synthetic capped RNA eGFP:nanos1 3'UTR (from zebrafish nanos1 gene). Arrows indicate GFP-PGCs in dorsal position relative to the digestive tract (DT) showing auto-fluorescence.

Synthetic capped eGFP:nanos1 3'UTR mRNA was microinjected into both trout and salmon embryos and eGFP:tnanos 3'UTR mRNA (tnanos 3'UTR from tilapia nanos gene) into zebrafish embryos and observed GFP expression exclusively in PGCs of RNA treated fish (FIG. 24). This result mirrors other studies addressing the relationship between phylogenetic distance and functionality of the 3'UTR of germ cell specific genes. For example, the 3'UTR of zebrafish nos1 gene also directed PGC GFP expression in herring, medaka and ice goby, which belong to Clupeinformes, Beloniformes, and Perciformes respectively (Saito et al., The International Journal of Developmental Biology 2006, 50, 691). The evolutionarily conserved nature of the machinery responsible for germ cell mRNA translation within PGCs makes this PRE pathway particularly attractive for the development of inhibitors, and should allow application of primordazine to a broad range of host target species.

Example 10

Optimization of Primordazine Derivatives and Mode of Action of Primordazine

Primordazine ablates germ cells in a dose-dependent manner, with maximal efficacy achieved at egg water concentrations of 6 uM. Although this dose is reasonably low for an un-optimized screening hit, there are reasons to believe that more potent derivatives of primordazine can be developed. Typically, primary hits from small molecule screens can be optimized by medicinal chemistry to be orders of magnitude more potent and selective. For example, using medicinal chemistry, derivatives of dorsomorphin exhibiting high potency (IC50=5 nM) were previously developed with dramatically improved selectivity (Cuny et al., Bioorg Med Chem Lett 2008, 18, 4388-4392; Yu et al., Nat Chem Biol 2008, 4, 33-41). In the case of primordazine, developing derivatives with improved potency and selectivity can provide many practical benefits, such as limiting the amount of compound required to ablate germ cells and minimizing unwanted effects of the compound on the developing fish. Therefore, it is desirable to identify primordazine derivatives that ablate germs cells at concentrations 10-100 times lower than those required for primordazine.

The process of medicinal chemistry optimization goes beyond trial and error to ask specific questions about the relationship between a compound's structural features and its activity. Working in iterative cycles, specific structural features of primordazine can be interrogated by designing, acquiring, and testing small groups of compounds that incorporate chemical modifications to that feature. The effects of those changes can point to further modifications that should be investigated, leading to another cycle of design, acquisition, and testing. The final outcome, after several cycles of investigation, is typically a group of highly optimized compounds with the desired characteristics. Although there are multiple compound attributes that one might wish to incorporate into the final optimized structures (e.g. low toxicity), potency should be focused on at the beginning. Each derivative designed and acquired can be tested for its effect on PGCs, as described below. As potency is optimized, toxicity is another concern. Compounds that ablate PGCs but also have low toxicity even at elevated doses are given preference. Optimization can proceed through iterative rounds of compound design, acquisition, and testing as follows:

(1). Compound Design.

Figure 25:
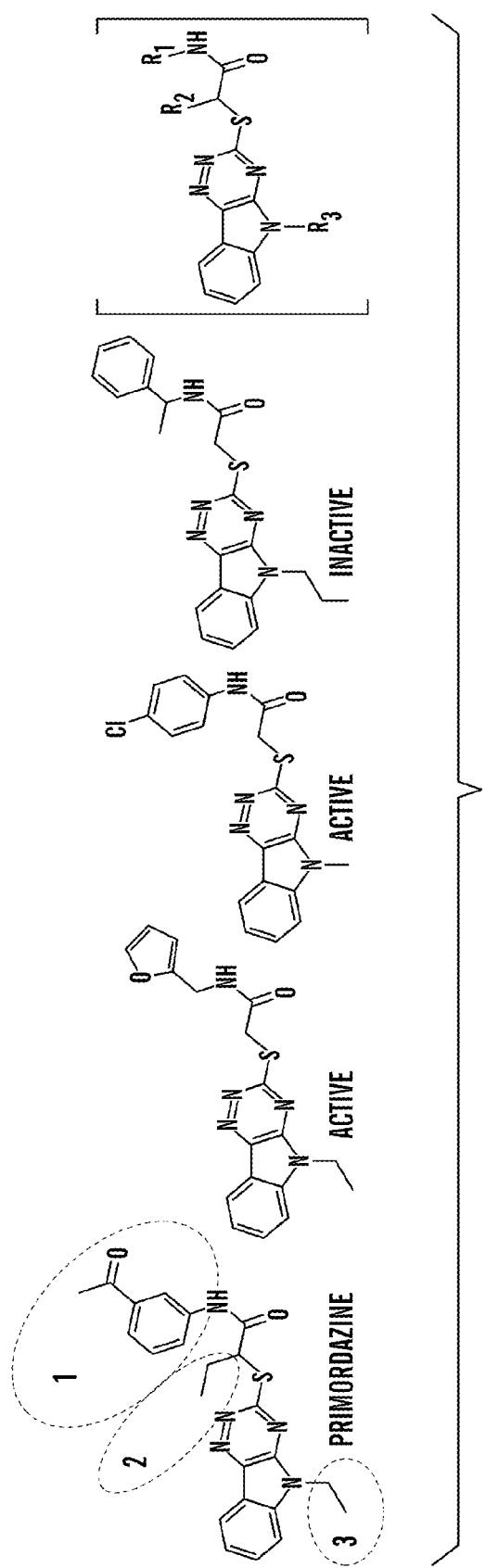
FIG. 25 shows structures of primordazine and related molecules. Numbered ovals indicate the three regions that will receive initial focus for structure-activity relationship studies.
Figure 26:
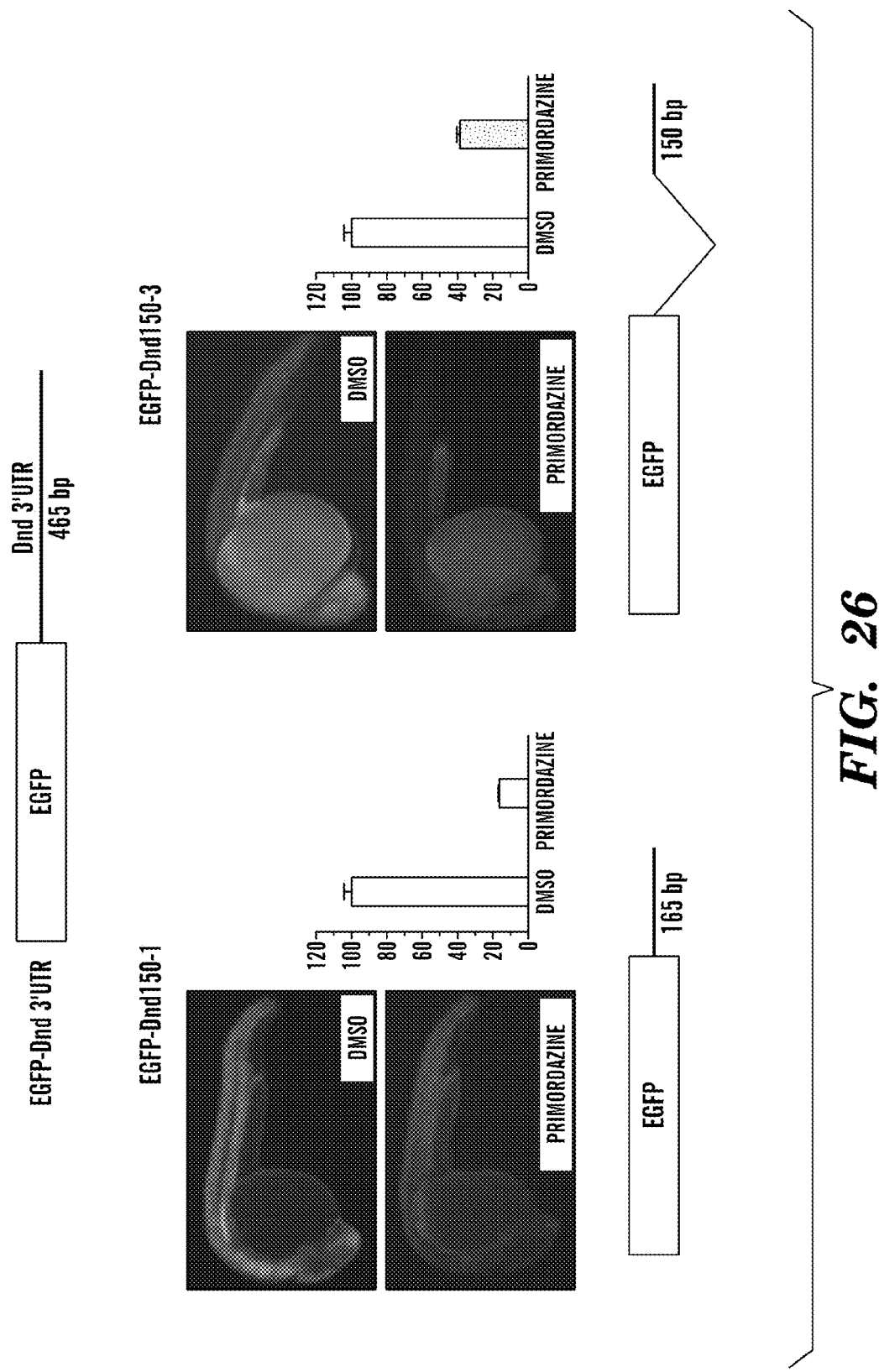
FIG. 26 illustrates that, in addition to regulating the translation of proteins containing elements from the nanos1 3' UTR, primordazine blocks translation of proteins from mRNAs containing the deadend 3'UTR. GFP message is tagged with fragments of the deadend 3'UTR, and treatment with primordazine blocks the translation of EGFP.
Figure 29:
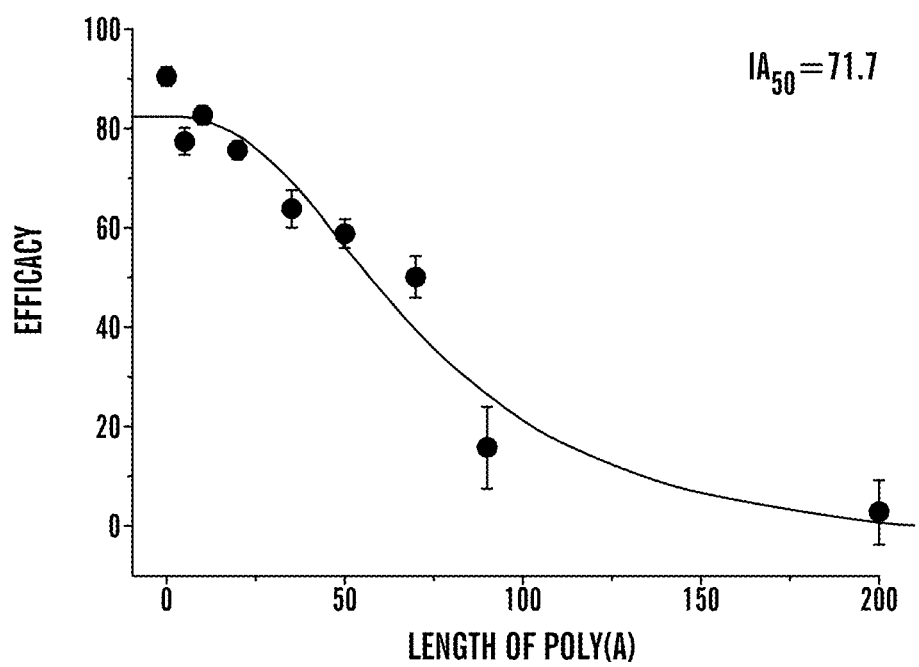
FIG. 29 illustrates that longer polyA tails reduce the efficacy of primordazine in blocking translation. PolyA tails of varying length were added to the end of an RNA containing the primordazine response element, and the efficacy of primordazine was tested.
Figure 30:
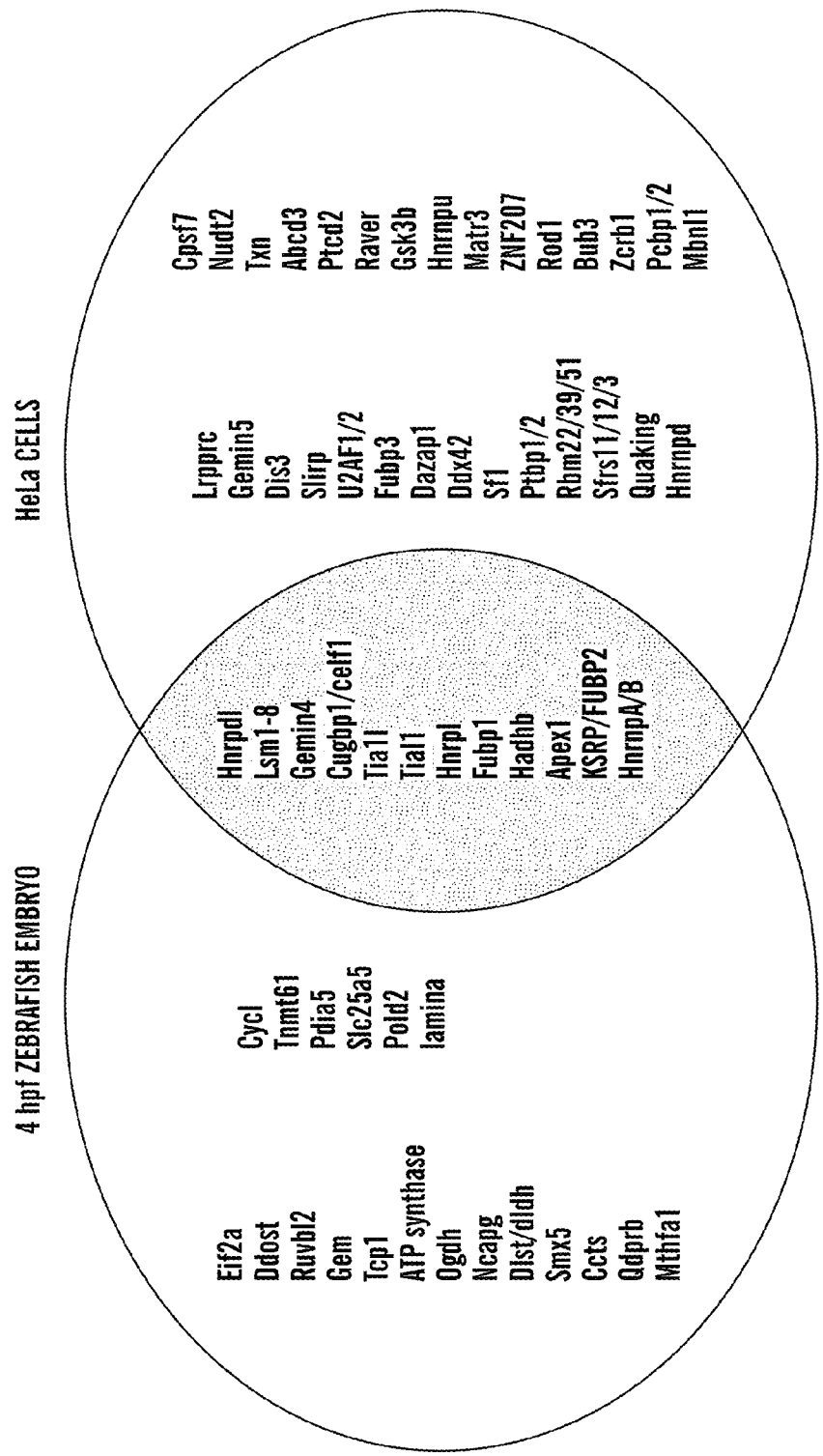
FIG. 30 illustrates that proteins which bind the primordazine response element (PRE) were identified by quantitative proteomics using zebrafish embryos or human HeLa cells. Some of the binding proteins were identified from both cellular sources.
Figure 31:
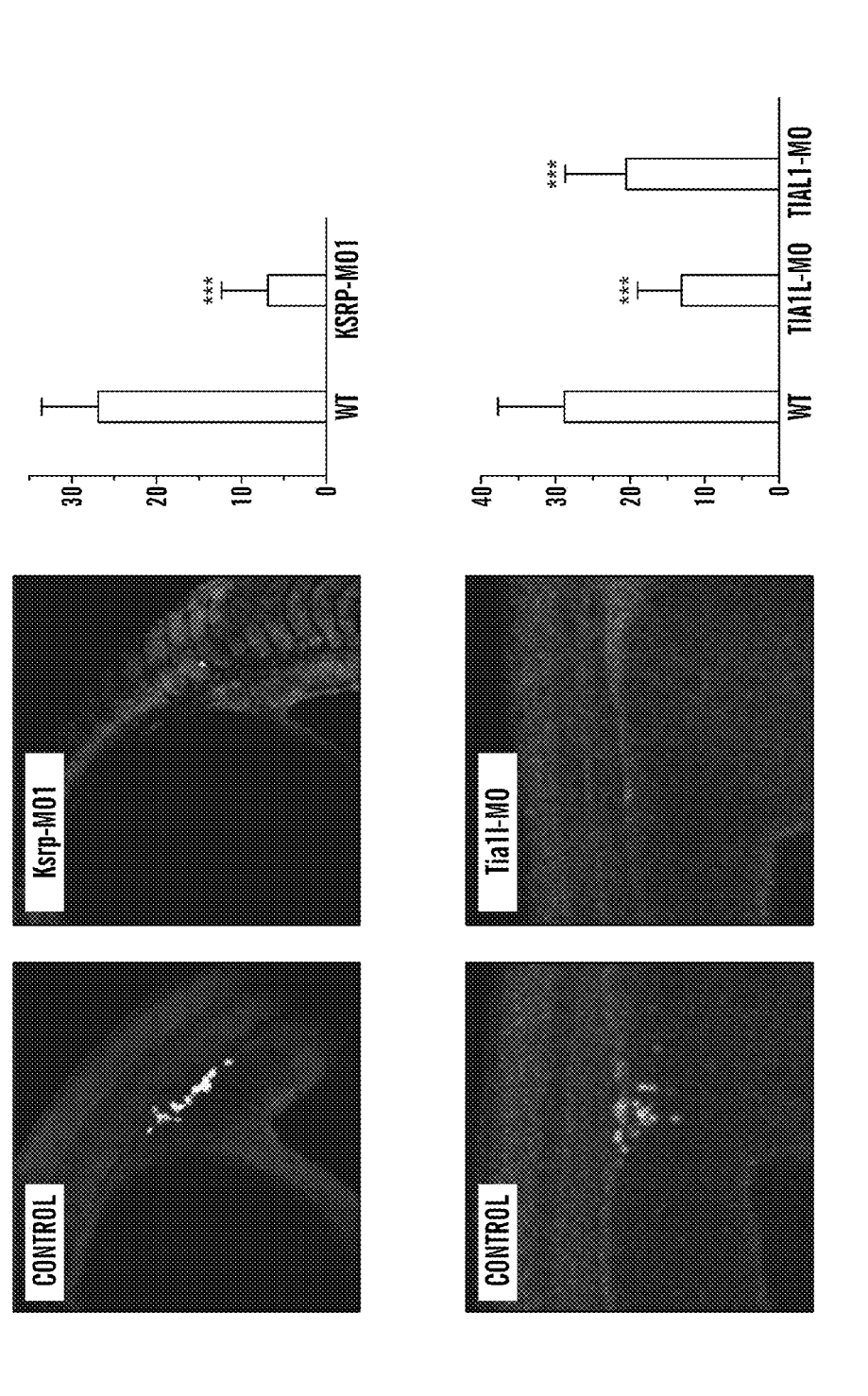
FIG. 31 illustrates that antisense morpholino oligonucleotides were used to knock down KSRP, TIA1L, or TIAL1 expression in zebrafish. Knockdown of any of the genes caused a reduction in the number of primordial germ cells identified in the embryos.
Figure 32:
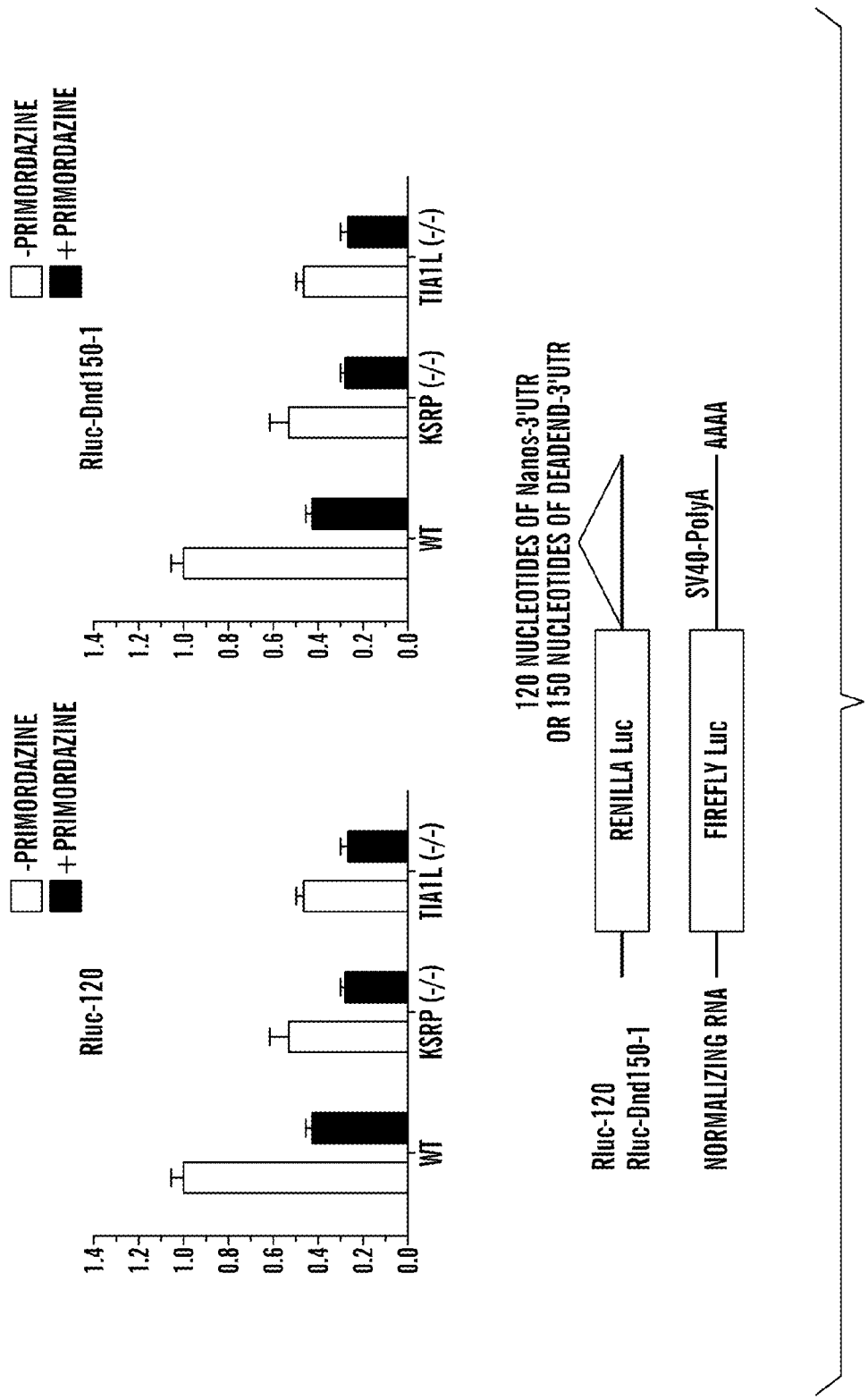
FIG. 32 illustrates that, beyond reducing the number of PGCs (as shown in FIG. 31), knockdown of the genes caused a reduction in the translation of PRE-containing transcripts, as quantified using luciferase constructs tagged with 120 nucleotides from the nanos1 3'UTR or 150 nucleotides from the deadend 3'UTR. For each group of columns in the plots, the left column represents "−primordazine", and the right column represents "+primordazine".
Figure 33:
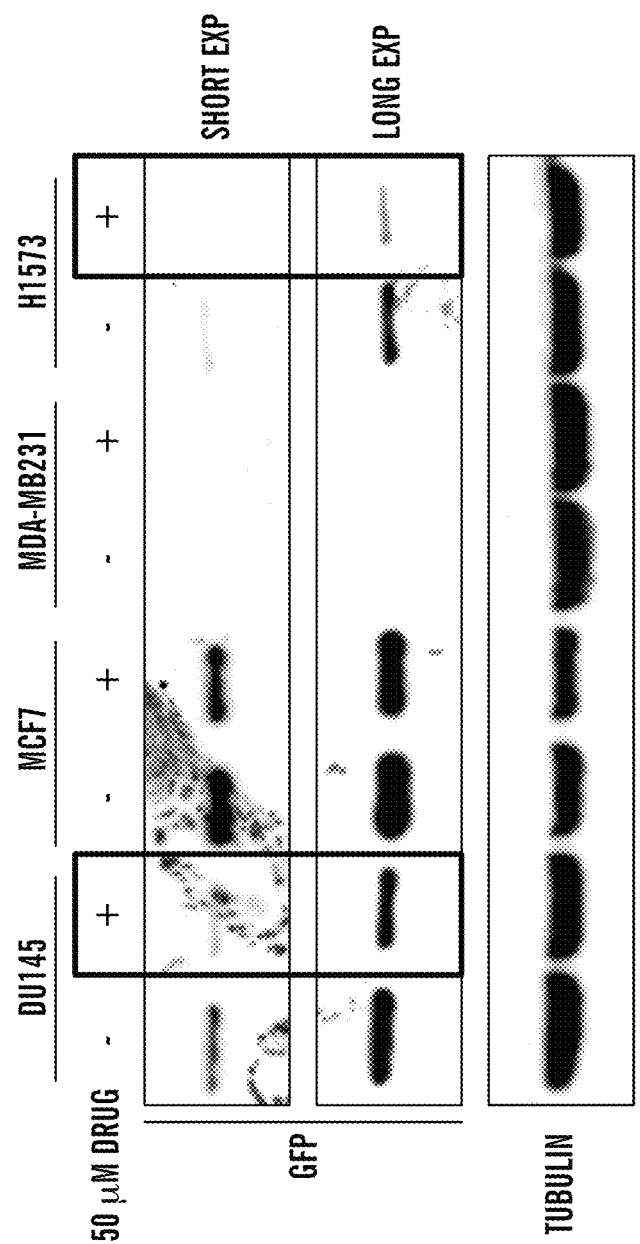
FIG. 33 illustrates that primordazine inhibits translation of PRE-containing mRNAs in mammalian cells. GFP mRNA was tagged with 120 bases from the nanos1 3'UTR and transfected into various mammalian cell lines. The effect of primordazine was determined by western blotting.
Figure 34:
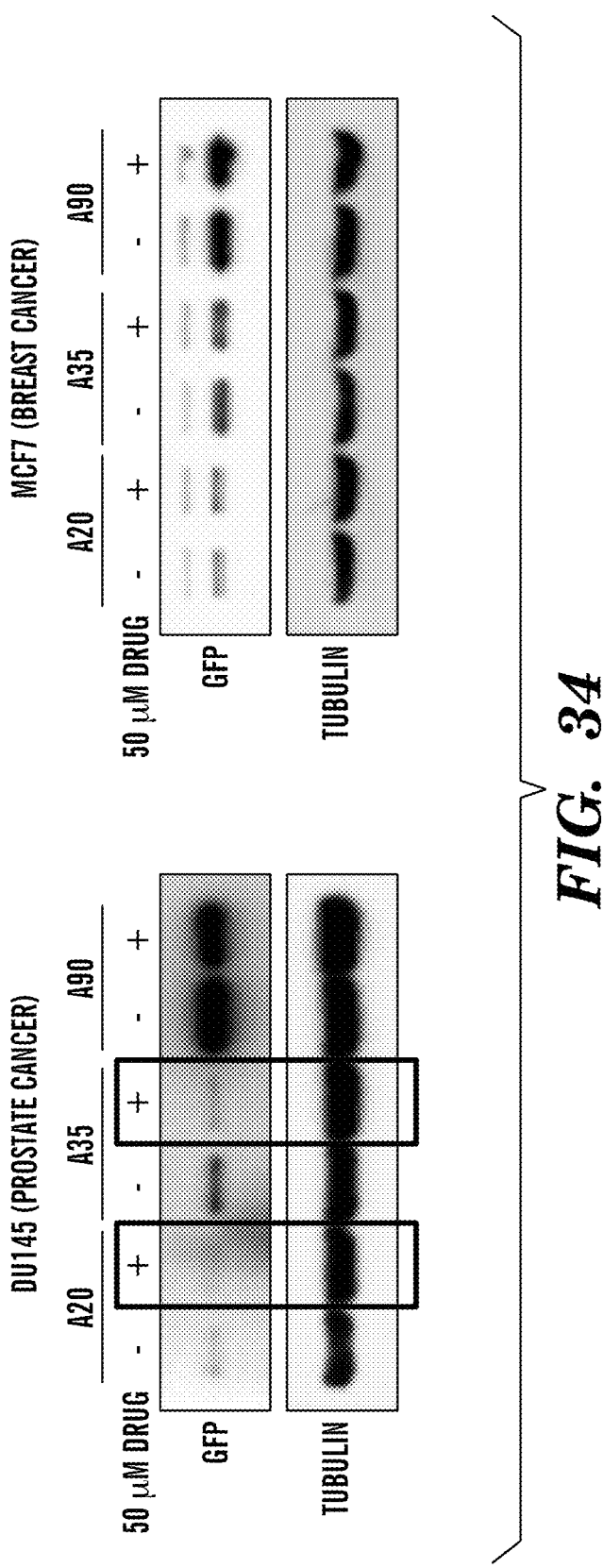
FIG. 34 illustrates that primordazine inhibits translation of PRE-containing mRNAs in mammalian cells. The length of polyA tail was varied as indicated (20, 35, or 90 A bases (SEQ ID NOS 1-3, respectively)).
Figure 35:
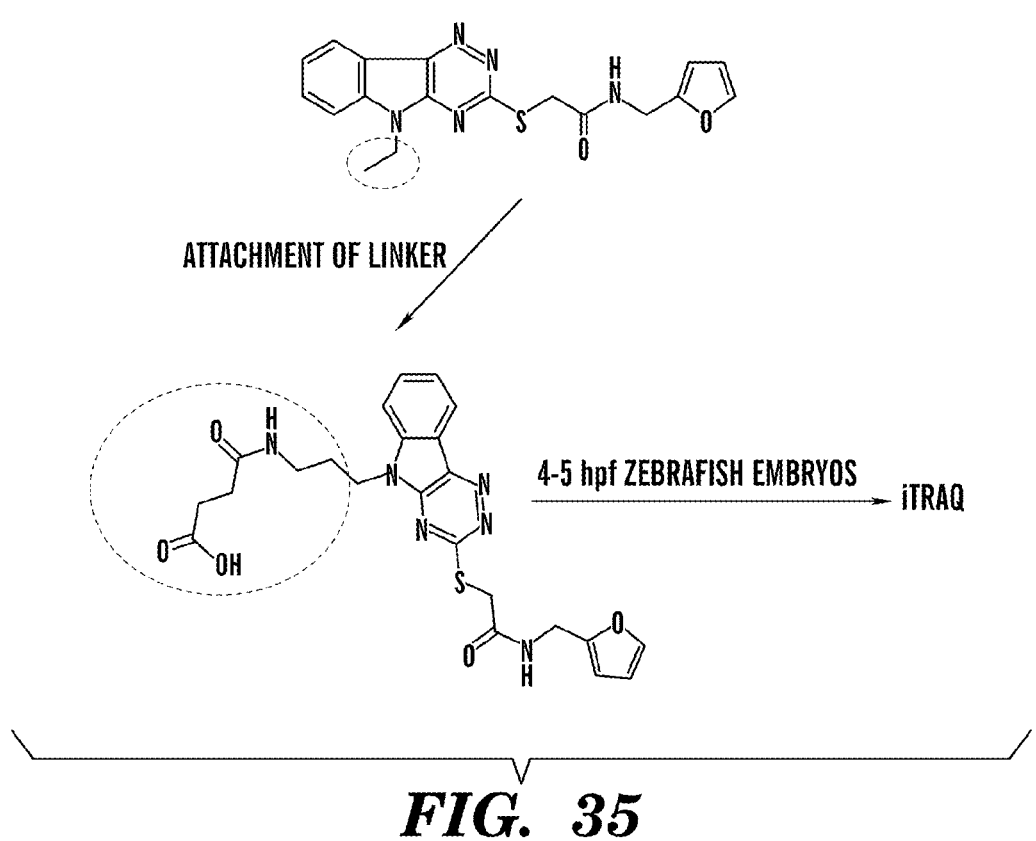
FIG. 35 is a schematic for immobilizing primordazine on solid support and purifying primordazine-binding proteins.
Figure 36:
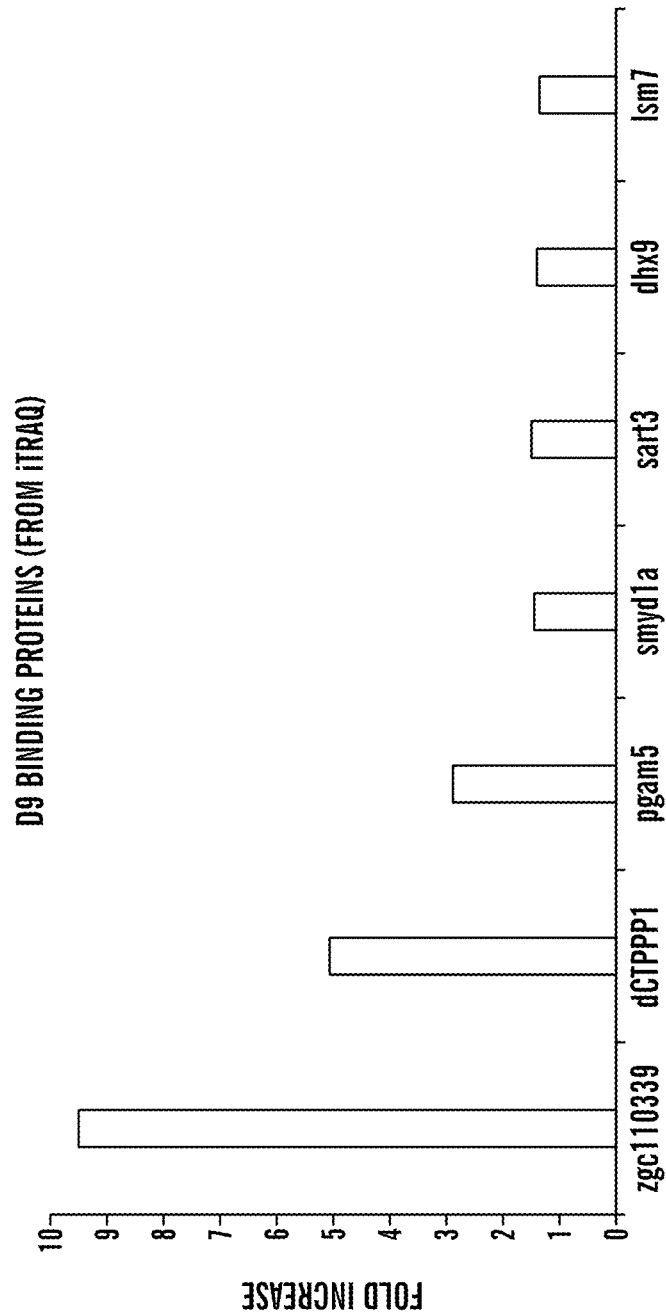
FIG. 36 shows potential primordazine binding proteins identified by mass spectroscopy.
Figure 37:
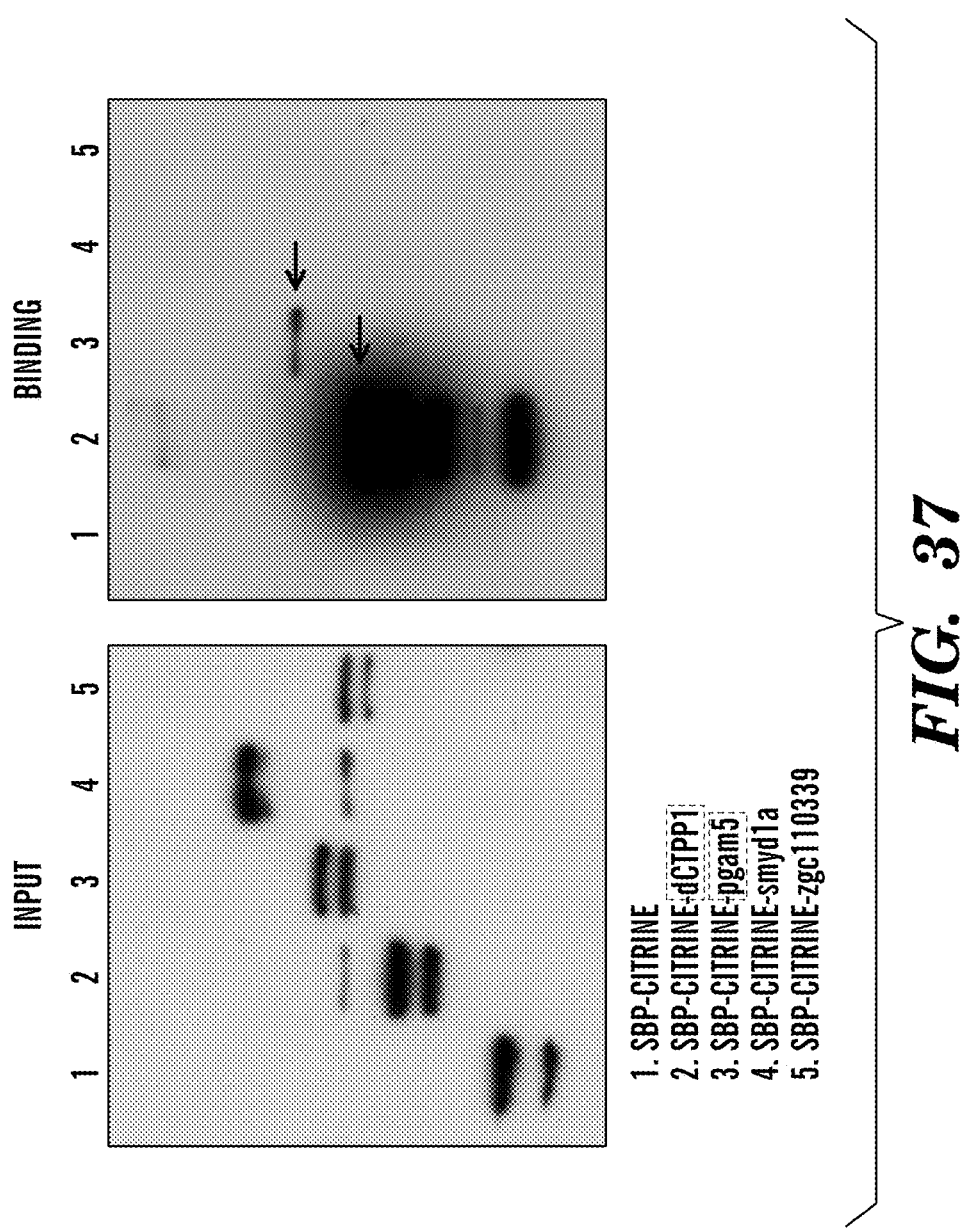
FIG. 37 is western blot confirmation that dCTPP1 and pgam5 bind to primordazine.
Figure 38:
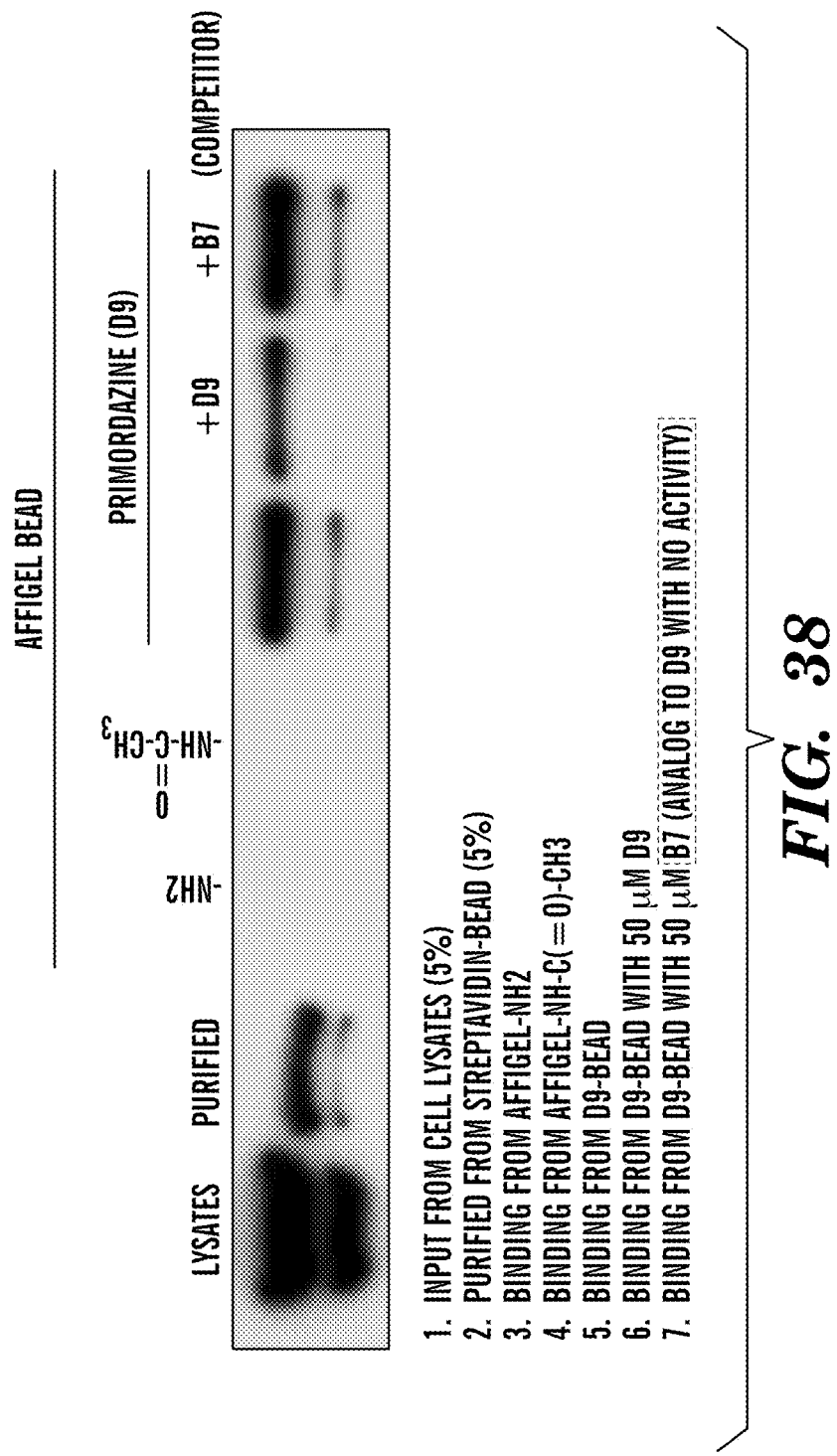
FIG. 38 is western blot confirmation that dCTPP1 binds to primordazine beads and can be competed away by primordazine (D9) but not by an inactive derivative.

Early rounds of compound design should focus on three distinct regions that emanate from the central triazinoindol pharmacophore of the primordazine structure: (1) the acetylphenyl ring, (2) the thioacetamide, and (3) the ethyl group pendant to the indole nitrogen. These regions are highlighted on the primordazine structure and indicated as R1, R2, and R3 respectively (See FIG. 25). Preliminary Results suggest that Region 1 is relatively tolerant of modifications, accepting changes to methylfuran or chlorophenyl groups (see FIG. 25). The flexibility afforded by this region provides an opportunity to make fairly major modifications in an effort to alter potency and selectivity. Chemical space can be explored fairly broadly when making modifications to this region. A search of commercially available compounds has identified more than 300 compounds that preserve the central primordazine pharmacophore but vary Region 1. Examples of moieties that can be tested at R1 include ethane, ethanol, isopropane, piperidine, piperazine, morpholine, thiadiazole, benzothiazole, thiazole, phenothiazine, aminosulfone, pyridine, isoxazole, carboxylate, naphthalene, etc. Region 2 is not as synthetically accessible as Region 1, and fewer commercial compounds are available with variation at R2. Nevertheless, preliminary results (see FIG. 25) suggest that Region 2 can tolerate some modification, including —H and —C2H5 at R2. A few additional modifications at this position can be explored, including —CH3, -isopropyl, and -benzyl. Region 3 appears to be relatively accessible synthetically, and numerous modifications at R3 are commercially available, including methyl, ethyl, propyl, isopropyl, butyl, allyl, benzyl, phenylethyl, and acetic acid derivatives.

Each region can be modified individually, for example by making changes in region 1 while keeping regions 2 and 3 constant. Beneficial modifications from multiple regions are then be combined with the expectation of identifying additive or synergistic effects. In addition to modifying the pendant groups at R1, R2, and R3, the effects of modifying the central pharmacophore itself can be explored, for example by moving or removing ring nitrogens and by modifying the thioether and amide linkages.

(2). Compound Acquisition.

Where possible, compounds are acquired by purchase rather than synthesis. Chemoinformatic programs such as ChemNavigator (www.chemnavigator.com) and ChemFinder (www.chemfinder.com) can be used to identify commercially available compounds and building blocks. An initial analysis suggests that there are hundreds of commercially available compounds related in structure to primordazine. Where compounds are not commercially available, they can be synthetically accessible in few steps.

(3). Compound Potency Testing.

Optimization is driven primarily by potency, meaning that each compound acquired is tested for potency, and potency changes influence subsequent rounds of compound design. For testing compounds, 3-5 transgenic zebrafish embryos (expressing GFP from the vasa promoter) are placed in each well of clear-bottom, black-wall 96 well plates. Embryos are treated with DMSO or varying doses of a compound in two-fold dilutions from 8 uM to 16 nM, beginning at 2 h postfertilization. At 24 h, the plate is loaded onto the screening microscope, which systematically scans wells and captures fluorescent images of fish in each well. The efficacy of each compound dose in ablating PGCs is recorded, yielding an EC50 for each compound.

Biochemical and proteomic experiments can elucidate the targets and mechanisms of action of primordazine, shedding further light on the biological pathways regulating germ cell development and fertility.

Primordazine appears to function by a novel mechanism to ablate PGCs. Elucidating this mechanism can provide important new insights into PGC biology and may uncover new targets and techniques for manipulating fish fertility. Some of the details of primordazine's mechanism were already uncovered. For example, it was identified a novel response element in the nanos1 3' UTR regulates the translation of this master germ cell regulator. Two proteins, FUBP2 and TIAL1, that bind to the primordazine response element were identified and were found to be necessary for germ cell maintenance (see FIG. 6).

Purify Polysomes and Quantify Changes in Actively Translated mRNA by RNA Sequencing.

RNA sequencing (RNA-seq) is used to examine the set of RNAs that is being actively translated (present in polysomes) with and without primordazine treatment. This experiment has the potential to find all RNAs that are regulated at the translational level by primordazine-sensitive pathways. Without wishing to be bound by theory, association of an mRNA with ribosomal polysomes is generally viewed as an indicator that the mRNA is being actively translated. Therefore, there can exist a subset of mRNAs whose interaction with polysomes is altered by primordazine treatment. To identify this subset of mRNAs, polysomes are purified from untreated and primordazine-treated zebrafish and compare the associated mRNAs by RNA-seq. This experiment can be performed as follows:

(1) mass matings. Large-scale matings of wild-type zebrafish generate >10,000 synchronized zebrafish embryos.

(2) primordazine treatment. Half of the embryos are treated with primordazine from 2-6 hpf; the other half are treated with DMSO.

(3) deyolking. At 6 hours postfertilization, embryos are crushed by gentle pressure with mortar and pestle in Ringer's buffer on ice. Cells are rinsed and pelleted several times to remove yolk and chorions.

(4) cell lysis. Cells are lysed in Triton-X buffer containing cycloheximide, protease and phosphatase inhibitors as described (Masek et al., Methods Mol. Biol. 2011, 703, 293-309; Melamed and Arava, Methods Enzymol. 2007, 431, 177-201). Lysates are clarified by centrifugation.

(5) polysome purification and RNA extraction. Polysomes are purified by ultracentrifugation on a sucrose gradient as described (Masek et al., Methods Mol. Biol. 2011, 703, 293-309; Melamed and Arava, Methods Enzymol. 2007, 431, 177-201). RNA is extracted from polysome preps using the Trizol method.

(6) library construction, sequencing, and analysis. The dUTP method is used for strand-specific RNA sequencing (Parkhomchuk et al., Nucleic Acids Res. 2009, 37, e123). This method is preferred by the Broad Institute Genome Sequencing Platform, because comparison of the seven leading RNA-seq methods showed that the dUTP method performs best as measured by strand specificity, library complexity, and continuity and evenness of coverage (Levin et al. Nat Methods 2010, 7, 709-715). Briefly, RNA is fragmented by heating in sodium citrate solution. 200 ng of RNA is primed with random hexamers and first strand synthesis is performed with SuperScript III, SUPERase-In, and actinomycin D. First strand is cleaned up by extraction/precipitation, followed by second strand synthesis with dTTP replaced by dUTP. Paired-end libraries are prepared for Illumina sequencing according to manufacturer instructions. Sequencing is performed on an Illumina Genome Analyzer II, with standard sequencing primers and 76 base reads. Data analysis is performed using Trinity, a suite of RNA-seq analysis tools developed by the Broad Institute Genome Sequencing Platform (Grabherr et al., Nat Biotechnol 2011).

The majority of mRNAs should not be affected by primordazine treatment and should therefore be equally represented in polysome fractions from untreated and primordazine-treated embryos. This is based on the observation that primordazine-treated animals have few overt developmental defects outside the germline, suggesting that primordazine does not cause general translation blockade. Therefore, housekeeping genes and other genes not regulated by primordazine should be found equally in polysomes from untreated and primordazine-treated animals. In contrast, nanos1 mRNA should be changed in its localization and translation by primordazine treatment and therefore should be present at higher levels in untreated polysomes than in primordazine-treated polysomes. Most importantly, a subset of mRNAs can be identified that, like nanos1, are altered in their translation by primordazine treatment. These mRNAs should be over- or under-represented in primordazine-treated polysomes. Such RNAs are of great interest because they can help identify additional pathways that are regulated by the primordazine-sensitive RNA processing machinery.

It should be noted that alternative approach of using iTRAQ to detect changes in protein levels in primordazine-treated animals can be used (Ross et al., Mol Cell Proteomics 2004, 3, 1154-1169). This method has the advantage of allowing direct measurement of protein quantities but would not easily distinguish between translational effects and effects due to changes in transcription or protein stability.

Identify Direct Targets of Primordazine.

Although the primordazine response element in the nanos1 3' UTR is identified, it is possible that primordazine does not act directly on the RNA itself, but rather on proteins upstream of the RNA. It therefore is useful to determine what the direct binding partner(s) are for primordazine. An active form of primordazine has been synthesized that is covalently linked to Affi-gel beads, which can be used in combination with state-of-the-art proteomics to identify the zebrafish proteins that interact with primordazine.

A primordazine derivative is synthesized in which an 8-atom linker was appended from the indole nitrogen, terminating in a carboxylic acid (FIGS. 4B and 4C). This derivative with linker retained full PGC-ablating activity in zebrafish embryos, indicating that attachment of the linker does not interfere with the interaction between primordazine and its binding partners. The derivatized primordazine can then be coupled to Affi-Gel 102 agarose beads, generating an affinity matrix that can be used to identify the targets of primordazine (FIGS. 4B and 4C).

Figure 15:
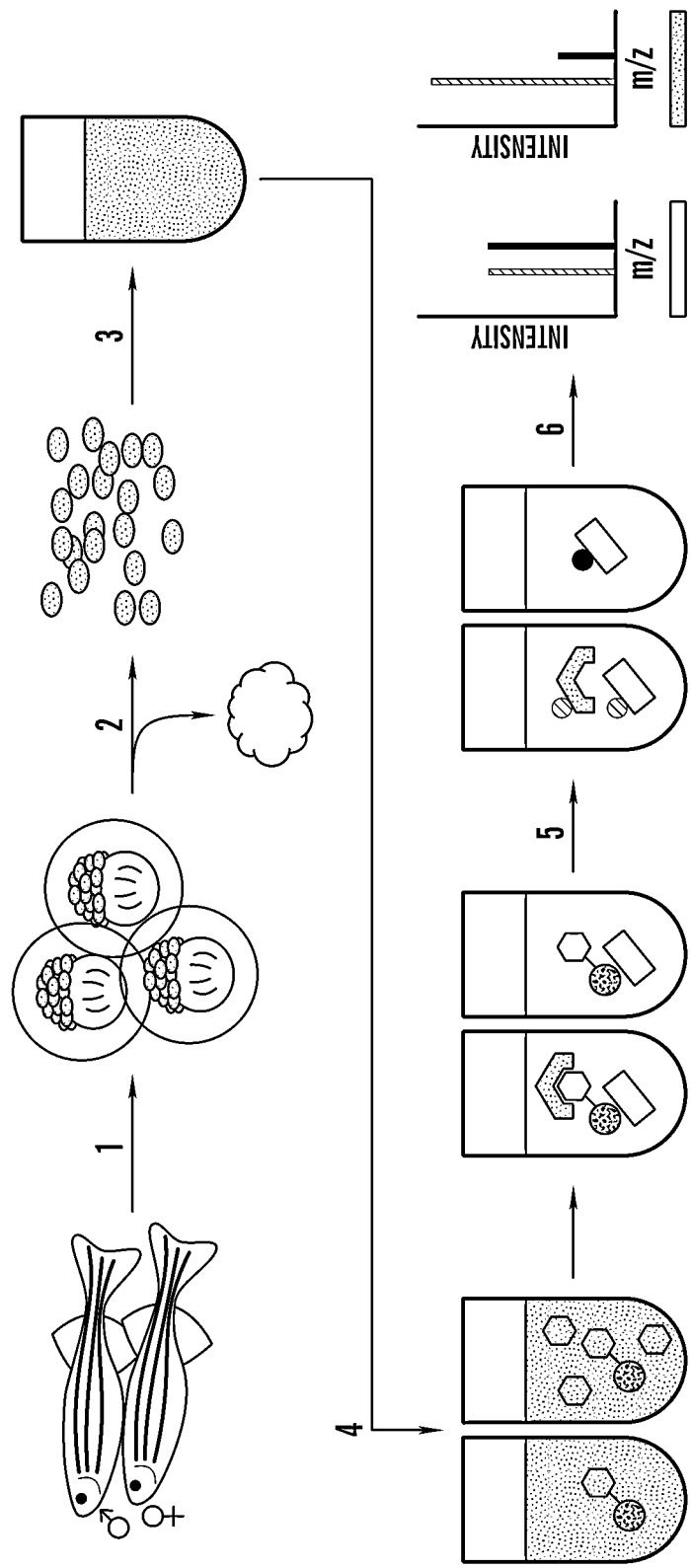
FIG. 15 illustrates a schematic representation of experiments conduct to elucidate what bonds to the primordazine response element.
Figure 16:
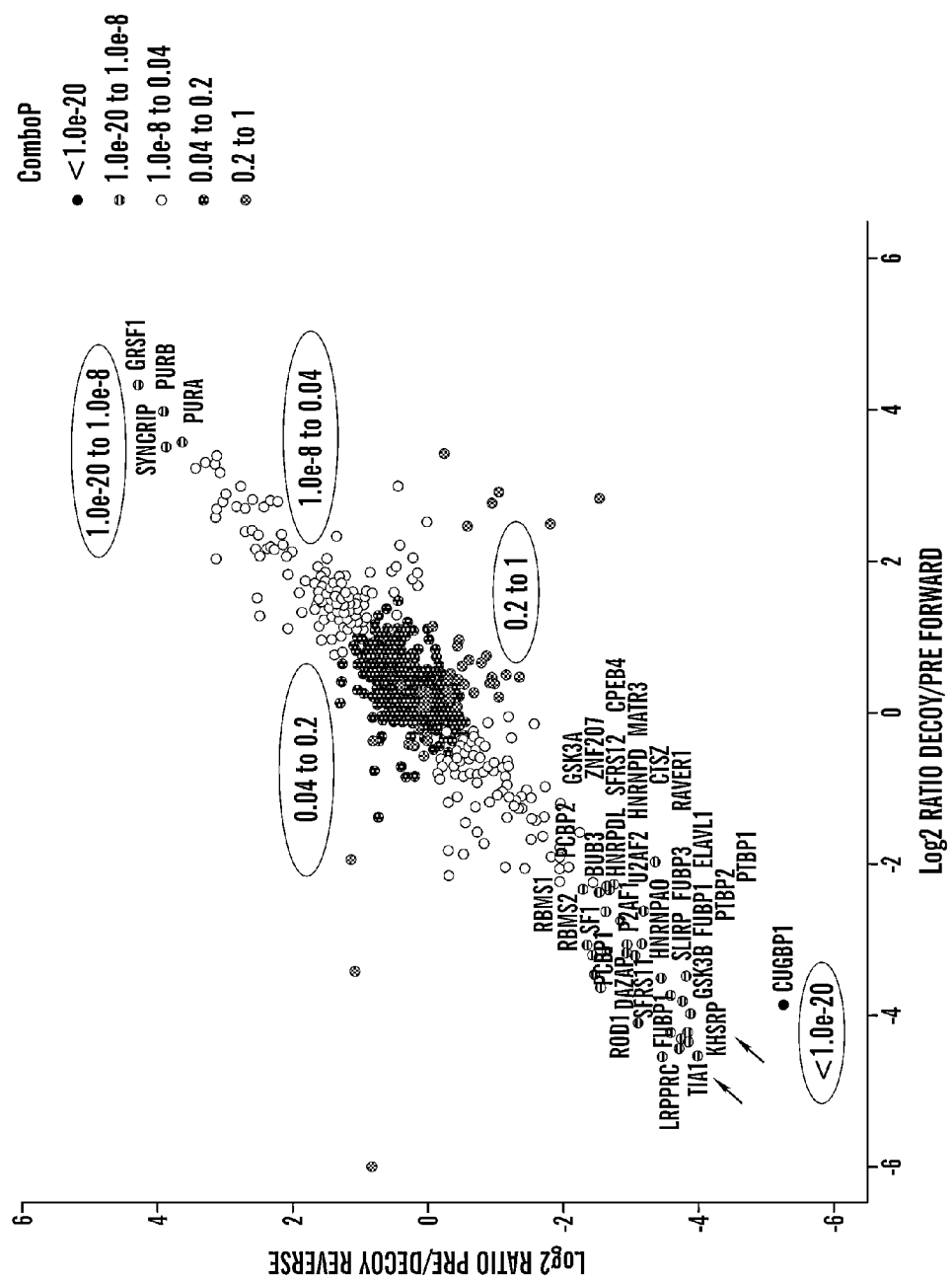
FIG. 16 illustrates what binds to the primordazine response element.
Figure 17:
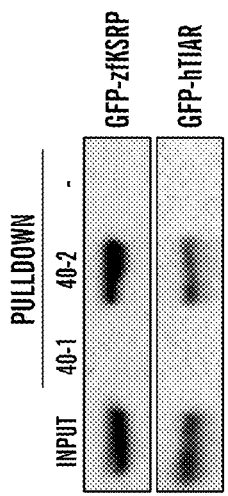
FIG. 17 illustrates mass spectrometry results.
Figure 18:
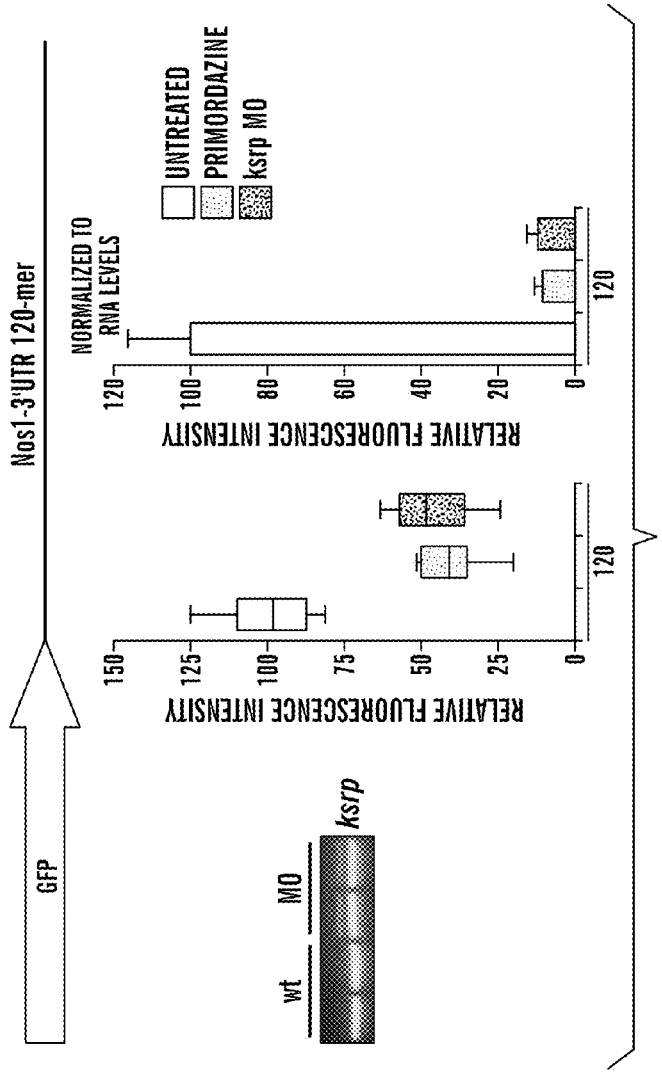
FIG. 18 illustrates KSRP knockdown phenocopies primordazine treatment. In each data plot, the series from left to right is untreated, promordazine, and ksrp MO.
Figure 19:
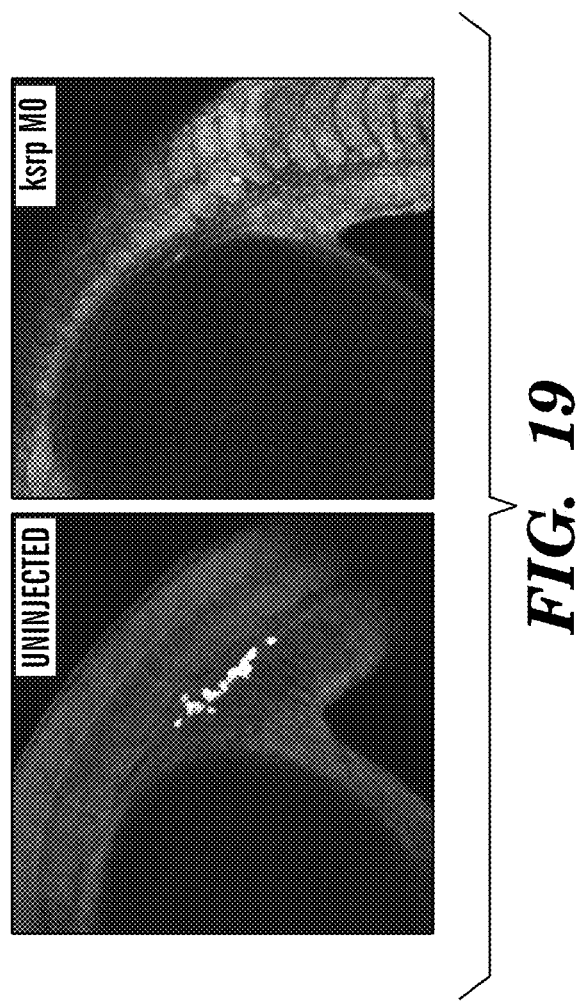
FIG. 19 illustrates KSRP knockdown phenocopies primordazine treatment.
Figure 20:
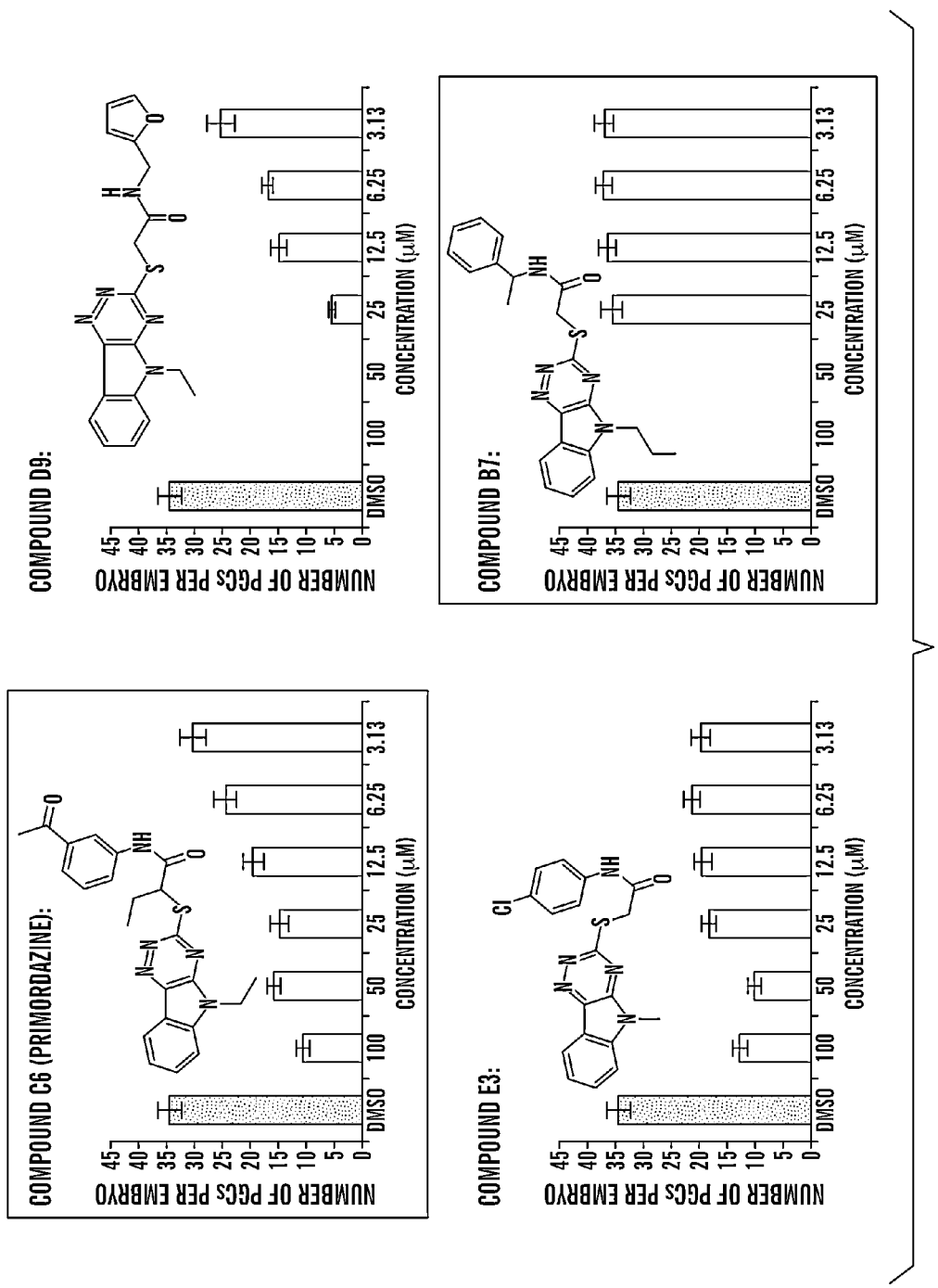
FIG. 20 illustrates a simple SAR from initial screen results.
Figure 21:
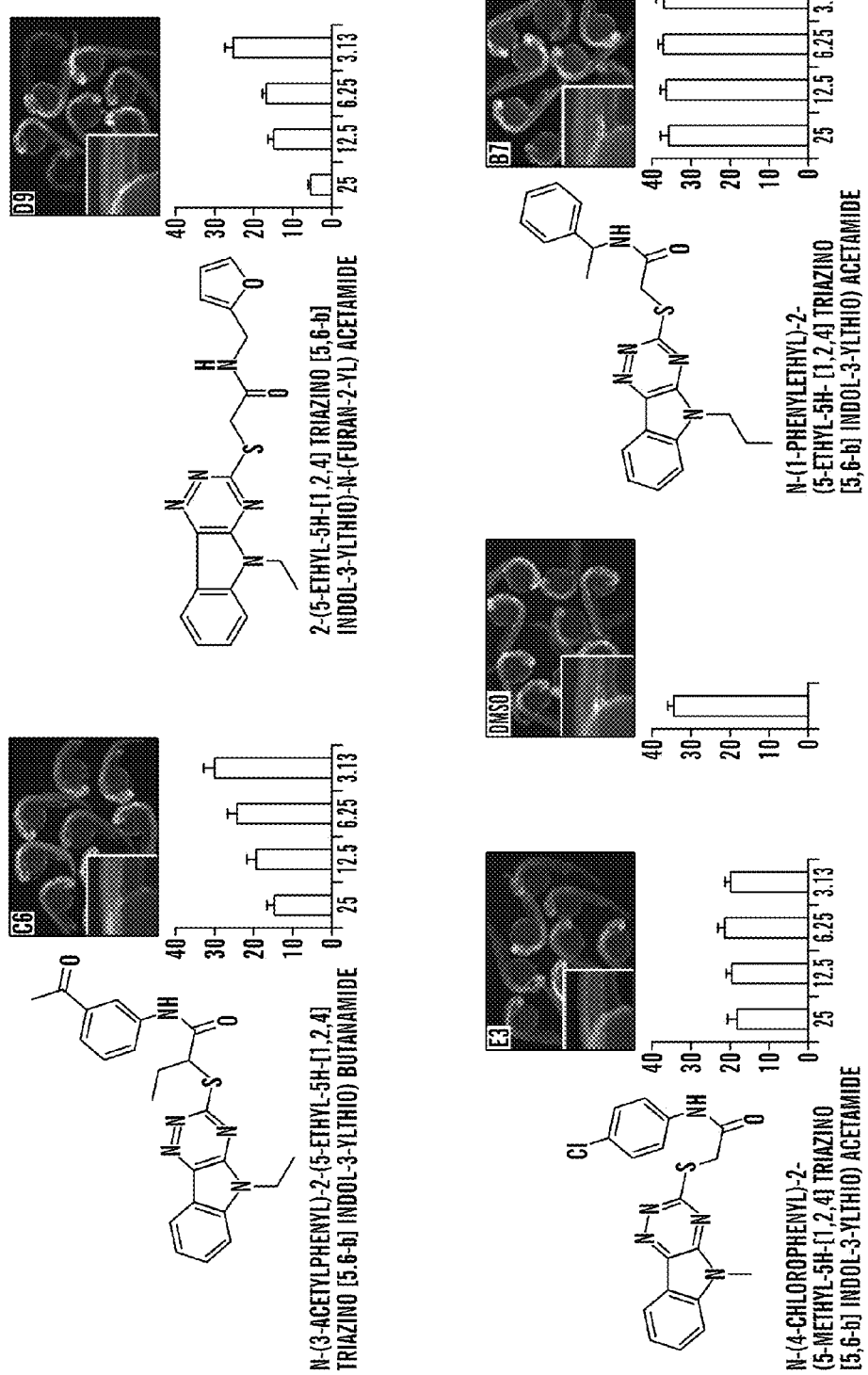
FIG. 21 illustrates a simple SAR.
Figure 22:
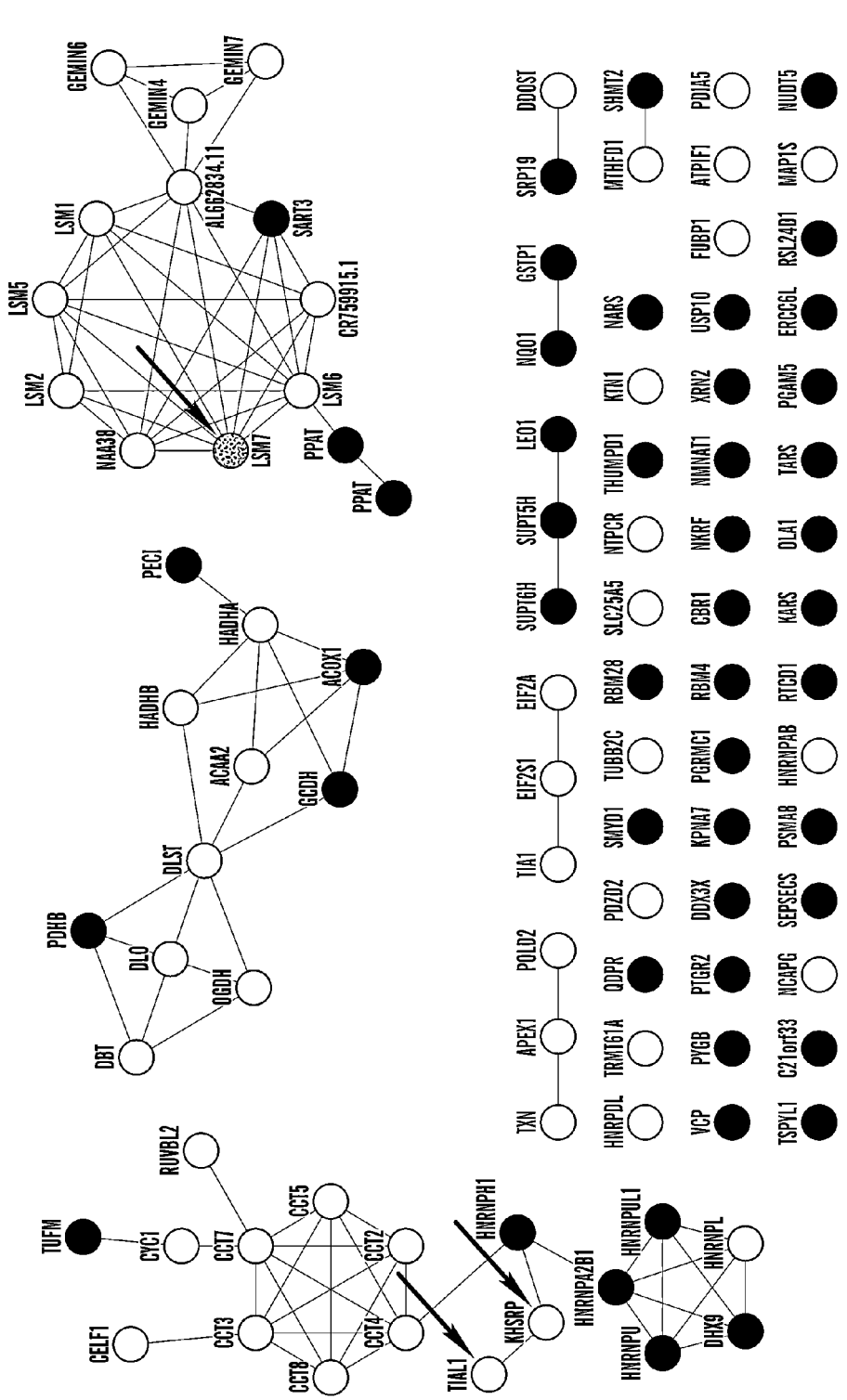
FIG. 22 illustrates a network analysis of primordazine and PRE binding proteins.

The active affinity matrix for primordazine can be used to identify proteins that bind to primordazine. Specific binders can be identified using a quantitative proteomic technique called iTRAQ (isobaric tag for relative and absolute quantitation) (Ross et al., Mol Cell Proteomics 2004, 3, 1154-1169). iTRAQ allows one to identify and quantify all of the proteins that bind to a small molecule, even when binding is weak, and to assess the specificity of binding by competition with free compound. Published protocols for iTRAQ experiments can be found in these references (Ong et al., PNAS USA 2009, 106, 4617-4622; Unwin et al., Nat. Protoc. 2010, 5, 1574-1582). The process is depicted in FIG. 15 and consists of:

(1) mass matings. Large-scale matings of wild-type zebrafish generate >10,000 synchronized zebrafish embryos.

(2) deyolking. At 4 hpf, embryos are crushed by mortar and pestle in Ringer's buffer on ice. Cells are rinsed and pelleted several times to remove yolk and chorions.

(3) cell lysis. Cells are lysed in Triton-X buffer containing protease and phosphatase inhibitors. Lysates are clarified by centrifugation.

(4) binding and competition. Cell lysates are incubated with the primordazine affinity matrix overnight, with or without competition with excess free primordazine. Affinity beads are then rinsed briefly with lysis buffer to remove the majority of unbound protein.

(5) isobaric labeling. The two protein samples to be compared (with and without competition) are labeled with separate isobaric tags. These tags have identical chemical properties but different isotopic masses, so they elute together by liquid chromatography but generate separate peaks by mass spectrometry.

(6) protein quantification. The two protein samples are mixed, trypsinized, and analyzed by LC/MS. Proteins that bind non-specifically to the affinity matrix should be present with equal amounts of each isotopic tag. Proteins that bind specifically to primordazine should be enriched for the "no competition" tag relative to the "competition" tag.

It is contemplated that alternative approaches can be used to identify the relevant targets of primordazine, especially for proteins having low abundance or with very low solubility in detergent buffers (Zon and Peterson, Nat. Rev. Drug Discov. 2005, 4, 35-44).

Confirm Validity of Target(s).

The exact experiments used to confirm the validity of a potential target depends upon the identity of the target, but in every case, confirmation can consist of the following three steps:

(1) confirming interaction between primordazine and the target. The iTRAQ experiments can provide one piece of evidence of interaction between primordazine and the target, but it is important to confirm the interaction using an orthogonal approach. If the target protein can be purified, binding affinity can be tested directly using BIACORE following standard protocols (Jason-Moller et al., Curr Protoc Protein Sci 2006, Chapter 19, Unit 19.13). BIACORE analysis generates accurate information on binding affinity and interaction kinetics between a protein and its small molecule ligand.

(2) testing the effect of primordazine on the target's activity. Many of the targets that are discovered have a known enzymatic activity or other characterized activity. The second step is to test the effect of primordazine on that activity. For example, if the putative target is a kinase, the ability of primordazine to alter the kinase activity of the target is tested. If the putative target is known to regulate transcription of a specific gene, the effect of primordazine on transcription of that gene is tested.

(3) phenocopying the primordazine phenotype by disruption of the target. The putative target can be disrupted using morpholino oligonucleotides or ZFN-induced mutations and one can determine if target disruption phenocopies primordazine treatment. The same three assays described for FIGS. 3 & 5 above can be used, namely nanos1 mRNA localization, mRNA translation, and PGC maintenance. If disruption of the putative target mimics primordazine in these assays, it can support the validity of that target. A good phenocopy is strong evidence for the relevance of the putative target, and many examples of genetic disruption phenocopying a small molecule effect exist. In cases where there is no phenocopy or only a partial phenocopy, approaches, such as titrating the morpholino dose, overexpressing the target, or using alternative pharmacological and genetic approaches for gene disruption, can be adopted.

Ability of Primordazine to Induce Sterility in Phylogenetically Distant Fish Species.

Studies are performed to identify optimal dose, duration, and synergism with other stressors. Sterility is scored in batches of treated fish of varied genetic backgrounds.

In zebrafish, primordazine interferes with the nanos1 3'UTR-mediated location and translational regulation of nanos, which encodes an evolutionary conserved protein essential for PGC survival. It is shown that the 3'UTR of nanos is interchangeably functional in phylogenetically distant fish, hence, primordazine should act as a modulator of NANOS expression across teleost species.

In the beginning, primordazine treatment conditions are optimized to achieve maximal ablation of GFP-labeled PGCs in zebrafish. If ablation is incomplete with primordazine alone, additional stressors, such as warm water treatment, can be implemented. Working in iterative cycles, parameters such as treatment time, dose, genetic background and temperature can be interrogated. Once determined, these optimal conditions are reassessed for sterility inducing capacity by quantifying germ cell-specific gene expression in treated juvenile fish. If sterility is confirmed, the potential detrimental off-target effects of such treatment are evaluated throughout the fish development. Similar optimized conditions and iterative analysis can be applied as a starting point for tilapia and trout. Information on treatment conditions with primordazine is valuable to assess primordazine derivatives which target the same biological process.

(1) Identification of Optimal Dose, Timing and Treatment Length.

a. Zebrafish: Primordazine has been tested on a genetically homogeneous strain with maximal efficacy achieved at hatching water concentrations of 6 uM. The genetic background-dependant dosage effectiveness is first investigated by evaluating primordazine efficacy in two lines of zebrafish expressing GFP in PGCs from maternal specific transcripts (zona pellucida promoter). One is an outbred commercial strain, while the other is a "golden" aquarium strain homozygous for a mutation in slc24a. For each test treatment, embryos produced from 3 parental pairs per line are assayed. Primordazine likely ablates PGCs by interfering with their nos1-dependent migration during post-gastrulation stages and as such treatment is initiated prior to the onset of gastrulation and embryos are analyzed when PGCs have reached the genital ridge. Embryos are obtained from spontaneous cage spawning. One to four hpf zebrafish embryos are arrayed into 24 well plates (10 embryos/wells) prefilled with embryo buffer at 25° C. supplemented with DMSO or varying doses of primordazine in two-fold dilution series from 12 uM to 187 nM. At 24 hpf, live treated embryos are analyzed under fluorescent microscopy.

b. Trout (*O. mykiss*): Gametes are purchased from a commercial trout egg supplier and embryos produced from established in vitro fertilization procedures. To document the ability of primordazine to target trout PGCs, synthetic mRNAs—coding GFP fused to the 3' UTR of nanos1 are prepared from a linearized plasmid (Litmus eGFP:nos1 3'UTR) and delivered into fertilized, one-cell stage, trout embryos using the micropyle injection technique (CAT's established protocol). Forty to fifty injected embryos are placed in temperature controlled 12° C. recirculating water. Three to five dpf, embryos are split into equal groups and placed in 12° C. hatching water supplemented with 12 uM, 3 uM, 187 nM of primordazine or DMSO respectively. Treatment water is replaced daily to ensure proper embryo oxygenation. GFP expression patterns are examined in dechorionated and deyolked embryos.

c. Tilapia (*Oreochromis niloticus*) lines in CAT's facility are derived from a Brazilian strain obtained from a US commercial producer (Desert Springs Tilapia, Arizona). Embryos are produced from in vitro fertilization. To study PGCs, one can assay embryos from female tilapia carrying the ZPC5:eGFP:tnos 3'UTR construct which produce embryos with GFP labeled PGCs. Fertilized eggs are placed into hatching water at 28° C. in plastic Petri dishes with gentle stirring. The first cell division takes place approximately two hours post fertilization and gastrulation begins at 10 hpf. Pregastrula embryos are transferred at time intervals to 6 well plates (20 embryos/well) prefilled with hatching water supplemented with 2 fold dilution series of primordazine from 12 uM to 187 nM or DMSO (control). Embryos are examined under fluorescent microscopy at time intervals.

d. Imaging and data reporting: Embryos are be rinsed with fresh water (FW), mounted in low melt agarose (1% w/v, SeaPlaque GTG) in glass capillaries (Cambrex Corporation BRAND) and imaged using an AxioCam MRm Monochrome CCD digital camera mounted on a SteREO Discovery V8 Stereomicroscope (Zeiss) equipped with LED tube S, with a 38HE filter set for GFP and Zen imaging software (Carl Zeiss International, Germany). Images of 10 embryos per treatment are taken at 24 hpf for zebrafish (at the prim-5 stage, when greater than 95% of PGCs have migrated into the genital ridge region), 3 dpf for tilapia embryos, and at 14 dpf for trout embryos (The 70-somite stage when clusters of GFP-expressing cells have formed a single cluster above the intestine). For each model, the capture settings, magnification and focus plane are standardized. PGC development can be analyzed by counting the number of PGCs on either side of the genital ridges, and the number of ectopic PGCs is recorded as well. GFP intensity at the genital ridges can be analyzed using Zen lite image treatment software (Zeiss). Each treatment group can be represented by a data plot where x represents the average PGC number, and y the average GFP intensity at the genital ridge. Mean total PGCs is statistically compared using an unpaired t test. Significance is accepted when $P<0.05$. Evidence of functionality in all experiments is indicated if GFP-PGCs are significantly reduced in number when compared to control embryos that were not treated with primordazine.

(2). Treatment Optimization and Confirmation of Sterility

If PGC ablation with primordazine treatment alone is incomplete, primordazine can be combined with a short exposure to high temperature. The molecular changes induced by this stressor may have cumulative or synergistic activity on PGC ablation.

a. Warm water treatment: Control or primordazine treated embryos (60, 40 and 20 for zebrafish, tilapia and trout respectively per group) are placed in beakers immersed in a temperature controlled water bath (Table 1). At time intervals embryos are transferred to a Petri dish for GFP-PGCs analysis as described earlier.

TABLE 1

Temperature treatment and control for fish species

| Fish species | Warm temperature treatment and control | Treatment duration From gastrulation onward |
|---|---|---|
| Zebrafish | 34° C. versus 27° C. | 12 hrs |
| Tilapia | 35° C. versus 27° C. | 24-48 hrs |
| Trout | 17° C. versus 12° C. | 2-3 days | b. Confirmation of sterility at the molecular level. Treated embryos lacking visible PGCs and non treated controls, are raised until complete absorption of the yolk sac (45-50 dpf in trout, 30 dpf in tilapia and 25 dpf in zebrafish). For each group, 10 juveniles are sacrificed (MS222) and the abdominal segment containing the gonad (removing head, tail and viscera) are sectioned off RNA is extracted from the remaining tissue and the corresponding cDNA is screened by QPCR using TaqMan probes (Applied Biosystems) for vasa, a germ cell specific gene (Raz, Genome Biol. 2000, 1, 1017.1-1017.6) (accession #AB032467, CF752544, NM_131057 for tilapia, trout and zebrafish respectively). Q-PCRs for each sample are performed in triplicate and level of expression is normalized to a set of host housekeeping genes (Vandesompele et al., Genome Biology 2002, 3, p. research0034) (β-actin, ef1α and rpl13α). No expression of vasa should be in sterile fish.

(3) Documentation of Non-Toxicity in all Three Species of Interest

Primordazine was discovered in a whole organism approach, and effective doses appear to have no visible effect on development or organogenesis, suggesting that primordazine disrupts a PGC specific process. However, toxicity may not be apparent at the morphological level but rather at the cellular level. Tilapia and trout might also show altered toxicity compared to zebrafish. While the treatment is restricted to early embryonic development, it is possible that negative effect may become apparent only on traits that are expressed at the juvenile or adult stage. Ultimately, fish performance evaluation throughout their life cycle can address this issue.

To detect primordazine-induced necrotic or apoptotic activity in somatic tissue, acridine orange staining and TUNEL labeling on embryos are used. Morphohological malformations and developmental delays are also assessed. Finally, to verify that primordazine treatment during early developmental stage does not result in metabolism alteration leading to growth retardation, tank grow out trials are conduct to determine sexual differentiation and fish performance.

a. Acridine orange stains cells with disturbed plasma membrane permeability so it preferentially stains necrotic or very late apoptotic cells. Embryos are rinsed with FW and then incubated in 100 µl of 5 µg/ml acridine orange for one hour in the dark at 28° C. Embryos are examined under fluorescent microscopy and the number of fluorescent cells is scored.

b. TUNEL labeling: Detection and quantification of apoptosis are performed using an In Situ Cell Death Detection Kit (TMR red Roche, Nutley, N.J.) following the manufacturer's protocol. 36 hpf embryos are dechorionated and fixed in 4% paraformaldehyde for 1 hour at room temperature. Fixed embryos are washed with PBS twice and permeabilized with 0.1% sodium citrate, 0.1% TritonX for 2 minutes on ice. After washing twice in PBS, samples are incubated with the reaction mixture containing the terminal deoxynucleotidyl transferase and TMR labeled nucleotides for 1 hour in the dark at 37 C. The reaction is stopped by washing with PBS three times. The fluorescent signal is visualized and imaged as described above (imaging and data reporting).

c. Deformities are scored/control non treated group. Specifically, malformation such as yolk sac edema, pericardial edema, axial edema/blistering, axial malformations (crooked/clubbed) are tabulated using a scale of 1 to 3, with 1 representing a normal phenotype and 3 a non viable deformed embryo. Each image is read blind by two reviewers.

d. Tank grow out trials. To generate groups used for these trials, embryos from single-paired crossings (minimum of three separate crosses) are exposed to 1) optimized treatment resulting in complete PGC ablation (i.e sterile, all male) 2) no treatment (i.e fertile control group). Treatment and control embryos (zebrafish and tilapia) are reared separately using established hatchery procedures. At the feeding stage, half of the control is sex reversed using standard androgen treatment protocols (feeding methyl testosterone incorporated into feed). At ~1 month of age (10 g), tilapia from the treatment and control/sex-reversed groups (n=50-100/group) is weighed, pit-tagged and held together in 100-liter tanks in a recirculating culture system maintained at 27° C. (12H light: 12H dark). All fish is fed twice daily, to satiation, using a commercially prepared grow-out diet (Ziegler Feeds). At ~3 weeks of age zebrafish from each treatment group (n=60) is placed in 8 L tanks (n=20 fish/tank) and raised separately. Each fish is individually weighed and measured at 4-week intervals over a 24 week period. Males are identified, visually, based on their body shape, color, absence of uro-genital papillae or structure of the uro-genital orifice. At the end of the experiment, fish is sacrificed and gonadal structure dissected (n=20 per group) fixed in Bouin's solution, dehydrated and infiltrated with paraffin for sectioning. Each section is read blind by two reviewers. Sterility is apparent from a complete absence of spermatozoa in the tubule lumen. Each section is assigned a score using a qualitative scale: grade 1=normal gonad, grade 2=gonad with depleted germ cells, grade 3=gonad with absent germ cells. Individual weights from fish assigned as either 'Male/Fertile' (testis with germ cell) or 'Male/Sterile' (testis without germ cell) are plotted over time and averaged weights (from at least 50 fish/group) are compared between groups using Student t Test. Individual fish that could not be assigned to these 2 groups (i.e. "Female') is discarded from the analysis.

Example 11

Treating Tilapia with Primordazine

Method

Tilapia (*Oreochromis niloticus*) lines used in this study are derived from a Brazilian strain obtained from a US commercial producer.

To study PGCs, assays were performed on embryos from female tilapia carrying the Zpc5:eGFP:tnos 3'UTR construct which produce embryos with GFP labeled PGCs. The tilapia Zpc5 promoter is an oocyte specific promoter, active during oogenesis prior to the first meiotic division. As such, all embryos from an heterozygous transgenic female inherit the eGFP:tnos 3'UTR mRNA, which localizes and become expressed exclusively in PGCs through the action of cis-acting RNA element in their 3'UTR (tilapia nanos 3'UTR). In this system GFP expression in the embryo is strictly maternal. Thus, similarly to zebrafish nos1 3'UTR, tilapia nanos 3' UTR (tnos 3'UTR) can deliver mRNA and subsequently heterologous protein expression to the PGCs in developing embryos. In this line, GFP expression is first observed in 2 day old embryos, progeny of transgenic female. At 3 days post fertilization (dpf) in 28° C. water, GFP-expressing cells coalesced in two bilateral rows on the midline above the intestine (FIG. 41A). The GFP labeled primordial germ cell can be visualized for up to 6 days post fertilization but fluorescence starts to fade between days 4 & 5.

Primordazine treatment: Embryos at different developmental stages were placed into hatching water at 28° C. in plastic Petri dishes with gentle stirring. The first cell division takes place approximately two hours post fertilization (hpf) and gastrulation begins at around 10 hpf. We transferred pre-gastrula (2 hpf, 5 hpf) and post-gastrula embryos (15 hpf) to 96 well plates (1-2 embryos/well) prefilled with hatching water supplemented with 2 fold dilution series of primordazine from 20 uM to 2.5 uM or DMSO (control). The 96 well plate was placed under gentle stirring in a temperature control room at 28° C. At time intervals, embryos were analyzed for GFP expression under a fluorescence dissecting microscope (Zeiss Stereo Discovery.V8) equipped with a GFP filter set. To quantify primordazine activity, 3 day old embryos were placed in fresh water and PGCs were counted. At this stage, in the non-treated control group, approximately 95% of PGCs have migrated to the genital ridges.

Results

Figure 39:
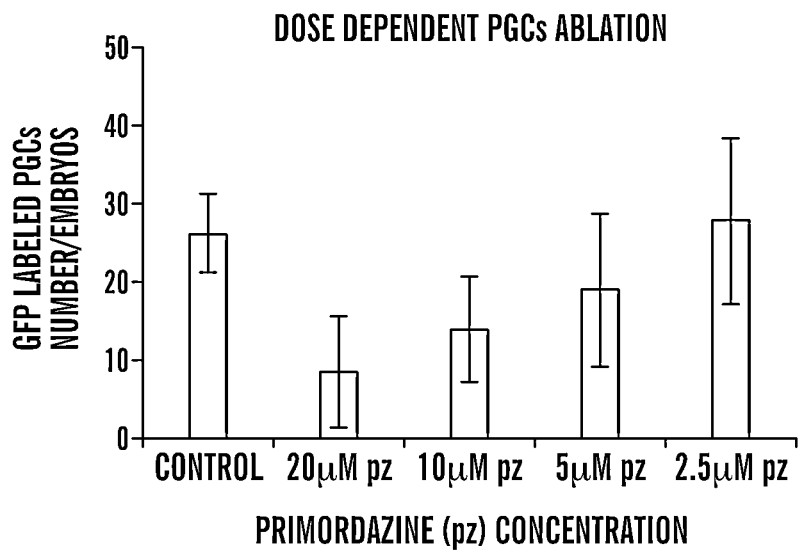
FIG. 39 shows experimental results after 5 hours old tilapia embryos were exposed to dilution series of primordazine. At 3 day post fertilization GFP labeled PGCs found at the midline above the intestine were counted.

To evaluate if temporally controlled treatment with primordazine can modulate PGC development in tilapia, 5 hours old tilapia embryos were first exposed to 2 fold dilution series of primordazine from 20 uM to 2.5 uM at 28° C. Primordazine treated embryos showed a reduction in the number of GFP labeled PGCs in a dose dependant manner. After 3 days, an average of 67% and 47% reduction in PGCs number were measured at 20 uM and 10 uM respectively compare to the control group (FIG. 39). Additionally, the level of GFP intensity in PGCs was reduced in primordazine treated embryos. These results parallel those observed in zebrafish, where primordazine was found to alter the localization and translation of nanos1 RNA in germ cells, leading to loss of germ cells. Nile tilapia and zebrafish show similar sensitivity to the same range of primordazine concentrations. In both fish species primordazine can apparently cross the chorion and penetrate embryonic cell layers.

To test in tilapia if the time of first exposure to primordazine affects the level of PGC ablation, 1-2 cell stage embryos (2 hpf) as well as 13 hour old embryos were treated with varied doses of primordazine. A positive correlation was found between early exposure and sensitivity to primordazine. For example, exposure to 5 uM of primordazine reduces PGCs number by 72% when the treatment begins at 2 hpf but only by 41% at the later time point. Similar results were observed across the range of primordazine concentration tested with enhanced PGCs ablation capacity in the earlier treatment (FIG. 40).

These findings suggest that primordazine acts in early developmental stage of tilapia much like what was found in zebrafish. These results point to a conserved mode of action of primordazine between Nile tilapia and zebrafish. Primordazine represents a promising new approach for controlling fish fertility and can be broadly applicable to multiple species of fish.

What is claimed is:

1. A method of sterilizing fish comprising: contacting an embryonic fish with a compound of formula (I):

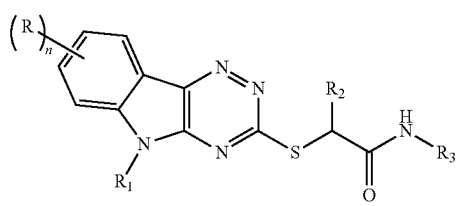

wherein n is 0;

$R_1$ is hydrogen or a substituted or unsubstituted, branched or unbranched $C_1$-$C_8$ alkyl, or $R_1$ is a linker to a solid support;

$R_2$ is hydrogen or a substituted or unsubstituted, branched or unbranched $C_1$-$C_8$ alkyl; and $R_3$ is hydrogen, a substituted or unsubstituted aryl, or a substituted or unsubstituted alkylheteroaryl, with the provisos that:

(i) when n is 0, $R_1$ is ethyl and $R_2$ is ethyl, then $R_3$ is not 5-methylisoxazol-3-yl;

(ii) when n is 0, $R_1$ is ethyl and $R_2$ is ethyl, then $R_3$ is not 1-phenylehtyl;

(iii) when n is 0, $R_1$ is ethyl and $R_2$ is ethyl, then $R_3$ is not 4-(N-hydroxynitrosyl)phenyl;

(iv) when n is 0, $R_1$ is ethyl and $R_2$ is H, then $R_3$ is not 4-(N,N-dimethylcarbamoyl)phenyl;

(v) when n is 0, $R_1$ is ethyl and $R_2$ is H, then $R_3$ is not 4-carbamoylphenyl; and (vi) when n is 0, $R_1$ is propyl and $R_2$ is H, then $R_3$ is not 1-phenylethyl;

wherein said contacting begins prior to 4 hours post fertilization and wherein said contacting leads to sterilization of the fish upon developing into an adult.

2. The method of claim 1, wherein the compound of Formula (I) is primordazine having the structure:

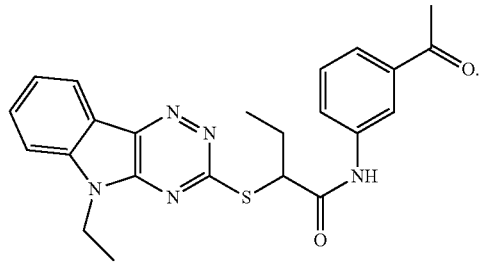

primordazine

3. A fish embryo obtained by the method of claim 1.

4. The method of claim 1, wherein $R_1$ is $C_1$-$C_4$ alkyl.

5. The method of claim 4, wherein $R_1$ is methyl, ethyl, propyl or n-butyl.

6. The method of claim 1, wherein $R_2$ is hydrogen or $C_1$-$C_4$ alkyl.

7. The method of claim 6, wherein $R_2$ is hydrogen or ethyl.

8. The method of claim 1, wherein $R_3$ is an unsubstituted phenyl or a substituted phenyl.

9. The method of claim 8, wherein $R_3$ is a phenyl substituted with acetyl or a halogen.

10. The method of claim 1, wherein $R_3$ is furanylmethyl.

11. The method of claim 1, wherein the compound of Formula (I) is selected from the group consisting of:

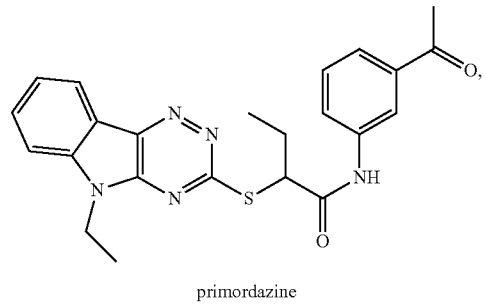

primordazine

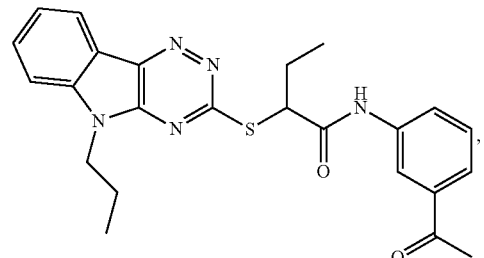

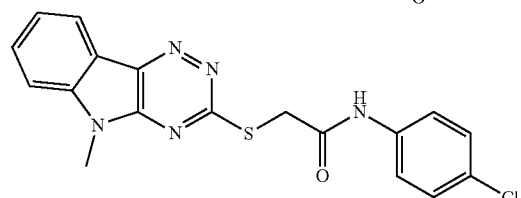

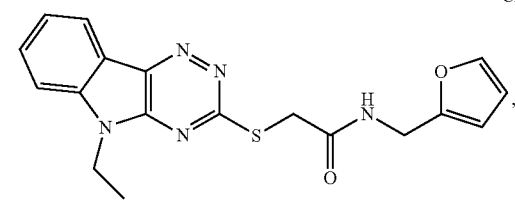

47
-continued
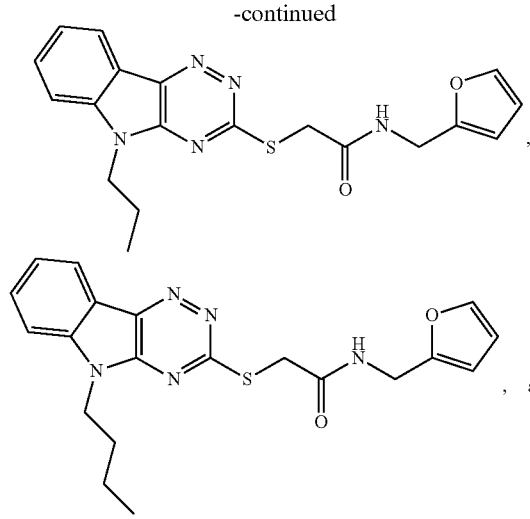
,
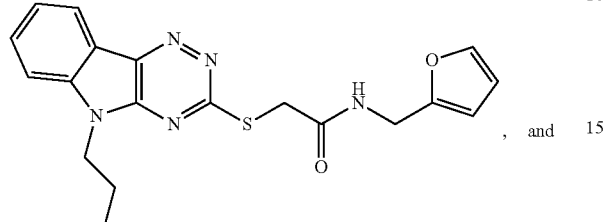
, and
48
-continued
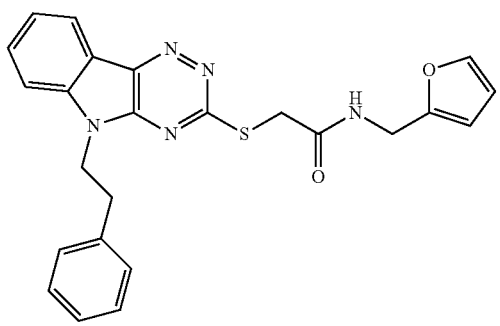
.
* * * * *

UNITED STATES PATENT AND TRADEMARK OFFICE
CERTIFICATE OF CORRECTION

| | | |
|---|---|---|
| PATENT NO. | : 9,538,734 B2 | |
| APPLICATION NO. | : 14/206135 | |
| DATED | : January 10, 2017 | |
| INVENTOR(S) | : Randall T. Peterson and Peter J. Schlueter | |

It is certified that error appears in the above-identified patent and that said Letters Patent is hereby corrected as shown below:

In Column 1, following the cross-reference section, please insert the following government support heading and paragraph at Line 12:

--GOVERNMENT SUPPORT
This invention was made with Government support under Grant No. HL007208 awarded by National Institutes of Health. The Government has certain rights in this invention.--

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*